(12) United States Patent
Oja et al.

(10) Patent No.: US 11,371,957 B2
(45) Date of Patent: Jun. 28, 2022

(54) METHOD AND APPARATUS FOR ANALYTE DETECTION USING AN ELECTROCHEMICAL BIOSENSOR

(71) Applicant: ABBOTT DIABETES CARE INC., Alameda, CA (US)

(72) Inventors: Stephen M. Oja, Alameda, CA (US); Benjamin Feldman, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 16/024,353

(22) Filed: Jun. 29, 2018

(65) Prior Publication Data
US 2019/0004005 A1 Jan. 3, 2019

Related U.S. Application Data

(60) Provisional application No. 62/545,252, filed on Aug. 14, 2017, provisional application No. 62/544,692,
(Continued)

(51) Int. Cl.
*G01N 27/327* (2006.01)
*C12Q 1/00* (2006.01)
(Continued)

(52) U.S. Cl.
CPC ..... *G01N 27/3277* (2013.01); *A61B 5/14532* (2013.01); *A61B 5/14865* (2013.01);
(Continued)

(58) Field of Classification Search
CPC .......... G01N 27/3277; G01N 27/3271; G01N 27/3272; G01N 27/3276; C12Q 1/001;
(Continued)

(56) References Cited

U.S. PATENT DOCUMENTS 6,251,260 B1 * 6/2001 Heller ................ G01N 27/3271
204/402
6,764,581 B1 * 7/2004 Forrow .................. C12Q 1/006
204/403.04
(Continued)

FOREIGN PATENT DOCUMENTS

JP 2002541441 A 12/2002
JP 2005-083928 A 3/2005
(Continued)

OTHER PUBLICATIONS

Kulys et al. (JJ Kulys, NK Cenas, GJS Svirmickas, VP Svirmickiene, Chronoamperometric stripping analysis following biocatalytic preconcentration, Analytical Chimica Acta 138 (1982) 19-26). (Year: 1982).*
(Continued)

*Primary Examiner* — Joshua L Allen
(74) *Attorney, Agent, or Firm* — Lewis Roca Rothgerber Christie LLP

(57) ABSTRACT

A method for sensing an analyte utilizing a sensor having a working electrode, the method includes providing the working electrode with an analyte-specific enzyme and a redox mediator, providing the working electrode to the analyte, accumulating charge derived from the analyte reacting with the analyte-specific enzyme and the redox mediator for a set period of time, connecting the working electrode to circuit after the set period of time, and measuring the signal from the accumulated charge.

17 Claims, 33 Drawing Sheets

Related U.S. Application Data filed on Aug. 11, 2017, provisional application No. 62/527,981, filed on Jun. 30, 2017.

(51) Int. Cl.

| | | |
|---|---|---|
| *A61B 5/145* | (2006.01) | |
| *A61B 5/1486* | (2006.01) | |
| *A61B 5/00* | (2006.01) | |

(52) U.S. Cl.
CPC ............. *C12Q 1/001* (2013.01); *C12Q 1/004* (2013.01); *G01N 27/3271* (2013.01); *G01N 27/3272* (2013.01); *G01N 27/3276* (2013.01); *A61B 5/002* (2013.01); *C12Q 2527/113* (2013.01)

(58) Field of Classification Search
CPC ............. C12Q 1/004; C12Q 2527/113; A61B 5/14532; A61B 5/14865; A61B 5/002
See application file for complete search history.

(56) References Cited

U.S. PATENT DOCUMENTS

| | | | | |
|---|---|---|---|---|
| 6,773,671 | B1* | 8/2004 | Lewis | G01N 33/521 422/169 |
| 2005/0023152 | A1* | 2/2005 | Surridge | C12M 1/00 205/775 |
| 2005/0183965 | A1* | 8/2005 | Davies | A61B 5/1486 205/775 |
| 2009/0194432 | A1* | 8/2009 | Deng | A61B 5/1495 205/792 |
| 2010/0022850 | A1* | 1/2010 | Mc Kenna | A61B 5/103 600/301 |
| 2011/0060530 | A1* | 3/2011 | Fennell | A61B 5/002 702/19 |
| 2012/0132525 | A1* | 5/2012 | Liu | C12Q 1/002 204/403.14 |
| 2013/0098778 | A1 | 4/2013 | Wu | |
| 2014/0054171 | A1* | 2/2014 | Feldman | G01N 27/3272 204/403.14 |
| 2016/0177365 | A1 | 6/2016 | Katsuki | |

FOREIGN PATENT DOCUMENTS

| | | |
|---|---|---|
| RU | 2415410 C2 | 3/2011 |
| WO | 93/23744 A1 | 11/1993 |
| WO | 0059373 A1 | 10/2000 |
| WO | WO2005/033698 | 4/2005 |
| WO | 2015020149 A1 | 2/2015 |

OTHER PUBLICATIONS

Cenas et al. (NK Cenas, JJ Kulys, Biocatalytic oxidation of glucose on the conductive charge transfer complexes, Bioelectrochemistry and Bioenergetics 8 (1981) 103-113). (Year: 1981).*

Mizutani et al. (F Mizutani, E Ohta, Y Mie, O Niwa, Determination of hydrogen peroxide based on the charge accumulation and electrochemical reduction at an osmium complex/peroxidase-coated electrode, Chemistry Letters 36(9) (2007) 1148-1149). (Year: 2007).*

Joshi et al. (PP Joshi, SA Merchant, Y Wang, DW Schmidtke, Amperometric biosensors based on redox polymer-carbon nanotube-enzyme composites, Anal. Chem. 77 (2005) 3183-3188). (Year: 2005).*

Feldman et al. (B Feldman, R Brazg, S Schwartz, R Weinstein, A continuous glucose sensor based on wired enzyme technology-results from a 3-day trial in patients with type 1 diabetes, Diabetes Technology and Therapeutics, 5(5) (2003) 769-779) (Year: 2003).*

Yasukawa et al. (T Yasukawa, S Inadumi, R Harada, S Shinagawa, H Nose, F Mizutani, Highly sensitive detection of N1,N12-diacetylspermine based on electrochemical charge accumulation, Chem. Lett. 39 (2010) 88-89) (Year: 2010).*

Granot et al. (E Granot, B Basnar, Z Cheglakov, E Katz, I Willner, Enhanced bioelectrocatalysis using single-walled carbon nanotubes (SWCNTs)/polyaniline hybrid system in thin-film and microrod structures associated with electrodes, Electroanalysis 18 (2006) 26-34) (Year: 2006).*

Heller (A Heller, Electrical wiring of redox enzymes, Acc. Chem. Res. 23 (1990) 128-134) (Year: 1990).*

International Search Report and Written Opinion issued in corresponding application No. PCT/US2018/040471, dated Sep. 27, 2018, 14 pages.

Čenas, N.K. et al., Biocatalytic Oxidation of Glucose on the Conductive Charge Transfer Complexes, Bioelectrochemistry and Bioenergetics, 1981, pp. 103-113.

Kulys, J.J. et al., Chronoamperometric Stripping Analysis Following Biocatalytic Preconcentration, Analytica Chimica Acta, vol. 138, 1982, pp. 19-26.

Kulys, J.J., Enzyme Electrodes Based on Organic Metals, Biosensors 2, 1986, pp. 3-13.

Oja, S.M. et al., Method for Low Nanomolar Concentration Analyte Sensing Using Electrochemical Enzymatic Biosensors, Analytical Chemistry, 2018, vol. 90, pp. 1536-1541.

Schubert, F. et al., Augmentation of enzyme electrode sensitivity using biocatalytic preconcentration, Analytica Chimica Acta, vol. 243, 1991, pp. 17-21.

RU Patent Office Action and Search dated May 27, 2020 issued by the FIIP in corresponding Russian Patent Application No. 2020103724/10(005651), with English translations.

English Translation of Japanese Office Action dated Feb. 24, 2021, of the corresponding Japanese Patent Application No. 2019-572054 (5 pages).

Examination Report dated May 26, 2021, for corresponding European Patent Application No. 18 752 316.2-1118 (6 pages).

Liying Jiang, et al., "A sensitive biosensor based on Os-complex mediator and glucose oxidase for low concentration glucose determination," Journal of Electroanalytical Chemistry, 2008, 619-620, pp. 11-16.

Katsunobu Yamamoto et al., "Evaluation of an amperometric glucose biosensor based on a ruthenium complex mediator of low redox potential," Science Direct, Talanta 66 (2005), pp. 1175-1180.

English Translation of Japanese Office Action dated Oct. 6, 2021, of the corresponding Japanese Patent Application No. 2019-572054 (5 pages).

* cited by examiner

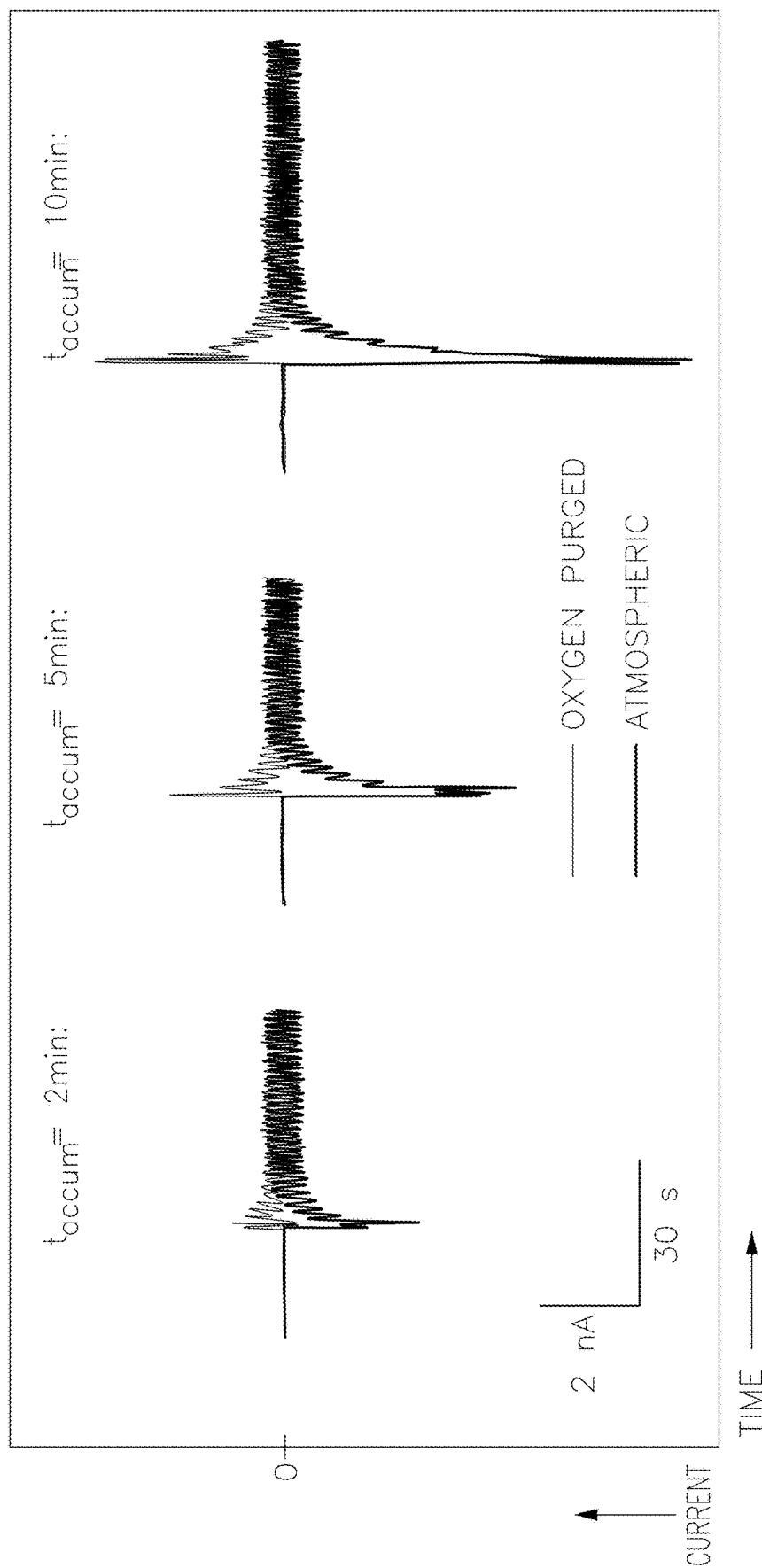

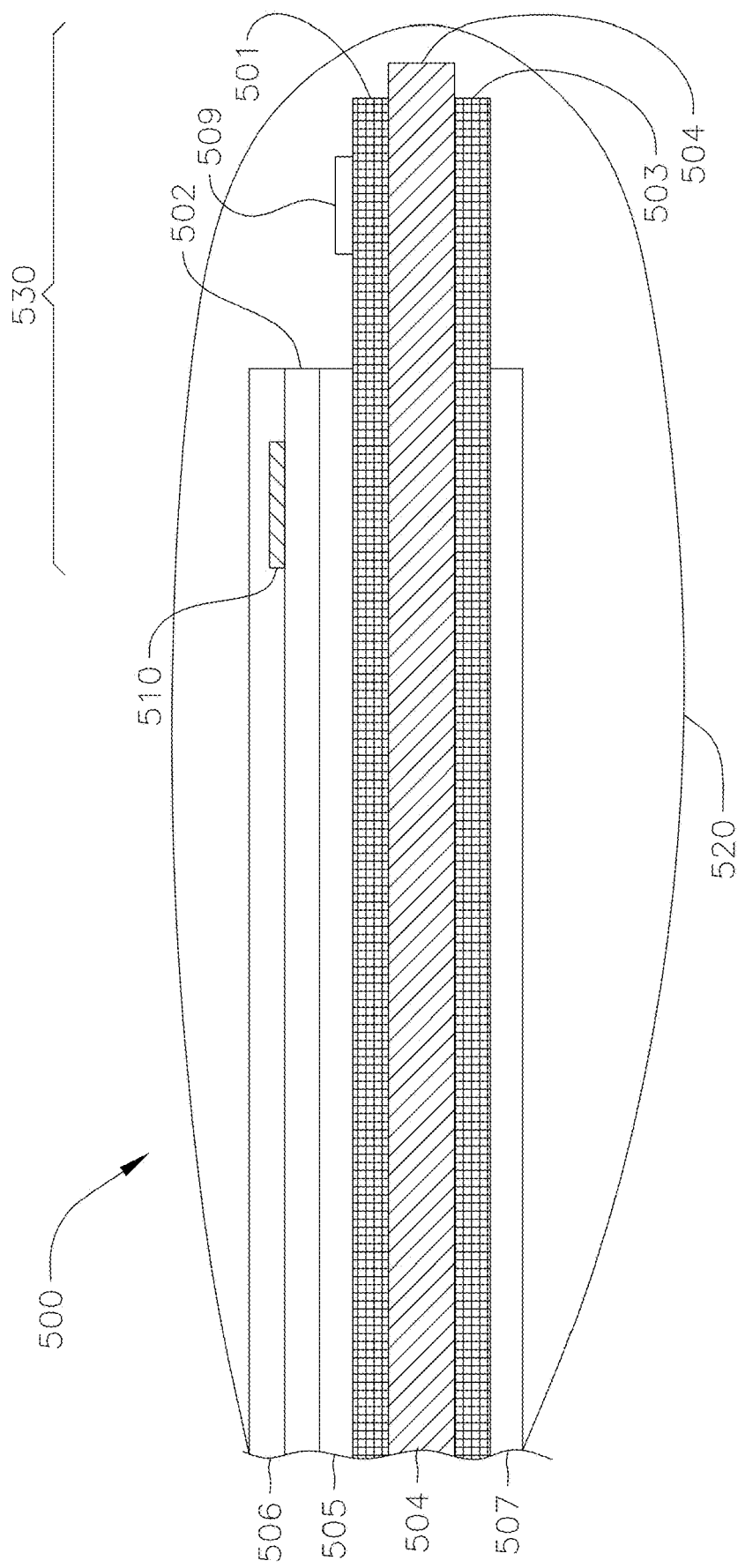

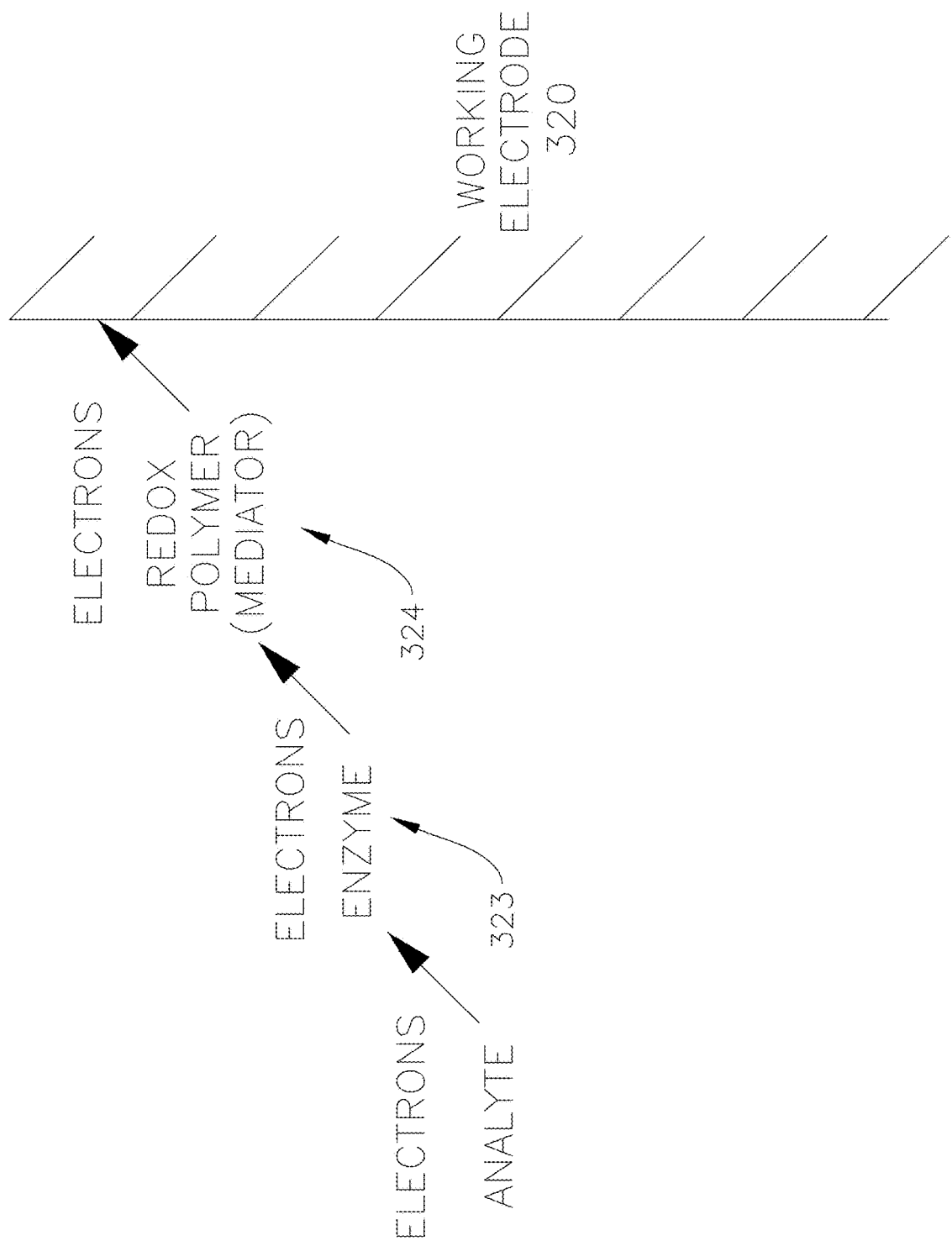

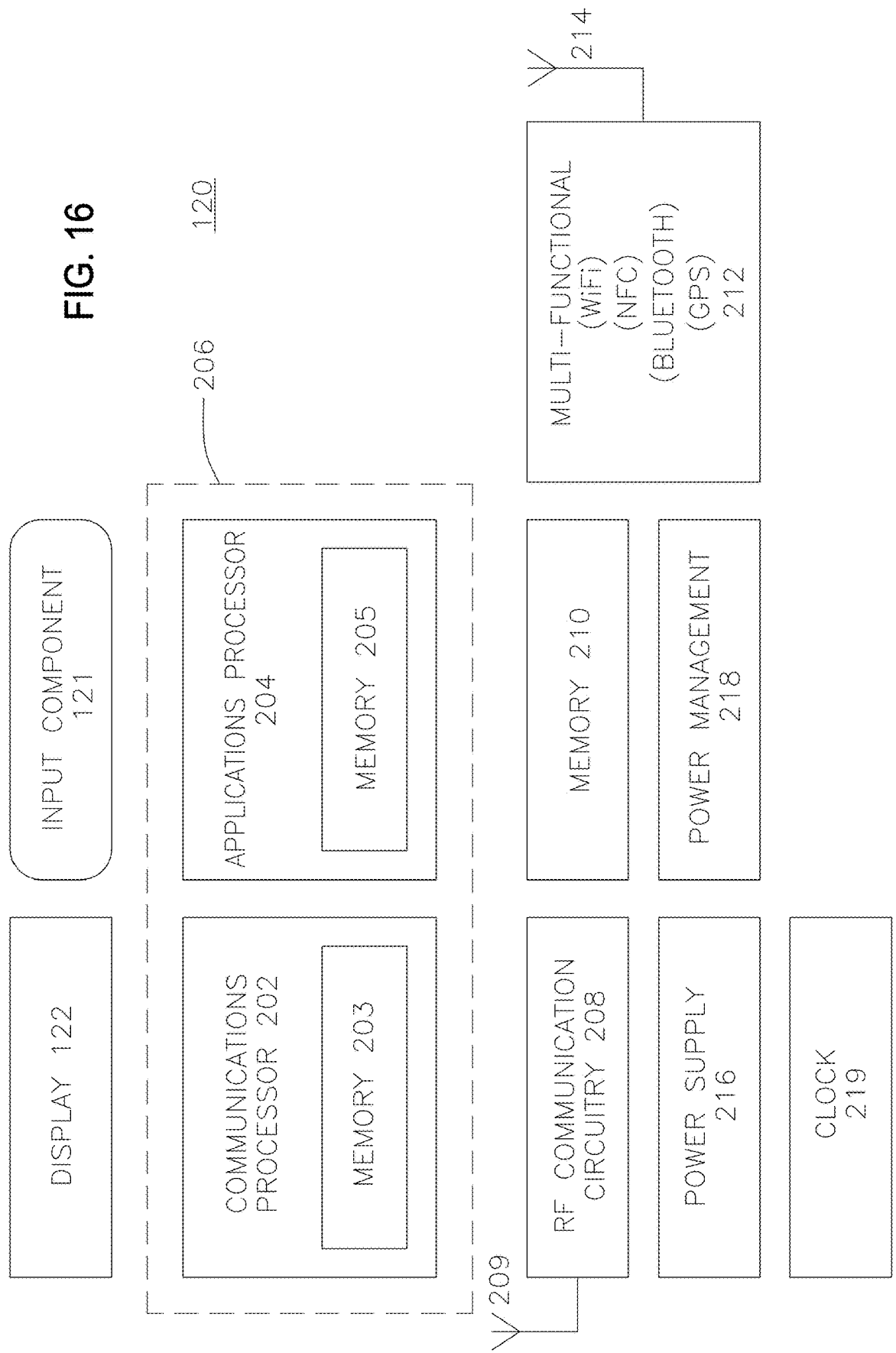

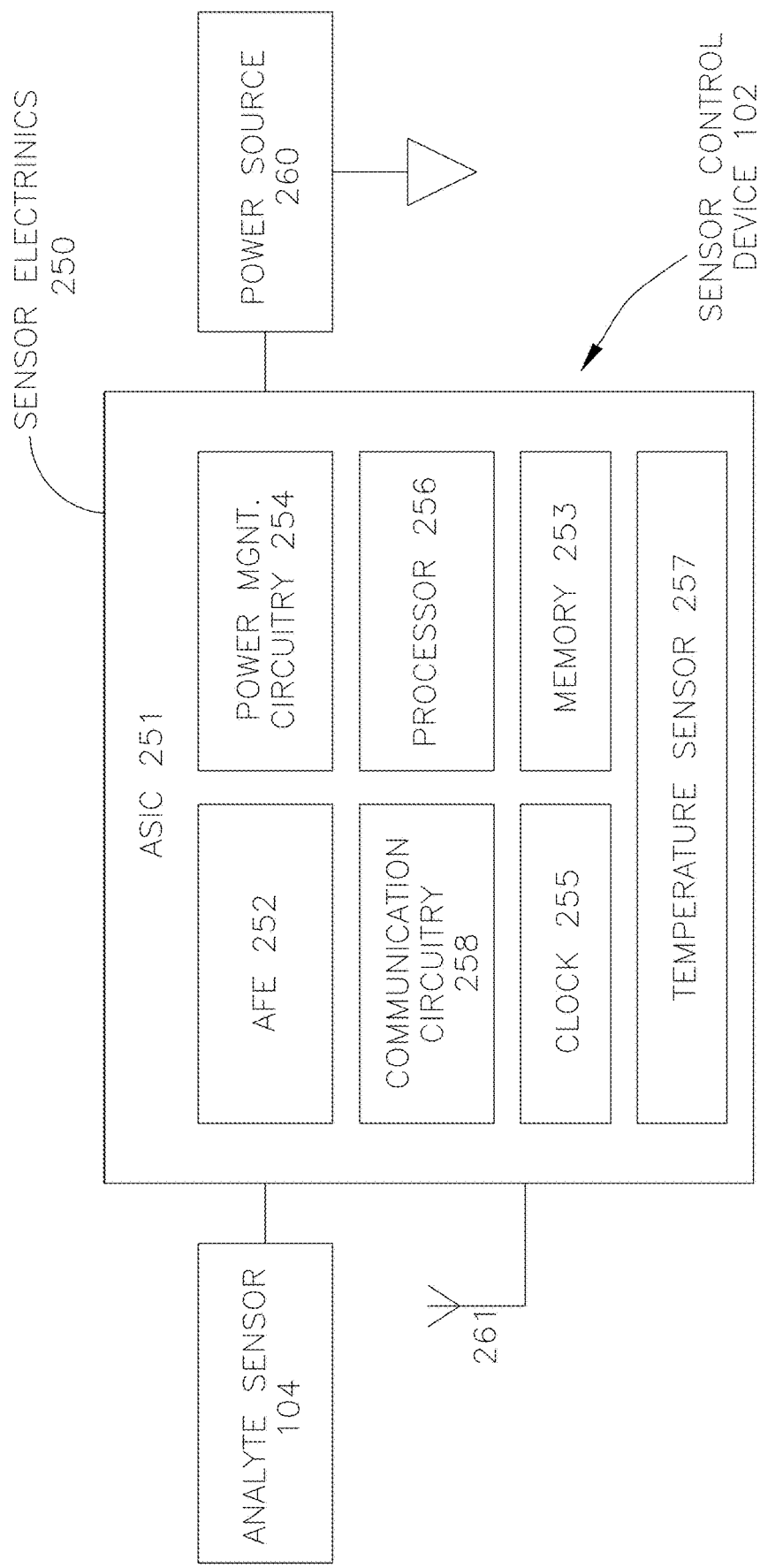

METHOD AND APPARATUS FOR ANALYTE DETECTION USING AN ELECTROCHEMICAL BIOSENSOR

CROSS-REFERENCE TO RELATED APPLICATION(S)

This patent application claims the benefits of U.S. Provisional Patent Application Ser. No. 62/527,981, filed on Jun. 30, 2017; U.S. Provisional Patent Application Ser. No. 62/544,692, filed Aug. 11, 2017; and U.S. Provisional Patent Application Ser. No. 62/545,252, filed Aug. 14, 2017, the entire contents of all of which are hereby expressly incorporated by reference.

STATEMENT REGARDING FEDERALLY SPONSORED RESEARCH OR DEVELOPMENT

This invention was made with government support under Contract No. HDTRA-1-16-C-0048 awarded by the Defense Threat Reduction Agency. The government has certain rights in the invention.

FIELD

Embodiments of the present disclosure relate to analyte sensing using electrochemical enzymatic biosensors. For example, embodiments of the present disclosure relate to a method and an enzymatic biosensor that allow for the detection of low concentrations of analyte by allowing for an accumulation of the analyte on the biosensor.

BACKGROUND

Enzymatic biosensors that utilize enzymes associated with a transducer as a biorecognition element for a target analyte have been developed and utilized. While many different signal transduction methods have been used, the most frequently used has been electrochemical. Electrochemical biosensors allow for the biological event (e.g., analyte detection) to be directly converted to an electrical signal, which obviates the need for complex instrumentation, thereby giving electrochemical biosensors desirable features in terms of size, cost, and portability. Among the electrochemical techniques used for signal transduction, amperometry is often used. In an amperometric measurement, the working electrode of the sensor is held at a constant potential (voltage) while the current flowing through the sensor is measured. The sensor is designed such that the current is dependent upon analyte concentration.

An example of an enzymatic biosensor utilizing amperometry is the continuous glucose sensor, which is a wearable, in vivo device designed to provide frequent blood glucose concentration measurements to the user. These devices utilize a glucose oxidoreductase enzyme, such as glucose oxidase (GOx), immobilized on a working electrode as the glucose-sensing element. Electrons are first passed from glucose to the enzyme via enzymatic oxidation, and then to the working electrode through a redox mediator, such as oxygen ($O_2$) or an Osmium (Os)-containing redox polymer. While amperometry has proven viable for measuring analytes such as glucose, which is present at relatively high physiological concentrations (at or above 5 millimolar (mM)), it may not be suitable for measuring analytes present at lower concentrations

SUMMARY

Aspects of embodiments of the present disclosure are directed toward detection of low concentrations (e.g., at or less than 5 mM, 1 nanomolar (nM) to 5 mM, or 4.7 nM to 5 mM) of analyte by allowing for an accumulation of the analyte on an enzymatic biosensor.

In some embodiments of the present disclosure, a method for sensing an analyte utilizing a sensor having a working electrode, where the method includes providing the working electrode with an analyte-specific enzyme and a redox mediator, providing the working electrode to the analyte, accumulating charge derived from the analyte reacting with the analyte-specific enzyme and the redox mediator for a set period of time, connecting the working electrode to a circuit after the set period of time, and measuring a signal from the accumulated charge.

In some embodiments of the present disclosure, prior to providing the working electrode to an analyte, the method includes connecting the working electrode to the circuit, and prior to providing the working electrode to the analyte, the method includes disconnecting the working electrode from the circuit.

In some embodiments of the present disclosure, the working electrode is connected to the circuit prior to providing the working electrode to the analyte, and the method includes disconnecting the working electrode from the circuit prior to providing the working electrode to the analyte.

In some embodiments of the present disclosure, the sensor is an enzymatic electrochemical biosensor.

In some embodiments of the present disclosure, the redox mediator is an immobilized redox polymer.

In some embodiments of the present disclosure, the immobilized redox polymer includes a redox species and a polymer, the redox species is selected from osmium (Os), ruthenium (Ru), iron (Fe), or cobalt (Co)-containing polymer, and the polymer selected from poly(vinylpyridine), poly(thiophene), poly(aniline), poly(pyrrole), or poly(acetylene).

In some embodiments of the present disclosure, the immobilized redox polymer is an Os-containing poly(vinylpyridine).

In some embodiments of the present disclosure, the analyte is selected from cortisol, glucose, lactate, 3-hydroxy butyrate, alcohol, pyruvate, glutamate, theophylline, or creatinine.

In some embodiments of the present disclosure, the analyte-specific enzyme is a nicotinamide adenine dinucleotide (NAD)-dependent dehydrogenase, a flavin adenine dinucleotide (FAD)-dependent oxidase, and/or a flavin mononucleotide (FMN)-dependent oxidase.

In some embodiments of the present disclosure, analyte-specific enzyme is selected from 11β-hydroxysteroid dehydrogenase type 2 (11β-HSD-2), glucose oxidase, NAD-glucose dehydrogenase, FAD-glucose dehydrogenase, lactate oxidase, NAD-lactate dehydrogenase, NAD-alcohol dehydrogenase, pyruvate oxidase, NAD-glutamate dehydrogenase, or xanthine oxidase.

In some embodiments of the present disclosure, the accumulating of charge includes accumulating electrons.

In some embodiments of the present disclosure, the sensor is placed subcutaneously in a subject.

In some embodiments of the present disclosure, the analyte is at a concentration as low as 4.7 nanomolar (nM).

In some embodiments of the present disclosure, the set period of time ranges from 60 seconds to 30 minutes. In some embodiments, the set period of time ranges from 120 seconds to 30 minutes. In some embodiments, the set period of time ranges from 120 seconds to 10 minutes.

In some embodiments of the present disclosure, the sensor includes an outer membrane. In some embodiments, the outer membrane is a flux-limiting membrane. In some embodiments, the outer membrane is an analyte-permeable membrane.

In some embodiments of the present disclosure, the measuring of the signal from the accumulated charge includes measuring a peak height of the signal and/or measuring a peak area of the signal.

In some embodiments, the method further includes calibrating the measured peak height to provide a concentration of the analyte.

In some embodiments, the method further includes calibrating the measured peak area to provide a concentration of the analyte.

In some embodiments, the measuring of the signal from the accumulated charge comprises recording the signal at a sampling rate of 0.1 to 0.5 hertz (Hz) and/or filtering the signal at a frequency of 0.032 to 3.2 hertz (Hz).

In some embodiments of the present disclosure, the working electrode includes a sensing element comprising the analyte-specific enzyme and the redox mediator. In some embodiments, the sensing element also includes carbon nanotubes.

In some embodiments, a method for sensing an analyte utilizing a sensor, the sensor including a working electrode including an analyte-specific enzyme and a redox mediator, includes: providing the working electrode to the analyte; accumulating charge derived from the analyte reacting with the analyte-specific enzyme and the redox mediator; and measuring a signal from the accumulated charge by measuring a peak height of the signal and/or measuring a peak area of the signal.

In some embodiments of the present disclosure, a system for sensing an analyte includes a working electrode, a sensing element disposed on the working electrode, the sensing element including an analyte-specific enzyme and a redox mediator, the sensing element configured to accumulate charge derived from the analyte reacting with the analyte-specific enzyme for a set period of time, and a circuit configured to connect with the working electrode after the set period of time, and to measure the signal from the accumulated charge. In some embodiments, the sensing element of this system includes carbon nanotubes. In some embodiments, this system also includes an outer membrane overlaying at least the sensing element. In some embodiments, the analyte-specific enzyme of this system is selected from a nicotinamide adenine dinucleotide (NAD)-dependent dehydrogenase, a flavin adenine dinucleotide (FAD)-dependent oxidase, or a flavin mononucleotide (FMN)-dependent oxidase. For example, in some embodiments, the analyte-specific enzyme of this system is selected from 11β-hydroxysteroid dehydrogenase type 2 (11β-HSD-2), glucose oxidase, NAD-glucose dehydrogenase, FAD-glucose dehydrogenase, lactate oxidase, NAD-lactate dehydrogenase, NAD-alcohol dehydrogenase, pyruvate oxidase, NAD-glutamate dehydrogenase, and xanthine oxidase.

BRIEF DESCRIPTION OF THE DRAWINGS

FIG. 10A shows the accumulation mode signals from a representative glucose sensor under background conditions ([glucose]=0) in an open-to-atmosphere (bold line) and oxygen-purged (thin line) buffer solution, according to embodiments of the present disclosure.

FIG. 14B is a cross-sectional view depicting a portion of any analyte sensor having a membrane that is compatible with one or more embodiments of the present disclosure.

FIG. 14D is a schematic depicting a redox reaction of an analyte with an analyte-specific enzyme and a redox mediator on a working electrode, according to embodiments of the present disclosure.

FIG. 16 is a block diagram of an embodiment of a reader device of the analyte monitoring system of FIG. 15, according to embodiments of the present disclosure.

FIG. 17 is a block diagram of an embodiment of a sensor control device of the analyte monitoring system of FIG. 15, according to embodiments of the present disclosure.

DETAILED DESCRIPTION

Figure 1:
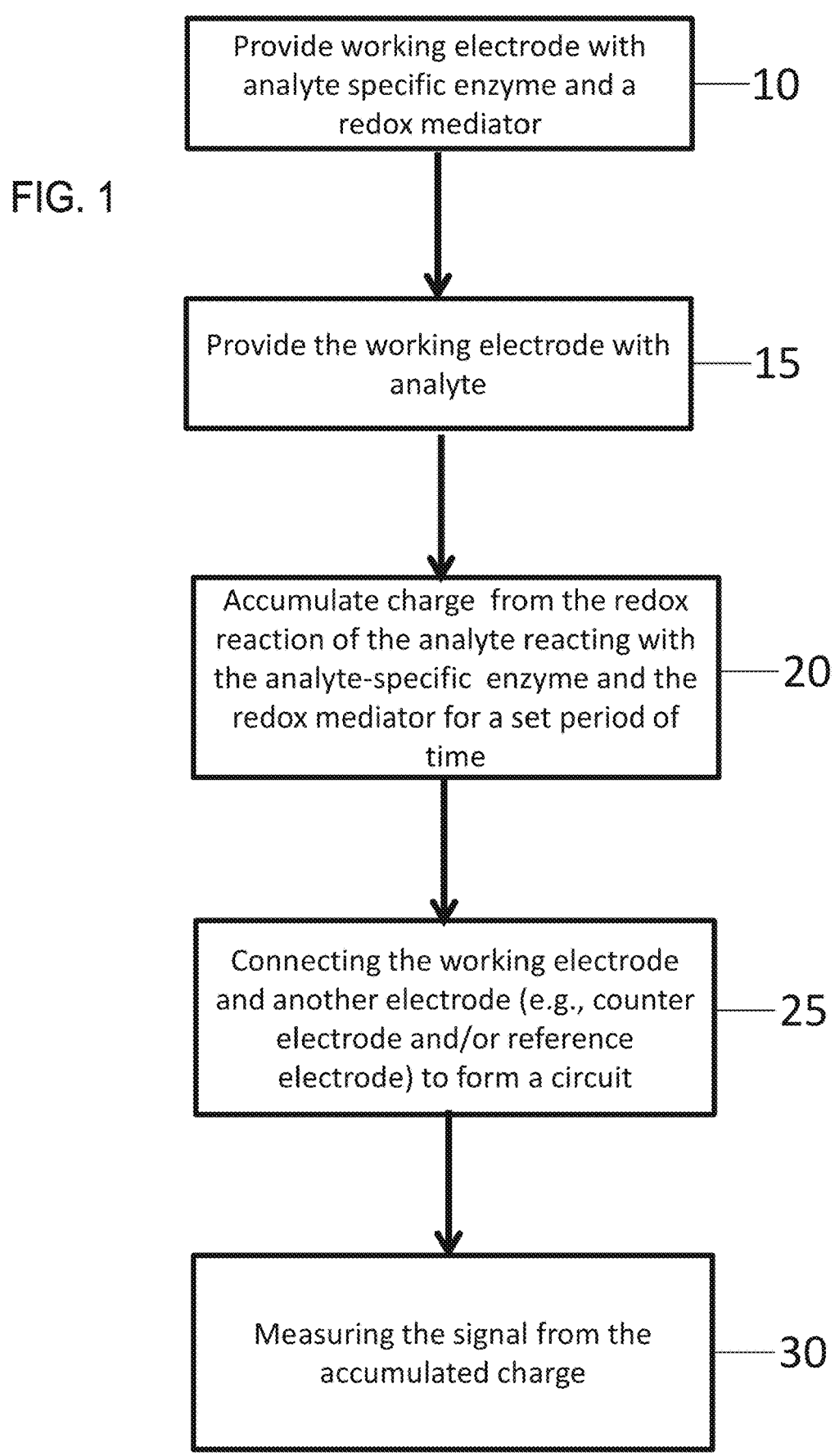
FIG. 1 is a flow chart describing a method for accumulation mode sensing including actions 10, 15, 20, 25, and 30, as indicated, according to embodiments of the present disclosure.

Embodiments of the present disclosure provide a method of electrochemical measurement using an electrochemical sensor for measuring low nanomolar concentrations of analyte in vitro and in vivo. Embodiments of the present disclosure include an electrochemical sensor such as an enzymatic biosensor modified for measuring low nanomolar concentrations of an analyte.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

As used herein, the terms "substantially," "about," and similar terms are used as terms of approximation and not as terms of degree, and are intended to account for the inherent deviations in measured or calculated values that would be recognized by those of ordinary skill in the art.

In the description as disclosed herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

As used herein, the terms "measure," "measuring," and "measured" may encompass the meaning of a respective one of the terms "determine," "determining," "determined," "calculate," "calculating," and "calculated."

As used herein, an "electrochemical sensor" is a device configured to detect the presence and/or measure the level of an analyte in a sample via electrochemical oxidation and reduction reactions on the sensor. These reactions are transduced to an electrical signal that may be correlated to an amount, concentration, or level of an analyte in the sample.

As used herein, a "working electrode" is an electrode at which the analyte (or a second compound whose level depends on the level of the analyte) is electrooxidized or electroreduced with or without the agency of an electron transfer agent.

As used herein, a "counter electrode" refers to an electrode paired with the working electrode, through which passes a current equal in magnitude and opposite in sign to the current passing through the working electrode. In the context of embodiments of the present disclosure, the term "counter electrode" includes both a) counter electrodes and b) counter electrodes that also function as reference electrodes (i.e., counter/reference electrodes), unless otherwise indicated.

As used herein, a "reference electrode" includes both a) reference electrodes and b) reference electrodes that also function as counter electrodes (i.e., counter/reference electrodes), unless otherwise indicated.

As used herein, "electrolysis" is the electrooxidation or electroreduction of a compound either directly at an electrode or via one or more electron transfer agents.

As used herein, components are "immobilized" within a sensor, for example, when the components are entrapped on or covalently, ionically, or coordinatively bound to constituents of the sensor and/or are entrapped in a polymeric or sol-gel matrix or membrane which precludes mobility.

As used herein an "electron transfer agent" is a compound that carries electrons between the analyte and the working electrode, either directly, or in cooperation with other electron transfer agents. One example of an electron transfer agent is a redox mediator.

As used herein, a "redox mediator" is an electron-transfer agent for carrying electrons between an analyte, an analyte-reduced or analyte-oxidized, enzyme, and an electrode, either directly, or via one or more additional electron-transfer agents. A redox mediator that includes a polymeric backbone may also be referred to as a "redox polymer".

As used herein, the term "precursor polymer" refers to the starting polymer before the various modifier groups are attached to form a modified polymer.

As used herein, a "sensing layer" is a component of the sensor which includes constituents that facilitate the electrolysis of the analyte. The sensing layer may include constituents such as an electron transfer agent (e.g., a redox mediator or a redox polymer), a catalyst (e.g., an analyte-specific enzyme) which catalyzes a reaction of the analyte to produce a response at the working electrode, or both an electron transfer agent and a catalyst. In some embodiments of the present disclosure, a sensor includes a sensing layer that is non-leachably disposed in proximity to or on the working electrode.

As used herein, a "sensing element" is an application or region of an analyte-specific enzyme disposed with the sensing layer. As such, a sensing element is capable of interacting with the analyte. A sensing layer may have more than one sensing element making up the analyte detection area disposed on the working electrode. In some embodiments, the sensing element includes an analyte-specific enzyme and an electron transfer agent (e.g., redox mediator). In some embodiments, the sensing element includes an analyte specific enzyme, an electron transfer agent, and a crosslinker.

As used herein, a "non-leachable," or "non-releasable" compound, or a compound that is "non-leachably disposed" is meant to define a compound that is affixed on the sensor such that it does not substantially diffuse away from the sensing layer of the working electrode for the period in which the sensor is used (e.g., the period in which the sensor is implanted in a patient or measuring a sample).

As used herein, "crosslinker" is a molecule that contains at least two reactive groups capable of linking at least two molecules together, or linking at least two portions of the same molecule together. Linking of at least two molecules is called intermolecular crosslinking, while linking of at least two portions of the same molecule is called intramolecular crosslinking. A crosslinker having more than two reactive groups may be capable of both intermolecular and intramolecular crosslinkings at the same time.

A "membrane solution" is a solution that contains all necessary components for crosslinking and forming the membrane, including a modified polymer containing heterocyclic nitrogen groups, a crosslinker and a buffer or an alcohol-buffer mixed solvent.

As used herein, a "biological fluid" or a "biofluid" is any body fluid or body fluid derivative in which the analyte may be measured, for example, blood, interstitial fluid, plasma, dermal fluid, sweat, and tears.

As used herein, "accumulation mode sensing" refers to the accumulation of electrons produced from the oxidation of an analyte, the oxidation occurring at or on the sensing element of a working electrode that is not connected to a circuit, thereby creating the accumulation of electrons.

Accumulation Mode Sensing

With reference to the method flow chart of FIG. 1, some embodiments of the present disclosure include a method for obtaining a signal from an analyte utilizing a sensor, the sensor including a working electrode and another electrode (e.g., a counter and/or reference electrode) where the working electrode is provided or modified with (10) a catalyst such as an analyte-specific enzyme and an electron transfer agent (e.g., a redox mediator). The area of the working electrode that is modified with the analyte-specific enzyme and the redox mediator may be referred to as the sensing element or sensing layer of the working electrode. As shown in FIG. 1, the working electrode that has been provided with (e.g., modified with) an analyte-specific enzyme is provided (15) with analyte. In the presence of analyte the modified working electrode oxidizes the analyte and the amount of oxidation is measured as the amount of electron charge produced from the reaction. As long as the working electrode is not connected to another electrode, the charge from the redox reaction will continue to accumulate (20) on the working electrode. For analytes in low concentration in the body (e.g., cortisol) the accumulation of charge (electrons) for a set period of time allows for low concentrations of analyte to result in a signal output that is easy to measure and quantify compared to other known methods. After a set period of time for charge accumulation (e.g. up to 120 seconds, up to 3 minutes, up to 5 minutes, up to 10 minutes, up to 15 minutes, up to 20 minutes, up to 25 minutes, or up to 30 minutes), the working electrode is connected (25) with at least one other electrode such as a counter electrode and/or reference electrode to form a circuit. Upon formation of the circuit, the accumulated electrons on the working electrode are discharged as an electrical signal, the amplitude of which is measured (30) and correlates to the amount of analyte present at the working electrode. As such, following the method according to embodiments of the present disclosure as depicted in actions 10, 15, 20, 25, and 30 of FIG. 1, low concentrations (e.g., nanomolar amounts as low as 4.7 nM) of an analyte may be readily detected and measured.

Figure 2:
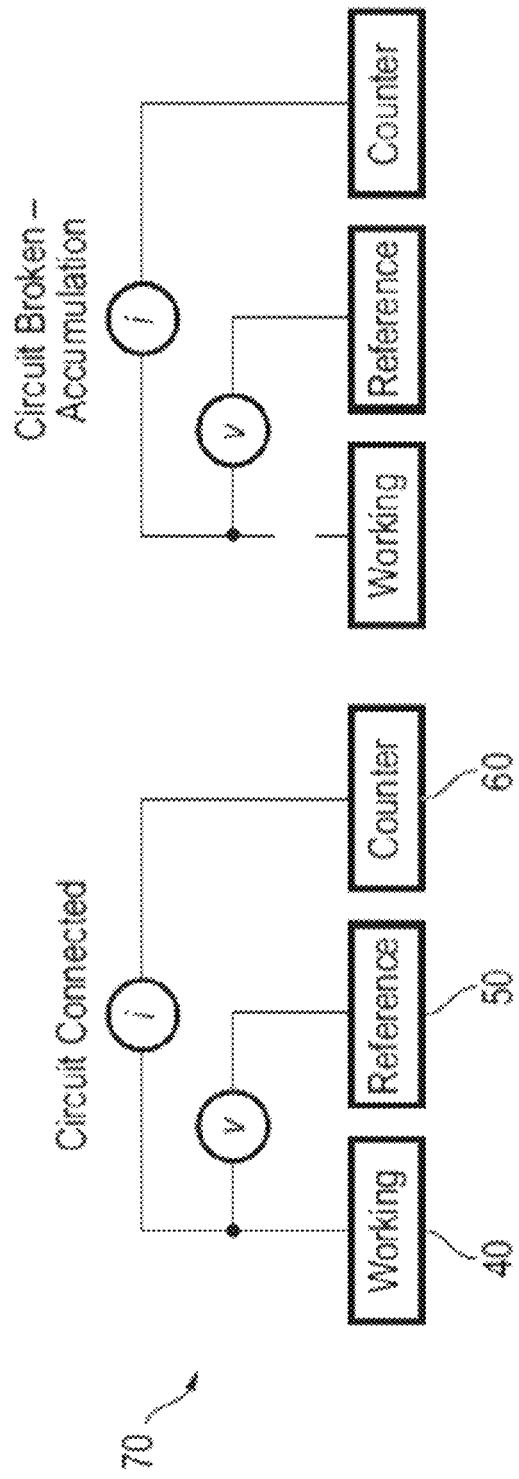
FIG. 2 shows a schematic diagram of the electrode setups used for accumulation mode sensing according to embodiments of the present disclosure in which when the circuit is connected as shown in the left panel, the working electrode is poised at a potential (voltage) sufficient to drive the redox reaction of the analyte under steady-state conditions, and when the circuit is disconnected as shown in the right panel, the working electrode is electrically disconnected from the circuit, enabling electrons from the analyte to be stored in the redox polymer until the working electrode is reconnected to the circuit and the stored charge may be measured.

With reference to FIG. 2, an example of a three electrode set-up is shown with a working electrode 40, a reference electrode 50, and a counter electrode 60 used for accumulation mode sensing according to embodiments of the present disclosure in which when the circuit 70 is connected as shown in the left panel, the working electrode is poised at a potential (voltage) sufficient to drive the redox reaction of the analyte under steady-state conditions. For example, for the example glucose sensor used herein, the potential (voltage) sufficient to drive the redox reaction is +40 mV vs. Ag/AgCl. When the circuit 70 is not connected as shown in the right panel, the working electrode 40 is electrically disconnected from the circuit 70, enabling charge (e.g., electrons) from the analyte to be stored in the redox polymer until the working electrode 40 is reconnected to the circuit 70 and the stored charge is measured.

Figure 3A:
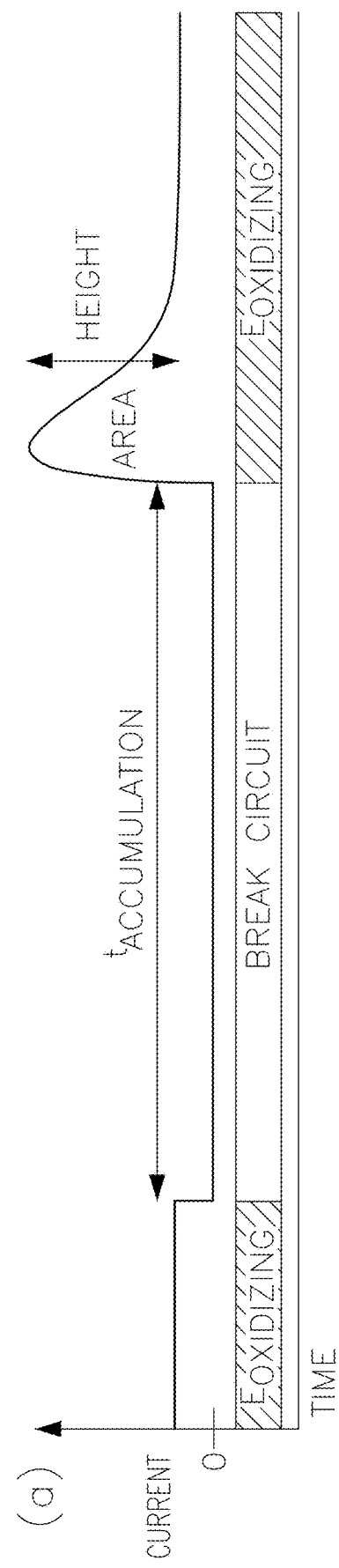
FIG. 3A shows the expected current versus (vs.) time signal and certain quantitative parameters (accumulation time when the circuit is broken, peak area, and peak height, each as indicated) of accumulation mode sensing, according to embodiments of the present disclosure.
Figure 3B:
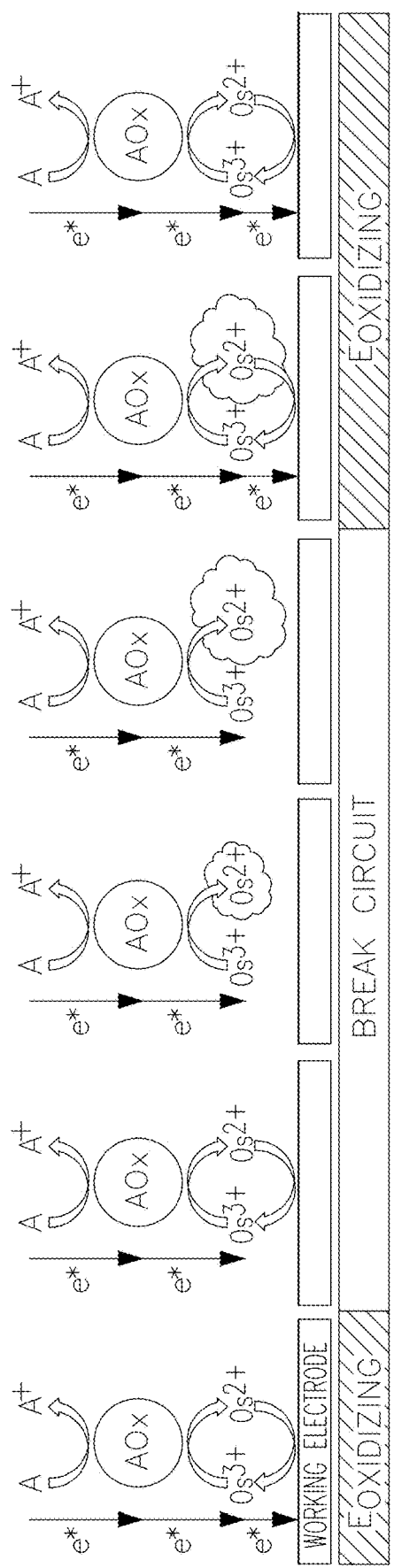
FIG. 3B shows a schematic of the redox reactions occurring during accumulation mode sensing (when circuit is broken as depicted as "break circuit' as indicated) of an oxidizable analyte (analyte A) using an oxidase enzyme (AOx) co-immobilized with an osmium redox polymer ($Os^{3+}$), according to embodiments of the present disclosure.

With reference to FIGS. 3A and 3B, an example of an electrochemical enzymatic biosensor is depicted in a conceptual overview of an accumulation mode. In this example, the sensing of the analyte (A) relies on having an oxidoreductase enzyme (AOx) electrically "wired" to the working electrode of the sensor through a redox polymer. During normal amperometric sensing, the electrode is poised at a potential (voltage) so that the analyte is reacted at a constant rate, which is proportional to the analyte concentration. For an analyte oxidation reaction (A to A+), as shown in FIG. 3B, the electrons will flow from the analyte (A) to the analyte-specific enzyme (AOx) to the redox polymer (e.g., Os3+) to the working electrode at a constant rate, producing a steady-state current as shown in FIG. 3A. If the working electrode is disconnected from the circuit, the flow of electrons from the redox polymer to the working electrode will stop, resulting in no current flow through the circuit. However, the analyte will still undergo enzymatic oxidation, which in turn results in reduction of the redox polymer (Os3+ to Os2+). This results in a buildup (depicted by the "cloud" of Os2+) of the reduced form of the redox polymer (Os2+) over time, as electrons (e−) from the analyte are stored in the redox polymer. When the working electrode is reconnected to the circuit so that it is poised at its original potential (voltage), the buildup of the reduced form of the redox polymer will be oxidized, resulting in a large current spike as shown in FIG. 3A. The current will then decay back to the original amperometric current as the redox system reaches steady-state once again. This two-step process forms the basis for accumulation mode sensing: one in which the working electrode of the sensor is disconnected from or not connected to the circuit for a set period of time (also referred to as the accumulation time), enabling charge from the analyte to "accumulate" in the redox polymer, and a second in which the working electrode of the sensor is connected to the circuit after the accumulation time, enabling the accumulated charge to be discharged and measured as a sharp peak.

Figure 3C:
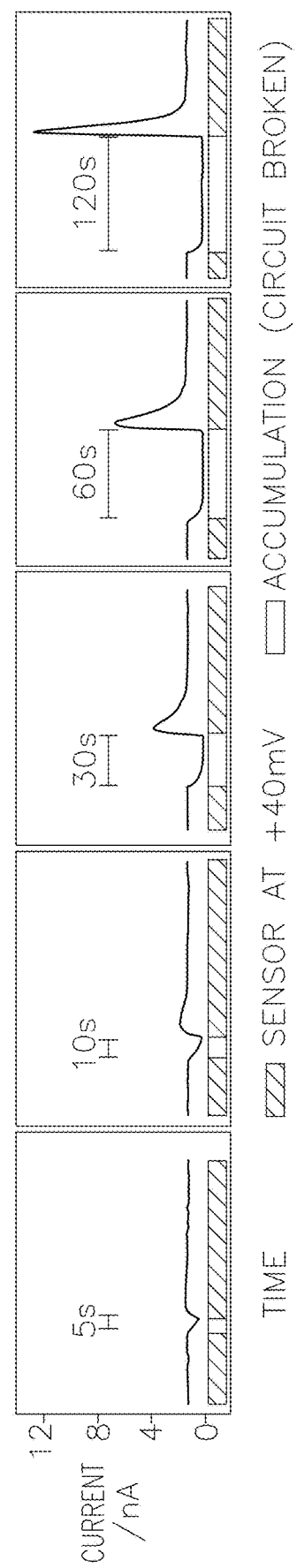
FIG. 3C shows the current vs. time traces obtained for accumulation mode sensing (as indicated in white) of 2 µM glucose using an example glucose sensor (at +40 mV as indicated with hatched lines) and measured for five different accumulation times, according to embodiments of the present disclosure.
Figure 3D:
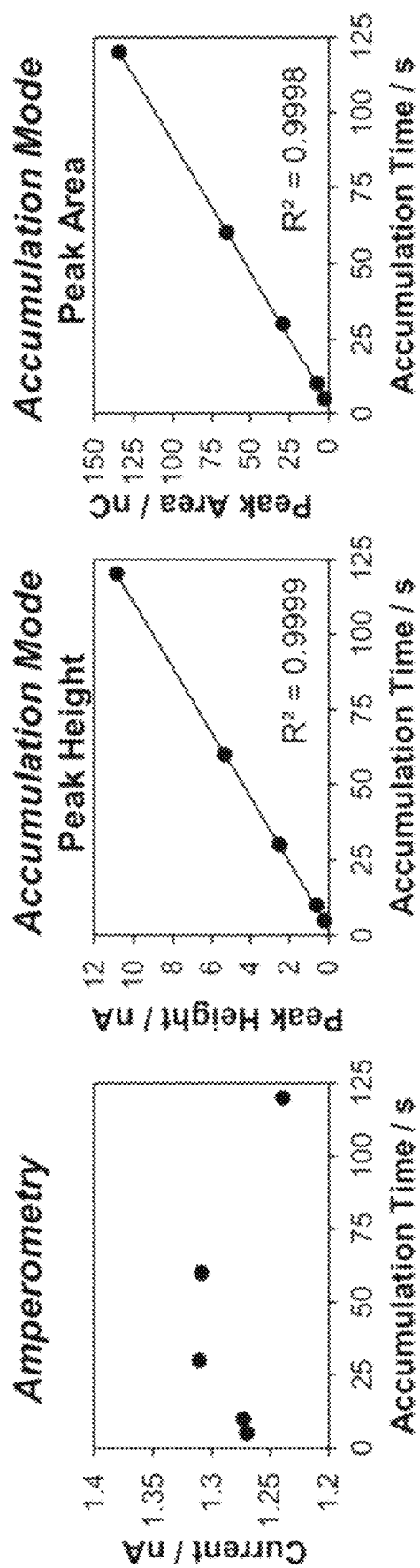
FIG. 3D shows calibration curves of the amperometry and accumulation mode signals measured by peak height or peak area for the accumulation times shown in FIG. 3C, according to embodiments of the present disclosure.

With reference to FIGS. 3C and 3D, an example of accumulation mode sensing was demonstrated using a developed glucose sensor consisting of a glucose-specific sensing reagent deposited onto a screen-printed carbon electrode. The glucose sensing reagent consists of glucose oxidase enzyme cross-linked to an Os-redox polymer. This reagent has already been demonstrated for use in glucose biofuel cells as well as both self-powered and potentiostat-powered, continuous glucose sensors. See, e.g., Mao et al., *J. Am. Chem. Soc.* 2003, 125:4951-4957; Mano et al., *J. Am. Chem. Soc.* 2003, 125:6588-6594; Liu et al., *Anal. Chem.* 2012, 84:3403-3409; Feldman et al., *Diabetes Technol. Ther.* 2003, 5:769-779; Hoss et al., *J. Diabetes Sci. Technol.* 2013, 7:1210-1219; and Hoss et al., *J. Diabetes Sci. Technol.* 2014, 8:89-94, the entire contents of all of which are herein incorporated by reference. In some embodiments of the present disclosure, a method of accumulation mode sensing may be used to increase the sensitivity of an electrochemical measurement. For the experiment shown in FIGS. 3C and 3D, a glucose sensor was placed in a solution of 2 μM glucose and 100 mM phosphate-buffered saline (PBS) and several accumulation mode measurements were made while the sensor current was monitored. For each measurement, the sensor was initially poised at +40 mV to drive steady-state glucose oxidation, then the working electrode was electrically disconnected for a set period of time (the accumulation time) to allow for charge accumulation, and then the working electrode was reconnected to measure the accumulated charge. As shown, the size of the oxidative current spike increases with an increasing accumulation time. Accordingly, by simply increasing the accumulation time (e.g., up to 30 seconds, 60 seconds, or up to 120 seconds), the sensitivity of the measurement with this glucose sensor and concentration of glucose is increased. The amperometric signal, which was measured as the steady-state sensor current, as well as the peak height and peak area of the current spikes measured in FIG. 3C are plotted relative to accumulation time in FIG. 3D. As shown, the amperometric current is not dependent on accumulation time and remains constant. However, both the height and the area of the current spike show a linear dependence upon accumulation time, highlighting the advantage accumulation mode sensing has over traditional amperometry. That is, the sensitivity of the sensor may be tuned by altering an easily adjustable parameter of the measurement technique, for example, the period of time for accumulation charge.

Figure 4A:
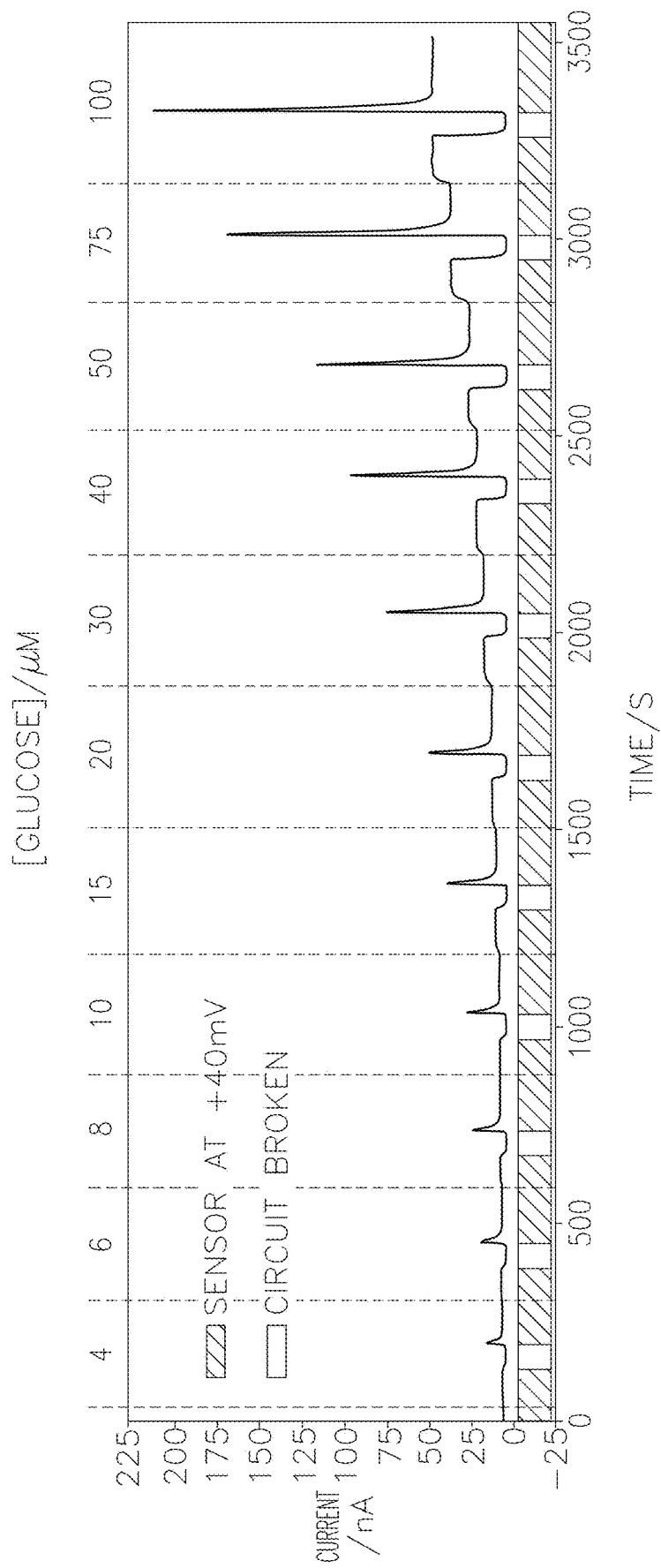
FIG. 4A shows a representative current vs. time trace for a calibration experiment using accumulation mode sensing with an example glucose sensor (at +40 mV as indicated with hatched lines and a 60 second accumulation time (when circuit is broken as indicated in white) for each detection, according to embodiments of the present disclosure.
Figure 4B:
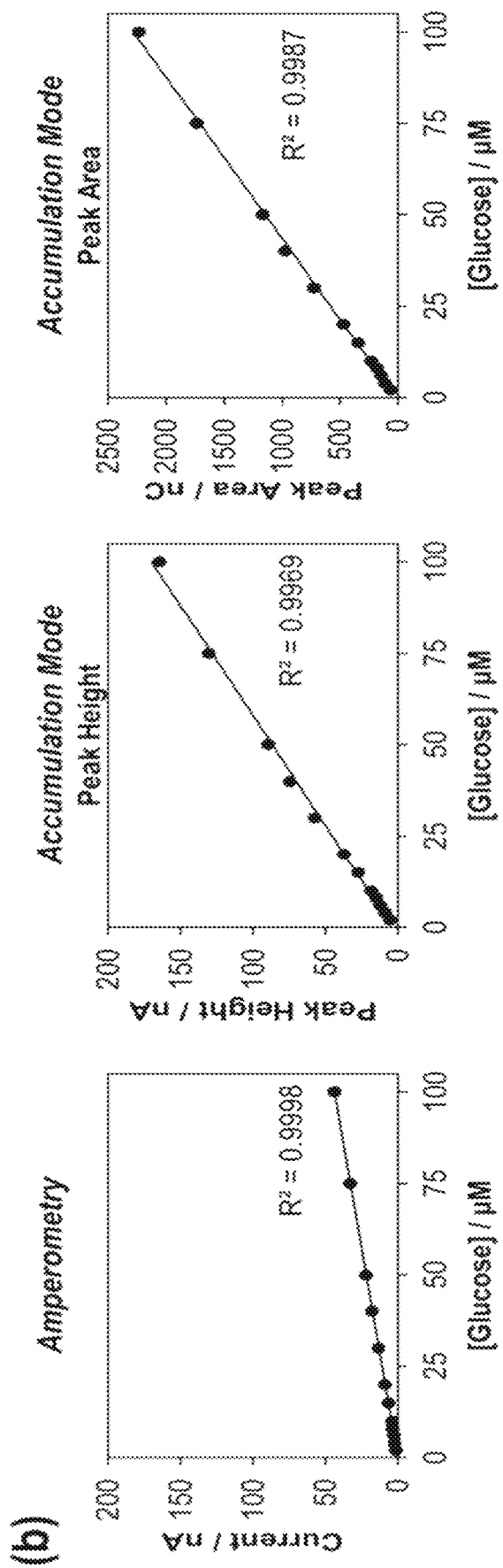
FIG. 4B shows a comparison of calibration curves resulting from the amperometry and accumulation mode signals measured for the sensing experiment shown in FIG. 4A, according to embodiments of the present disclosure.

According to embodiments of the present disclosure, the accumulation mode sensing method provides a signal over a range of analyte concentrations. FIGS. 4A and 4B show an example of a calibration experiment using an example glucose sensor for glucose concentrations up to 100 μM. As indicated, a 60 second accumulation time was used for each detection. FIG. 4A shows the resulting trace of current relative to time for this experiment. As shown, both the steady-state amperometric current and the size of the accumulation mode current peaks increase with an increasing glucose concentration. FIG. 4B shows plots of the amperometric current and the peak height and peak area of the current spikes as a function of glucose concentration, with all three signals exhibiting a linear dependence upon analyte concentration. Accordingly, the results show that accumulation mode sensing whether measured using the peak height or the area of the peak, yields linear calibration curves and therefore, may be utilized for sensing in a manner analogous to traditional amperometry with increased sensitivity. As such, since the peak height obtained from accumulation mode sensing is measured in units of current, the sensitivity of this measurement method may be quantitatively compared to the sensitivity of amperometry. For example, the sensitivity of the measurement method may be done by comparing the slopes of the calibration curves, such as those shown in FIG. 4B. By comparison, amperometry has a sensitivity of 0.44 nA/µM, while accumulation mode sensing (using the peak height measurement) has a sensitivity of 1.69 nA/µM. Therefore, with an accumulation time of 60 seconds, the accumulation mode sensing according to embodiments of the present disclosure increases the sensitivity of the electrochemical measurement by a factor of approximately 4 compared to amperometry.

Furthermore, as both the peak height and the area of the peak provide the same result and sensitivity, in some embodiments of the present disclosure, a means of measuring the resulting current signal of the working electrode includes calculating the peak height and/or the peak area.

Figure 5:
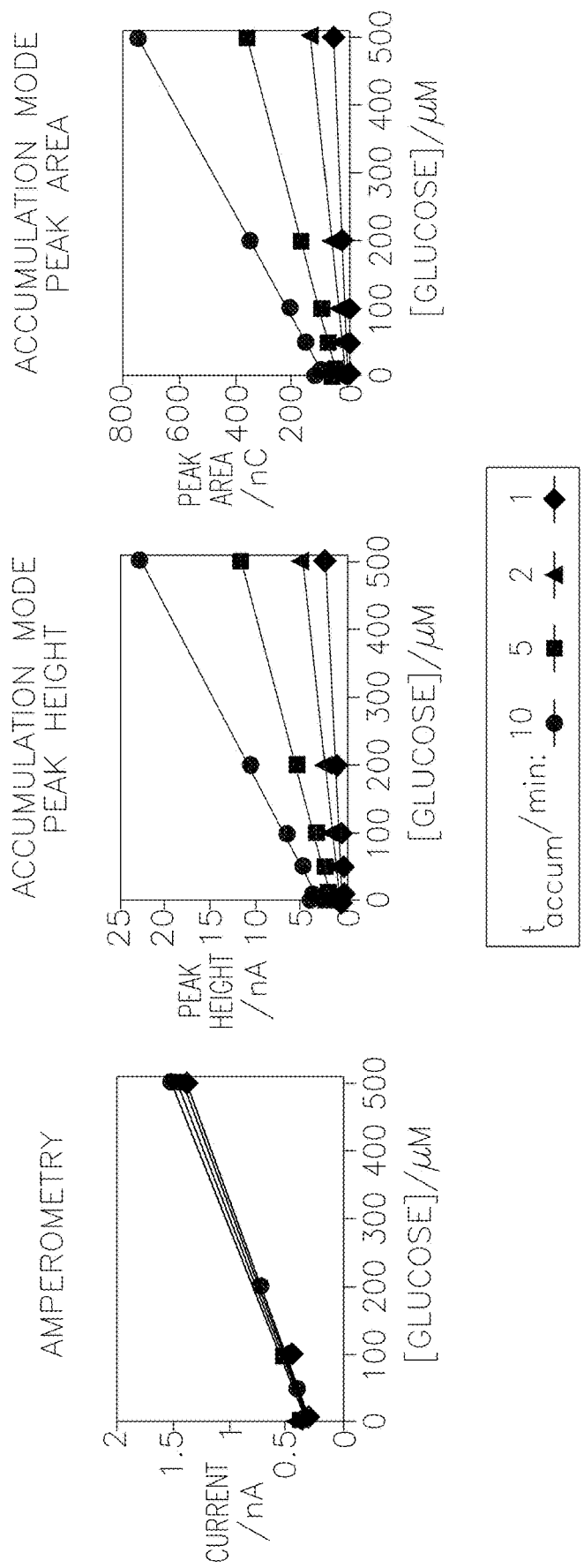
FIG. 5 shows calibration curves for amperometric and accumulation mode sensing (peak height and peak area) at 1 (diamonds), 2 (triangles), 5 (squares), and 10 (circles) minute accumulation times as indicated at glucose concentrations of 0, 50, 100, 200, and 500 µM, with each calibration curve representing the average response of four sensors, according to embodiments of the present disclosure.

In some embodiments of the present disclosure, accumulation mode sensing is carried out using a sensor having an outer membrane. As electrochemical sensors are often times coated with an outer membrane (e.g., a polymer membrane) in order to provide stability to the sensing reagents, mass-transport limitations, biocompatibility, and/or to prevent electrode fouling, a polymer-coated sensor was tested to ensure that accumulation mode sensing performs as expected. With reference to FIG. 5, an example glucose sensor coated with a flux-limiting outer polymer membrane was used to obtain calibration curves via amperometry and accumulation mode sensing at glucose concentrations of 0, 50, 100, 200, and 500 µM. Four consecutive measurements were made at each glucose concentration using a different accumulation time of 1, 2, 5, and 10 minutes as indicated with the data points, respectively, in FIG. 5.

As shown in FIG. 5, both the amperometry (left graph) and the accumulation mode measurements (middle and right graphs) give a linear response to analyte concentration. As expected, using amperometry (left graph of FIG. 5), the sensitivity of the sensor is independent of the accumulation time. However, using the accumulation mode sensing (middle and right graphs of FIG. 5), sensor sensitivity increases with an increase in the accumulation time. Due to the flux-limiting outer membrane, the sensor sensitivities using both amperometric and accumulation mode sensing are much smaller than for sensors without an outer membrane. This is expected, as the outer membrane limits diffusion of the analyte to the sensing reagent. However, as shown in FIG. 5, accumulation mode sensing performs as expected when an outer polymer membrane is added to the sensor and gives another example of how the sensitivity of the sensor may be tuned by altering the accumulation time. Furthermore, it is noted that a set period of time greater than 10 minutes for accumulation of charge using the accumulation mode sensing with continuously monitoring sensors may cause negative effects on the time resolution of the sensor. Accordingly, in some embodiments of the present disclosure, accumulation mode sensing is carried out using a sensor having an outer membrane where the set period of time for accumulation of charge is up to 10 minutes.

It is further noted that while an outer membrane such as a flux-limiting outer membrane may not be necessary to prevent electrode fouling when measuring analytes at low concentrations, an outer membrane may provide a biocompatible interface with an in vivo environment and/or provide stability to the underlying sensing layer including the electron transfer agents and/or analyte-specific enzymes thereon. For accumulation mode sensing in which an outer membrane is used, the set period of time for accumulating charge may be increased to allow for oxidation of the total analyte concentration. In some embodiments of the present disclosure, a method of accumulation mode sensing using a sensor having an outer membrane includes increasing the set period of time for accumulating charge up to 1 minute, up to 2 minutes, up to 3 minutes, up to 4 minutes, up to 5 minutes, up to 6 minutes, up to 7 minutes, up to 8 minutes, up to 9 minutes, or up to 10 minutes in order to allow for complete reaction of all of the analyte present at the working electrode. In some embodiments of the present disclosure, a method of accumulation mode sensing using a sensor having an outer membrane includes increasing the set period of time for accumulating charge from 10 minutes up to 30 minutes.

Alternatively, in some embodiments of the present disclosure, the outer membrane may be made of a highly permeable material and thus, while the permeable membrane does not attenuate the rate at which the analyte reaches the sensing layer of the working electrode, the permeable membrane allows for stability, mass-transport limitations, and/or biocompatibility. Non-limiting examples of highly permeable membrane materials, include poly(vinyl pyridine) crosslinked with high molecular weight (MW≥400 g/mol) poly(ethylene glycol) diglycidyl ether, derivatized poly(vinyl pyridine) crosslinked with high molecular weight (MW 400 g/mol) poly(ethylene glycol) diglycidyl ether, poly(vinyl alcohol), poly(acrylic acid), and poly(methacrylic acid).

Figure 6A:
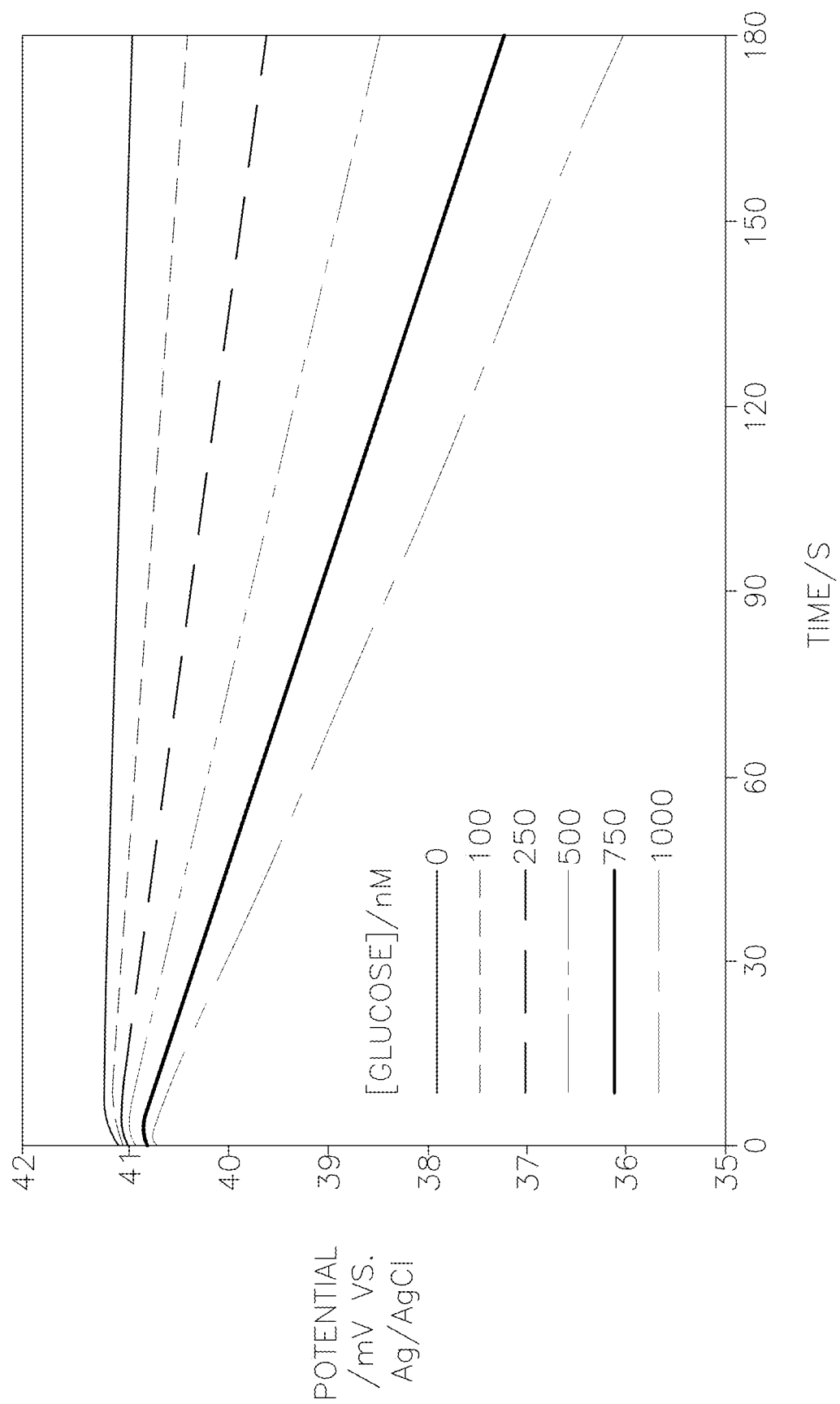
FIG. 6A shows a graph of potential versus time signal of a model glucose sensor obtained using the open circuit potential method for sensing various nanomolar (nM) concentrations of glucose as indicated, according to embodiments of the present disclosure.
Figure 6B:
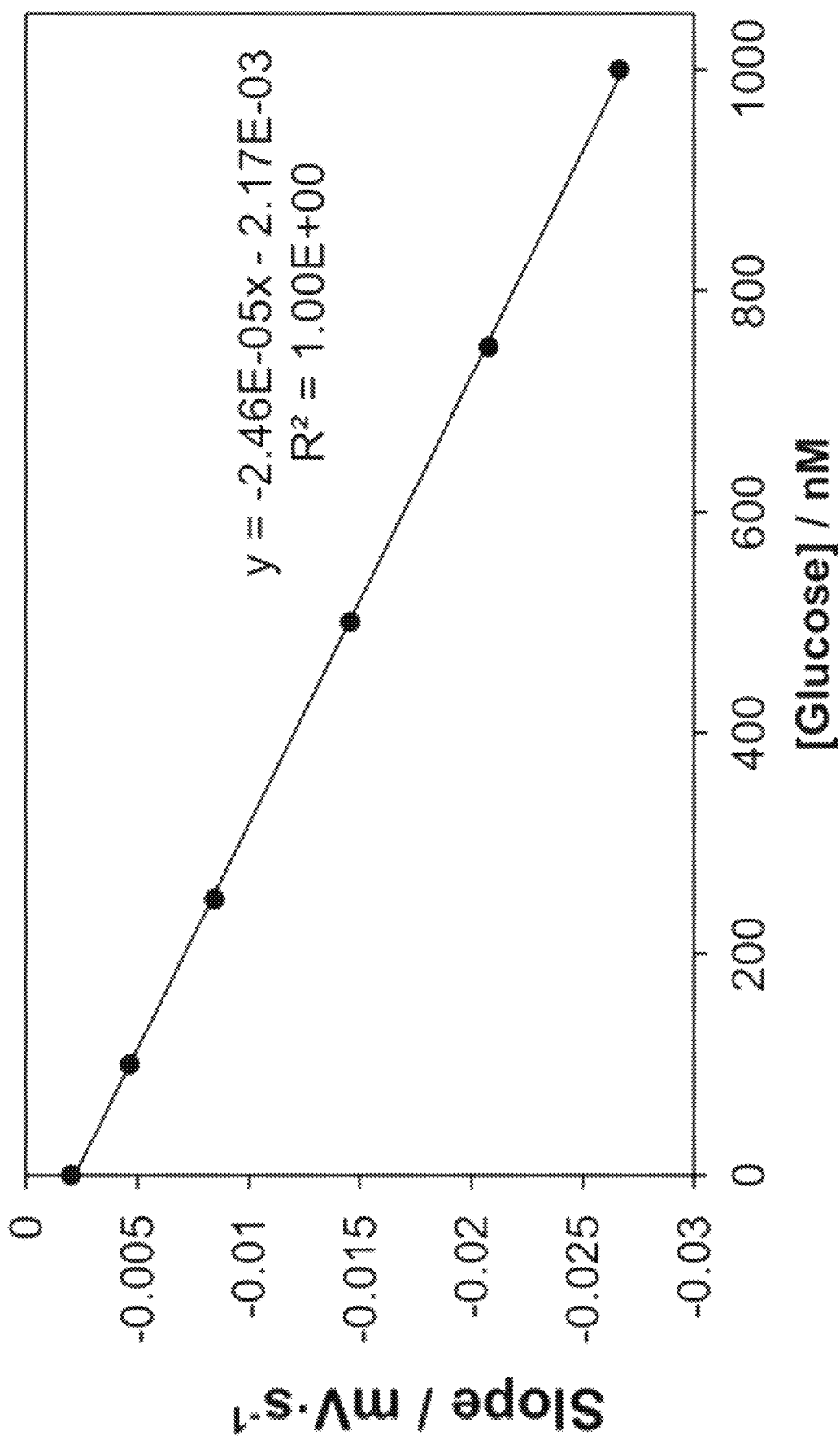
FIG. 6B shows a calibration curve (slope versus concentration of glucose (nM)) of the graph data of FIG. 6A, according to embodiments of the present disclosure.

With reference to FIGS. 6A-6B, an electrochemical glucose sensor was used in an in vitro experiment to measure (e.g., sense) concentrations of glucose ranging from 0 to 1000 nanomolar (nM) glucose. In this example, the working electrode of the sensor included glucose oxidase enzyme cross-linked to an Os-based redox polymer deposited and immobilized onto a screen-printed carbon electrode. The experiment was carried out as disclosed herein (e.g., Example 8). Additionally, a screen-printed carbon counter electrode and a Ag/AgCl reference electrode were used. Before each measurement, the working electrode was held at +40 mV versus (vs.) Ag/AgCl for 3 minutes, after which point the open circuit potential of the electrode was measured for 3 minutes. The graph in FIG. 6A shows the resulting potential versus time traces for the indicated glucose concentrations (from 0 to 1000 nM glucose). Accordingly, as shown, higher glucose concentrations results in a greater magnitude potential drift rate. In some embodiments of the present disclosure, the drift rate is calculated as the slope of the potential versus time traces. FIG. 6B is a calibration curve showing a plot of the drift rate (calculated as the slope from 30 to 180 seconds) versus glucose concentration. As shown in FIG. 6B, the potential drift rate shows a linear dependence on glucose concentration.

Figure 6C:
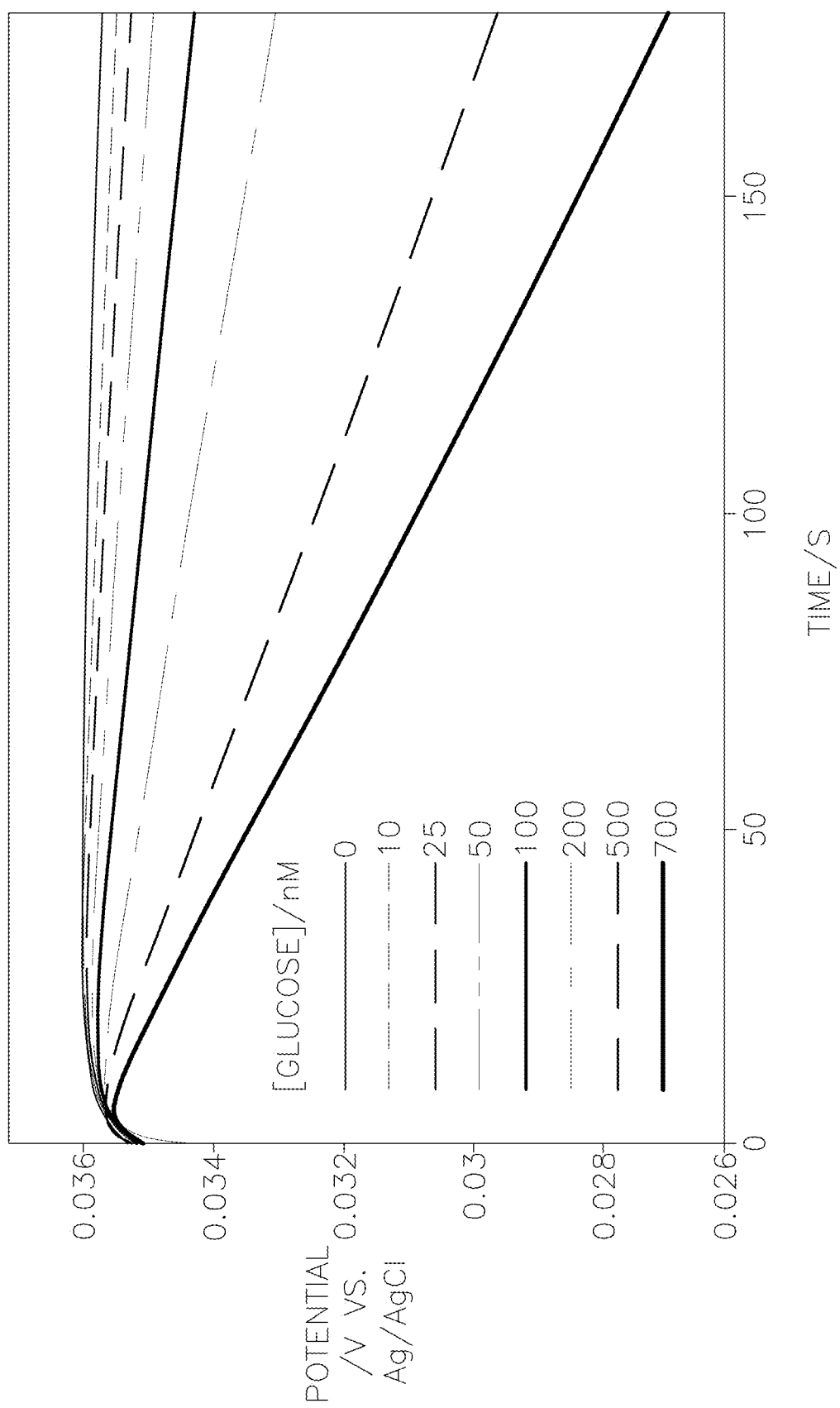
FIG. 6C shows a graph of potential versus time signal of a model glucose sensor obtained using the open circuit potential method for sensing various nM concentrations of glucose as indicated, according to embodiments of the present disclosure.
Figure 6D:
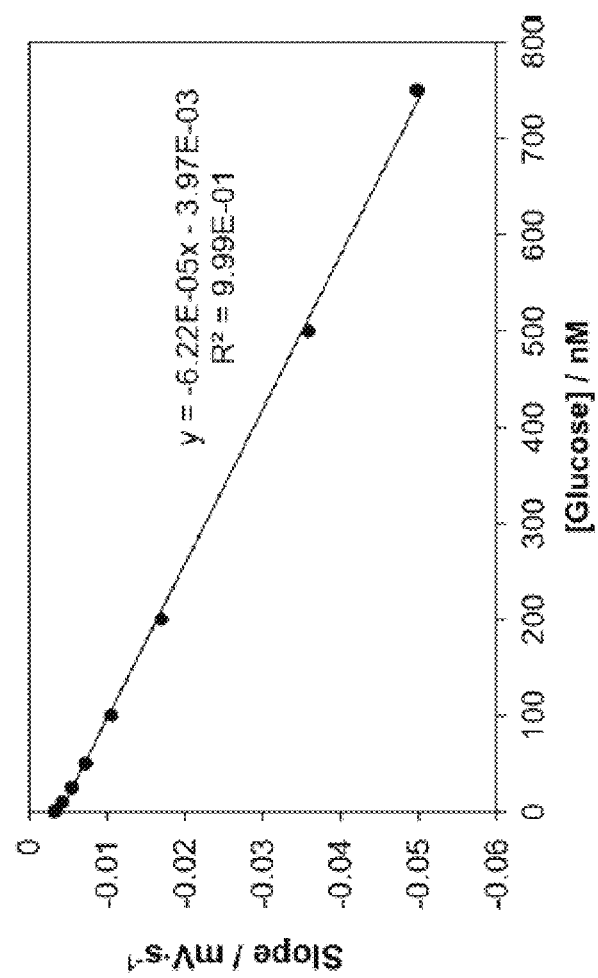
FIG. 6D shows a calibration curve (slope versus concentration of glucose (nM)) of the graph data of FIG. 6C, according to embodiments of the present disclosure.
Figure 6E:
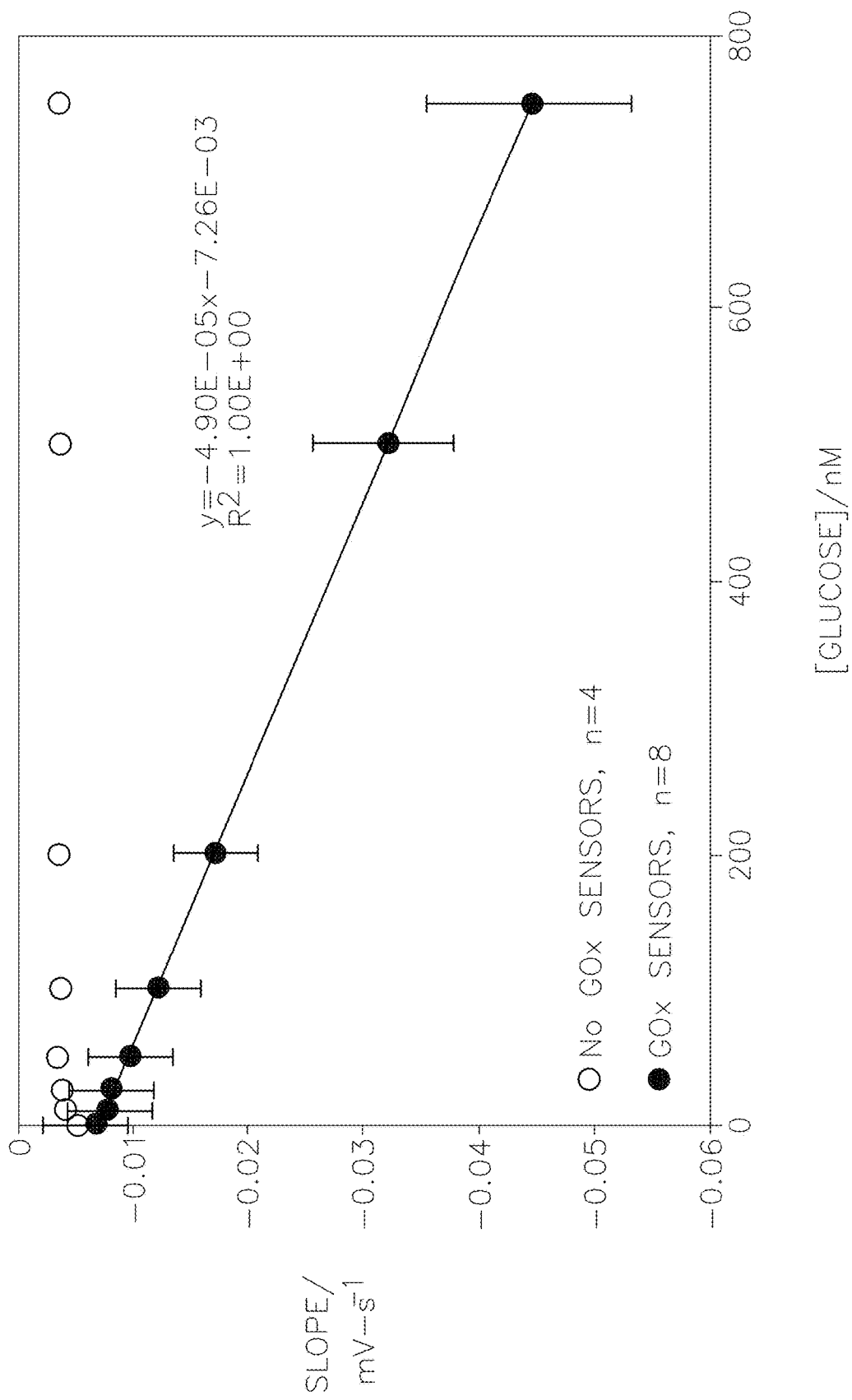
FIG. 6E shows a composite calibration curve for model glucose sensors (solid circle data points, n=8) and control sensors (open circle data points, n=4) from in vitro sensing of glucose using the open circuit potential method, according to embodiments of the present disclosure.
Figure 6F:
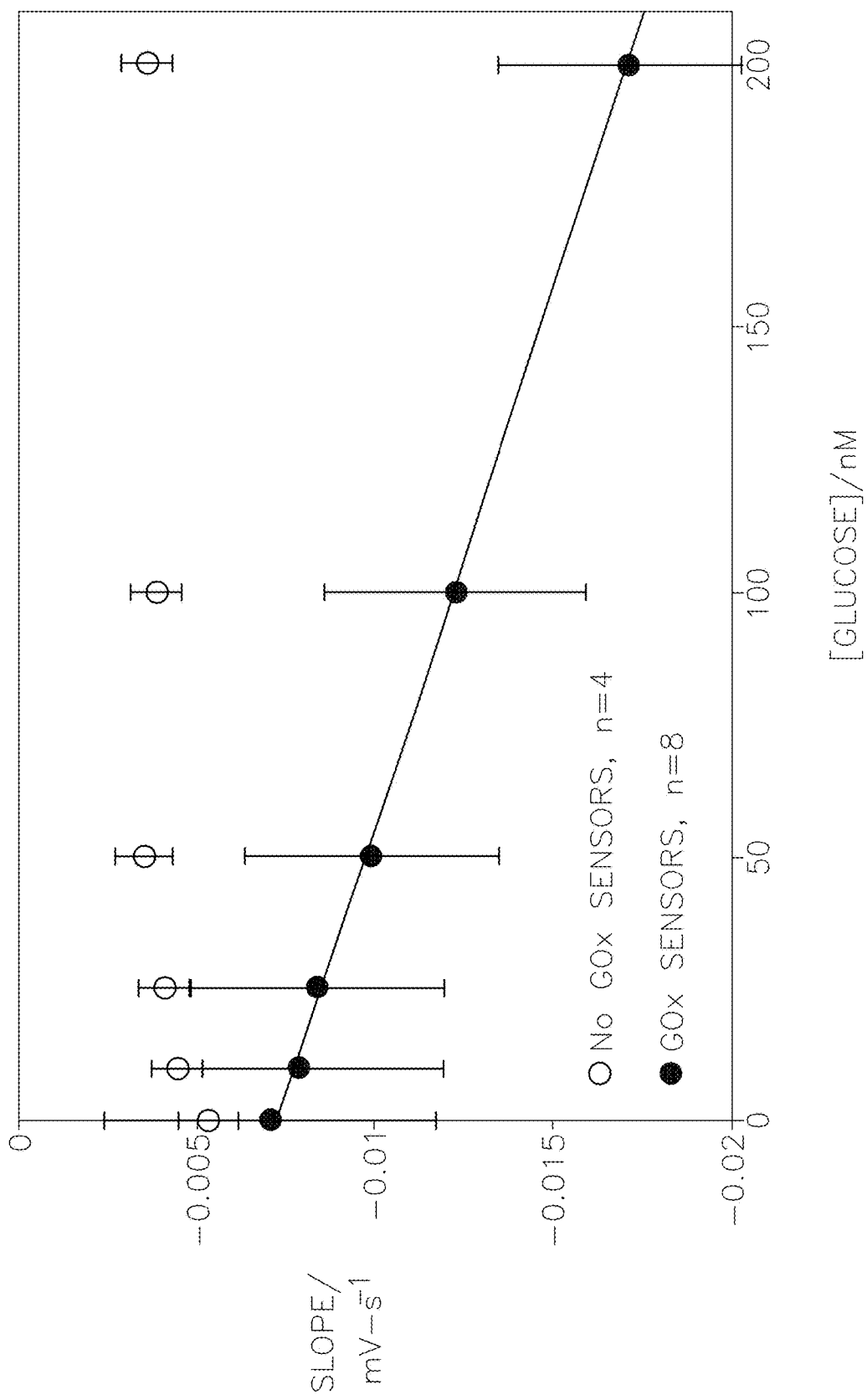
FIG. 6F shows a zoom-in of the calibration curve of FIG. 6E from 0 to 200 nM glucose, according to embodiments of the present disclosure.

With reference to FIGS. 6C-6D, the same electrochemical glucose sensor used in the experiment of FIGS. 6A-6B was used in an in vitro experiment to measure concentrations of glucose ranging from 0 to 750 nM glucose including glucose concentrations below 100 nM (e.g., 10 nM, 25 nM, and 50 nM). The graph in FIG. 6C shows the resulting potential versus time traces for the indicated glucose concentrations. Accordingly, as shown in FIG. 6D, the plotted drift rate for this experiment remains linear down to 10 nM glucose. This correlation is further shown in FIG. 6E showing a calibration curve resulting from the testing of 8 individual glucose sensors. Additionally, control sensors lacking glucose oxidase enzyme (but still possessing Os redox polymer) were also tested in this experiment. As shown in FIGS. 6E and 6F, the drift rate of the control sensors represented by the open circles showed no dependence on glucose concentrations.

Figure 6G:
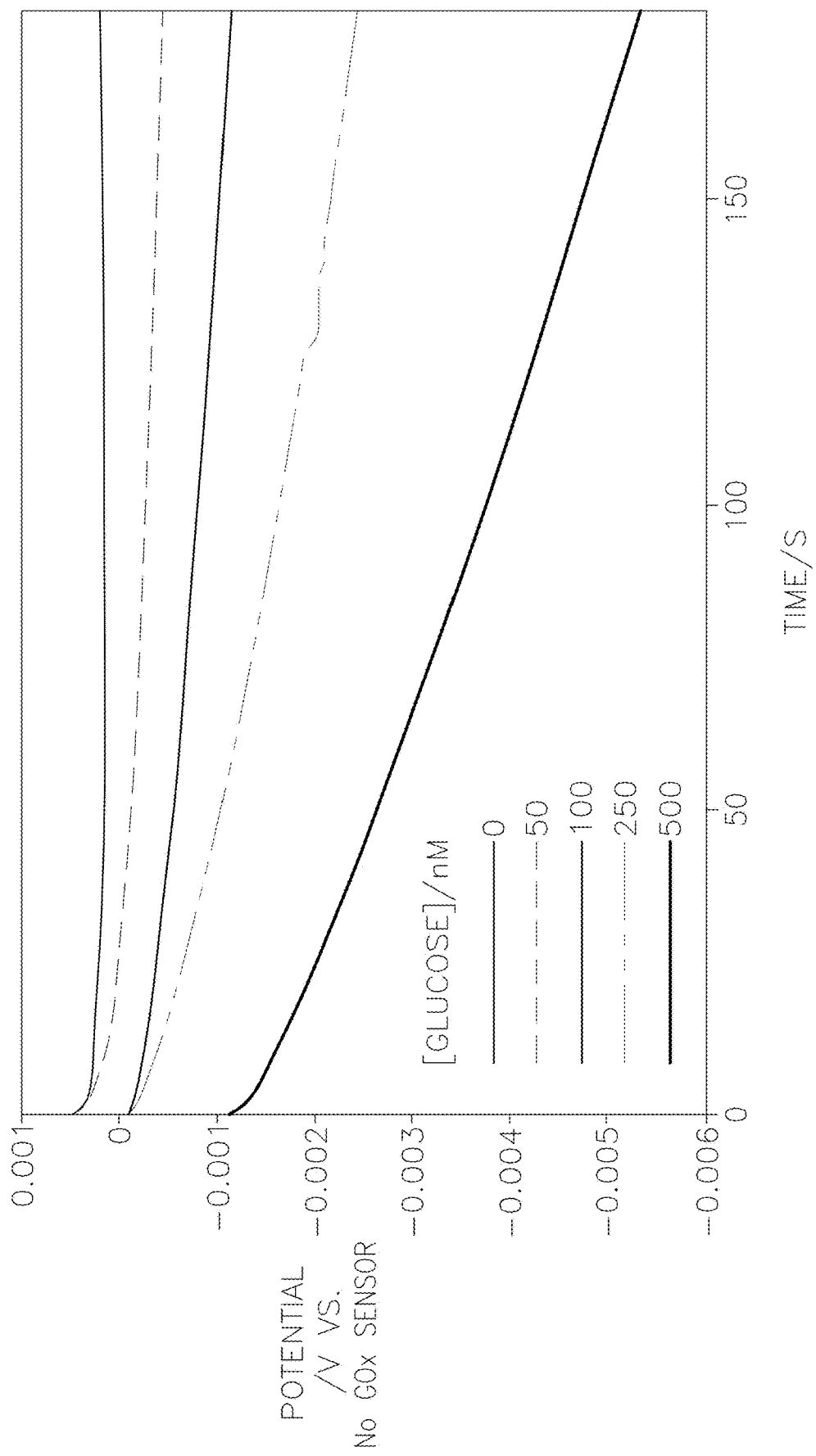
FIG. 6G shows a graph of potential versus time signal of a model glucose sensor obtained using the open circuit potential method with a model glucose sensor as the working electrode and a control sensor (possessing redox polymer but no glucose oxidase) as the reference electrode, the model glucose sensor for sensing various nM concentrations of glucose as indicated, according to embodiments of the present disclosure.
Figure 6H:
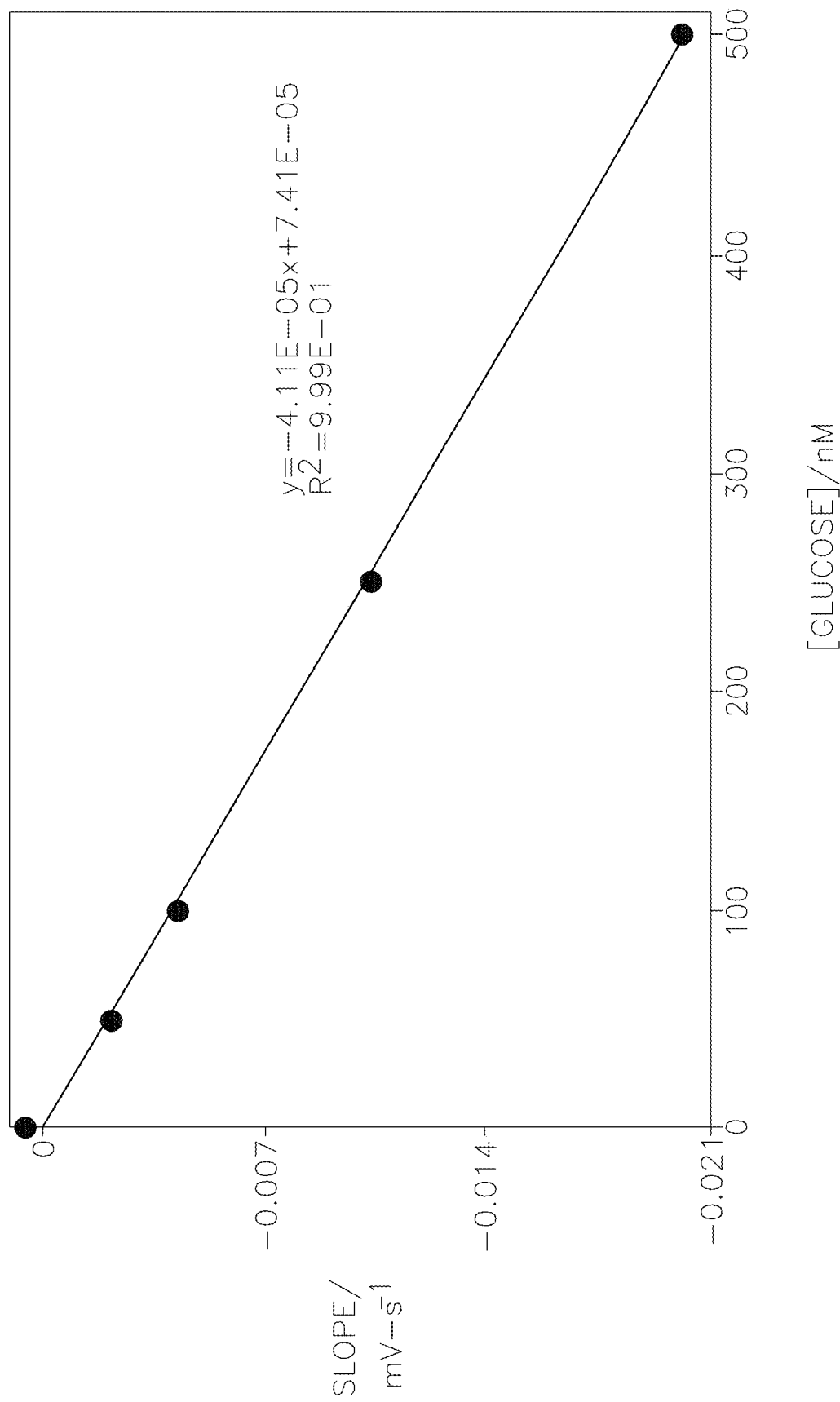
FIG. 6H shows a calibration curve (slope versus concentration of glucose (nM)) of the graph data of FIG. 6G, according to embodiments of the present disclosure.

According to some embodiments of the present disclosure, the presently disclosed method may be used to lower background signal (e.g., signal at [analyte]=0). With reference to FIGS. 6G-6H, an experiment was performed using the glucose sensor used in the experiment shown in FIG. 6A as the working electrode. Additionally, a control sensor lacking glucose oxidase enzyme but still possessing Os redox polymer was used as the reference electrode during the open circuit potential measurement. Using this configuration, the amount of signal measured that is not from glucose oxidation is minimized. For example, when utilizing a no-glucose oxidase control sensor as the reference electrode, the background signal (the slope of the potential versus time trace for a glucose concentration of zero is approximately zero. The resulting intercept of the calibration curve shown in FIG. 6H is two orders of magnitude smaller than the intercept of the calibration curve shown in FIG. 6F, which was obtained using a Ag/AgCl reference electrode. Accordingly, methods and systems of the present disclosure include using a no-glucose oxidase control sensor as a reference electrode during the open circuit potential measurement as an effective method for lowering the signal background.

Figure 7:
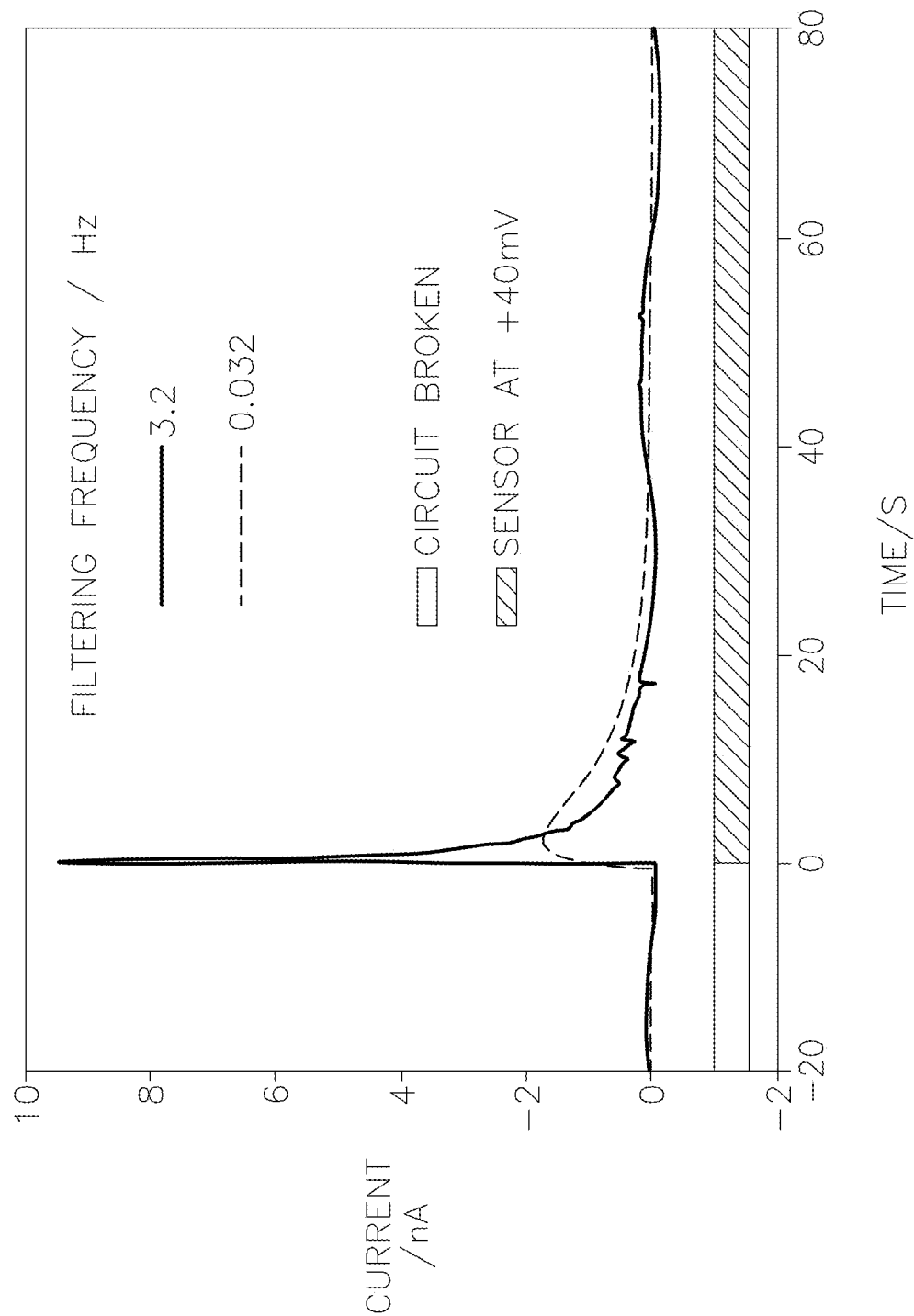
FIG. 7 shows a comparison of accumulation mode signal shape under different filtering frequencies with 3.2 Hz shown with a solidblack lineand 0.032 Hz shown with a dashed line, according to embodiments of the present disclosure.

In some embodiments of the present disclosure, a signal produced from the redox reaction of an analyte at the sensing layer of a working electrode may be tuned or modified to enhance the signal output for any given sensor and/or analyte concentration. In some embodiments of the present disclosure, the signal is enhanced by modifying the frequency at which the current signal is recorded. For example, with reference to FIG. 7, in order to maximize the peak height measured during the accumulation detection current spike, the signal may be recorded at a faster sampling rate (e.g., 0.1 Hz) and filtered at a higher frequency (e.g., 3.2 Hz) than the sampling rate of 0.5 Hz sampling rate and a frequency of 0.03 Hz filter which were used for the accumulation mode sensing experiments disclosed herein and shown in FIGS. 3A-3D, 4A-4B, and 5. As shown in FIG. 7, the detection peak is much sharper at the higher frequency of 3.2 Hz, leading to a larger peak height. Accordingly, in some embodiments of the present disclosure, the accumulation mode sensing method includes increasing the frequency filter up to 3.2 Hz for maximizing the signal magnitude. It is noted that at a frequency higher than 3.2 Hz, the signal to noise ratio is too large to allow for accurate measurements whether using amperometric current or the accumulation peak measurement.

Figure 8A:
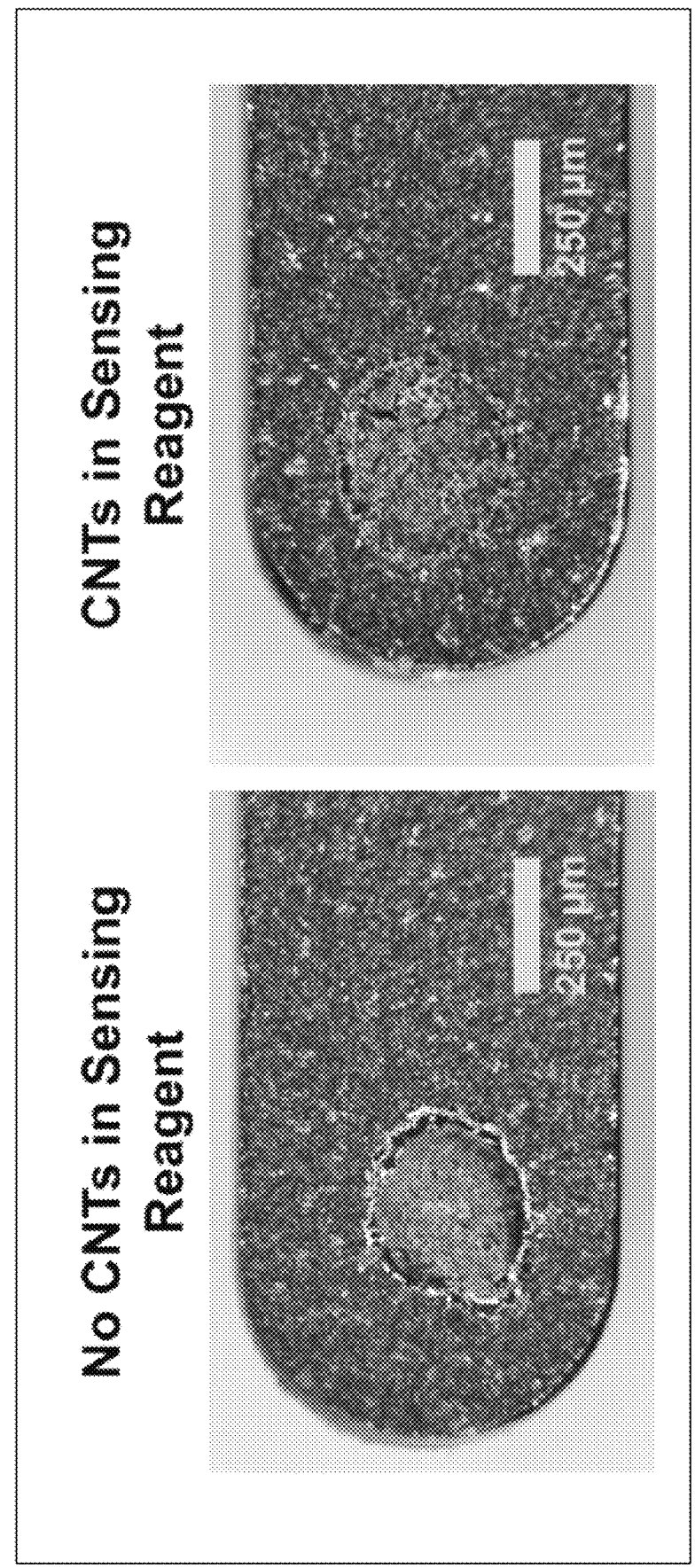
FIG. 8A shows two micrographs of the deposited glucose sensing reagent with (right panel) and without (left panel) carbon nanotubes, CNTs, according to embodiments of the present disclosure.
Figure 8B:
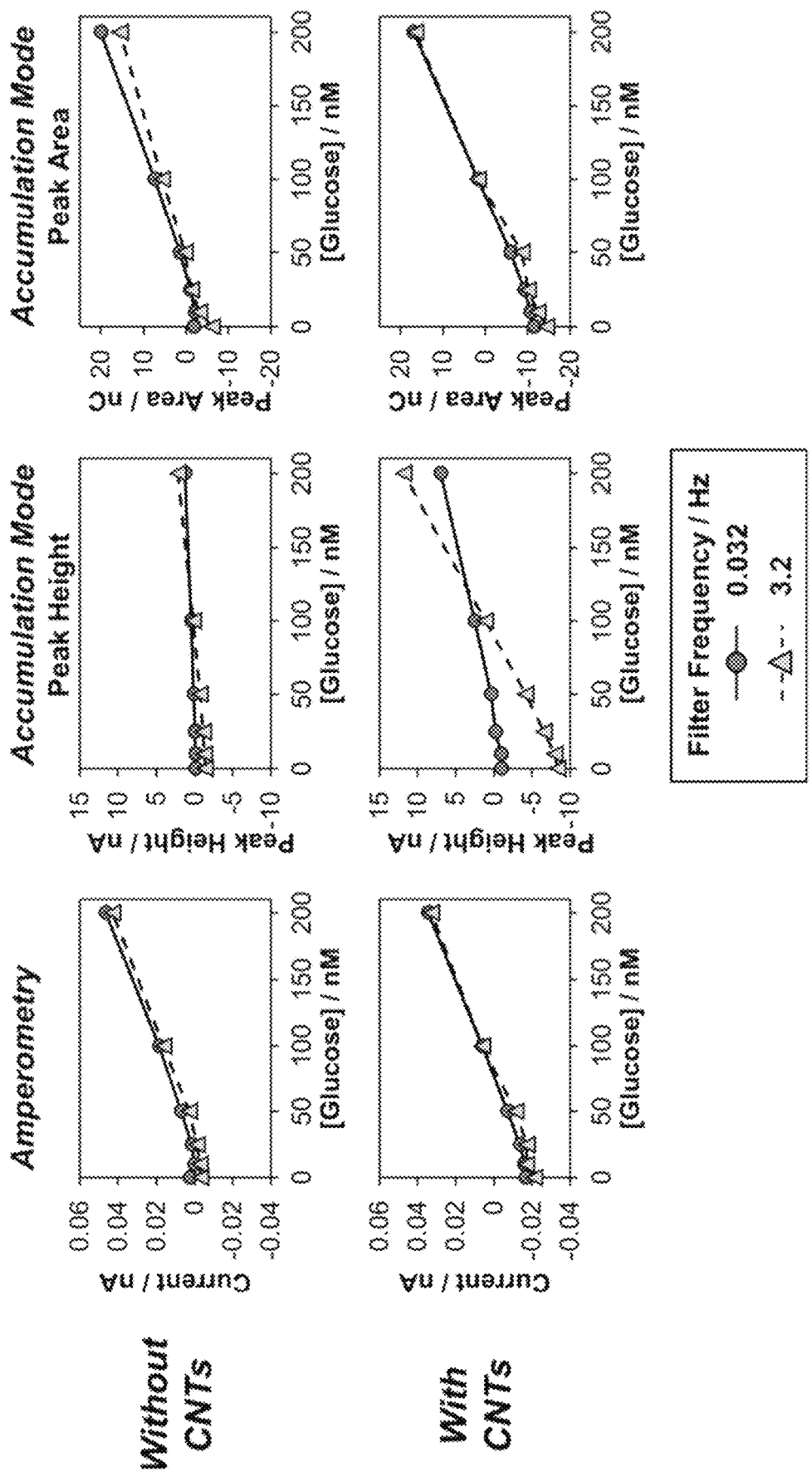
FIG. 8B shows calibration curves for amperometric and accumulation mode detection (peak height and peak area) using different filtering frequencies (0.032 Hz shown as circles and 3.2 Hz as triangles) and sensing reagent with and without CNTs, according to embodiments of the present disclosure.

In some embodiments of the present disclosure, carbon nanotubes (CNTs) are added to the sensing element of the working electrode. For example, the CNTs are added to the sensing reagent including the redox mediator and analyte-specific enzyme and applied to the working electrode. With reference to FIG. 8A, CNTs were added to the sensing reagent in the micrograph on the right and CNTs were not added in the micrograph on the left. The accumulation mode sensing was measured with and without CNTs. As shown in FIG. 8B, with the addition of CNTs with the sensing element on the working electrode, the accumulation mode current spike has a larger peak height.

Figure 9A:
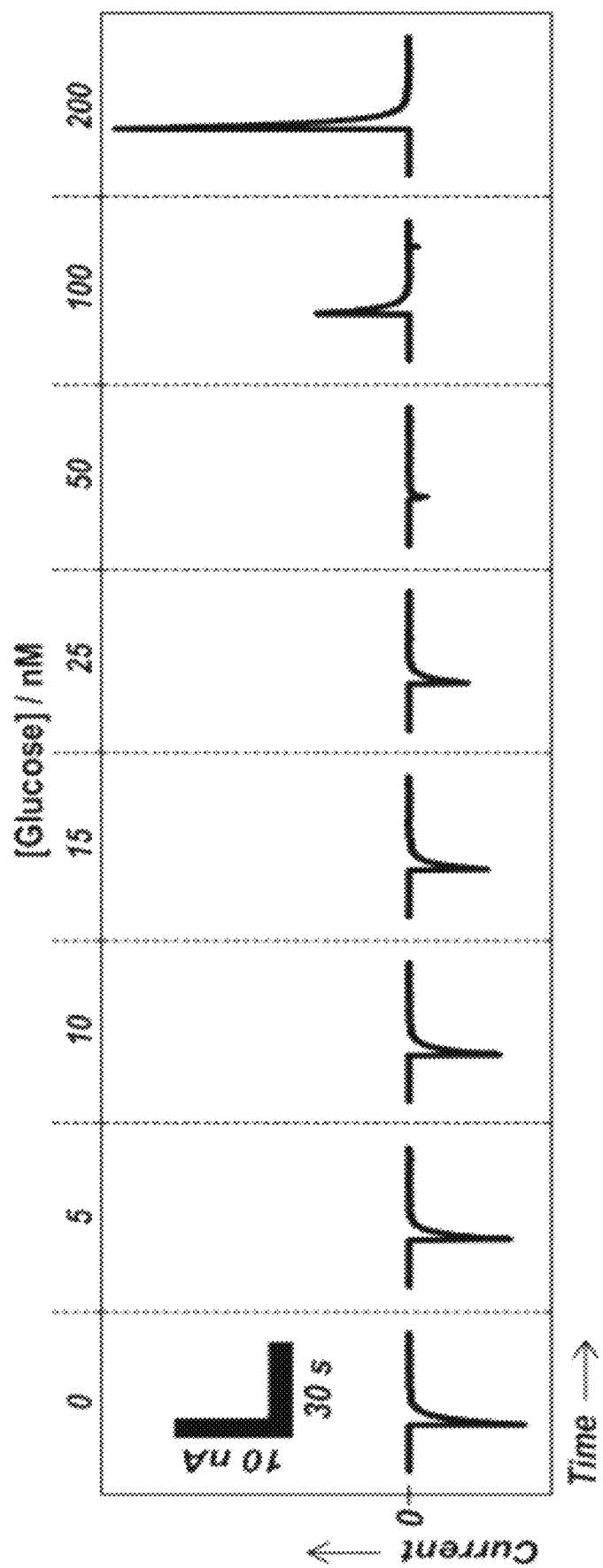
FIG. 9A shows accumulation mode signals obtained for a representative glucose sensor during a calibration experiment using glucose concentrations from 0 to 200 nM, with a 30 minute accumulation time for each detection, a signal filtered at 3.2 Hz, and CNTs added to the sensing reagent, according to embodiments of the present disclosure

In some embodiments of the present disclosure, accumulation mode sensing includes using a sensor with an accumulation time (e.g., a set period of time for accumulation of charge) of 30 minutes, a signal frequency filter at 3.2 Hz, and the addition of carbon nanotubes (CNTs) to the sensing element on the working electrode. FIG. 9A shows the accumulation mode signals obtained for a representative glucose sensor at glucose concentrations from 0 to 200 nM in the presence of CNTs, with a 30 minute accumulation time, and the signal filtered at 3.2 Hz. Accordingly, as shown in the signal calibration curves of FIG. 9B, in comparison with amperometry, accumulation mode sensing according to embodiments of the present disclosure provide increased sensitivity for low concentration analytes. As seen, with an accumulation time of 30 minutes, accumulation mode sensing using the peak height measurement gives an 800-fold increase in sensitivity over amperometry. With respect to detection limit, accumulation mode sensing using the peak area measurement is superior, resulting in a lower limit of detection (LOD) of 4.7±1.4 nM, a 25-fold improvement over amperometry. While the linear range for accumulation mode sensing is more limited than for amperometry, it should be noted that this range may be shifted to higher concentrations by using a shorter accumulation time.

Sensor for Accumulation Mode Sensing

A sensor as described herein may be an in vivo sensor or an in vitro sensor (i.e., a discrete monitoring test strip). Such a sensor may be formed on a substrate, e.g., a substantially planar substrate. In certain embodiments, the sensor is a wire, e.g., a working electrode wire inner portion with one or more other electrodes associated (e.g., on, including wrapped around) therewith. The sensor may also include at least one counter electrode (or counter/reference electrode) and/or at least one reference electrode or at least one reference/counter electrode.

Figure 12:
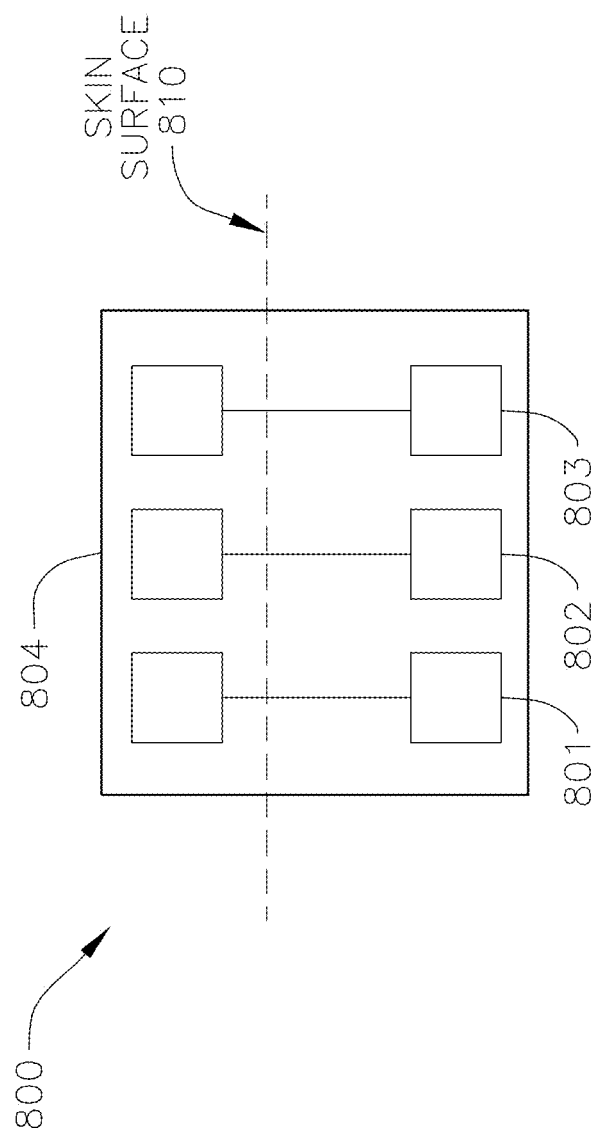
FIG. 12 shows a schematic diagram of an analyte sensor according to embodiments of the present disclosure.

FIG. 12 schematically depicts an embodiment of an analyte sensor 800 in accordance with the embodiments of the present disclosure. This sensor includes electrodes 801, 802, and 803 on a base 804. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The analyte sensor 800 may be wholly implantable in a user or may be configured so that only a portion is positioned within (internal) a user and another portion outside (external) a user. For example, the sensor 800 may include a first portion positionable above a surface of the skin 810, and a second portion positioned below the surface of the skin. In such embodiments, the external portion may include contacts (connected to respective electrodes of the second portion by traces) to connect to another device also external to the user such as a transmitter unit. While the embodiment of FIG. 12 shows three electrodes 801, 802, and 803 side-by-side on the same surface of base 804, other configurations are contemplated, e.g., fewer or greater electrodes, some or all electrodes on different surfaces of the base or present on another base, some or all electrodes stacked together, electrodes of differing materials and dimensions, etc.

Figure 13:
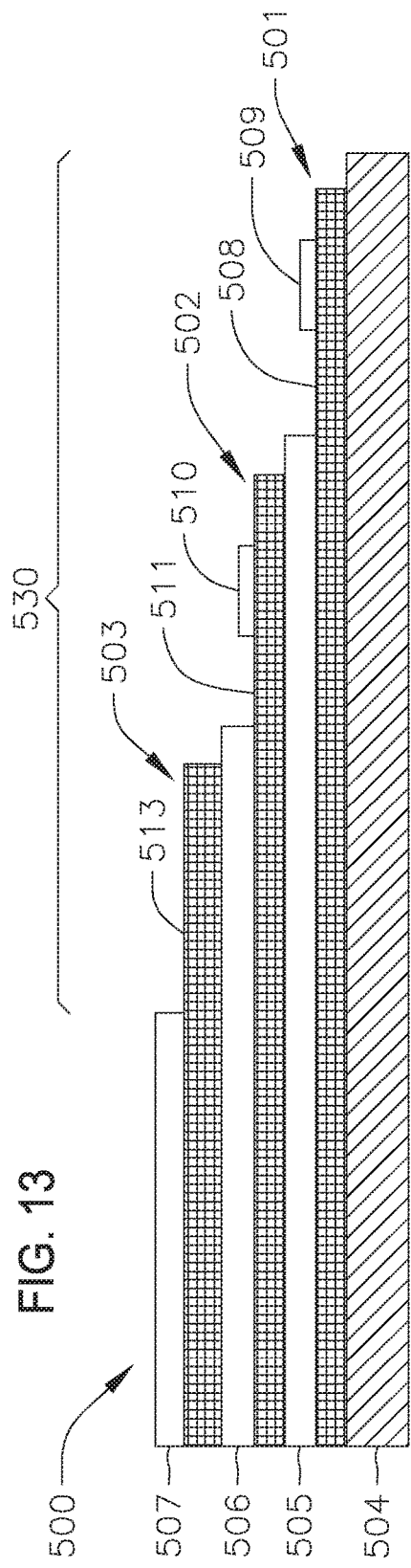
FIG. 13 is a cross-sectional view depicting a portion of an analyte sensor that is compatible with one or more embodiments of the present disclosure.

FIG. 13 shows a cross-sectional view of an embodiment of an analyte sensor 500 having a first portion (which in this embodiment may be characterized as a major portion)

positionable above a surface of the skin, and a second portion (which in this embodiment may be characterized as a minor portion) that includes a sensor tail 530 (which may also be referred to herein as an insertion tip) positionable below the surface of the skin (e.g., penetrating through the skin (dermis) and into the subcutaneous space and in contact with the wearer's biofluid, such as interstitial fluid. Electrode contacts (not shown) are positioned on the first portion of the sensor 500 situated above the skin surface and extend to a location in sensor tail 530. A working electrode 501, a reference electrode 502, and a counter electrode 503 are shown at the second portion of the sensor 500 and particularly at the bottom portion of sensor tail 530. It is to be understood that greater or fewer electrodes may be provided on a sensor, without departing from the scope of the present disclosure. For example, a sensor may include more than one working electrode and/or the counter and reference electrodes may be a single counter/reference electrode, and the like.

Referring still to FIG. 13, the sensor 500 includes a substrate (or substrate layer) 504 and a first conducting layer 508, such as carbon, gold, etc., that is in electrical communication with sensing area 509, thereby collectively defining working electrode 501. Sensing area 509 may be protected from microorganisms by providing on one or more components of the sensor 500 an antimicrobial quality, designed to protect the skin health of the wearer and/or to protect the sensing area 509 from potential interference with such microorganisms (e.g., formation of a biofilm due to potential migration of the microorganisms). The various electrodes and sensing areas defined on the bottom portion of the sensor tail 530 in FIG. 13 may be collectively a sensing region, and any such antimicrobial quality provided to the sensor tail described herein, is provided in the upper portion (upper 25%) of the sensor tail 530 above said region (e.g., above sensing area 509, or above electrode 503).

A first insulation layer 505, such as a first dielectric layer in some embodiments, may be disposed or layered on at least a portion of the first conducting layer 508, and further, a second conducting layer 511 may be disposed or stacked on top of at least a portion of the first insulation layer (or dielectric layer) 505. As shown in FIG. 13, the second conducting layer 511 in conjunction with a second conducting material 510, such as a layer of silver/silver chloride (Ag/AgCl), may provide the reference electrode 502. Another possible disposition of second conducting material 510 is shown in FIG. 14B, along with an outer membrane 520 overcoating the various layers.

A second insulation layer 506, such as a second dielectric layer in some embodiments, may be disposed or layered on at least a portion of the second conducting layer 511. Further, a third conducting layer 513 may be disposed on at least a portion of the second insulation layer 506 and may provide the counter electrode 503. Finally, a third insulation layer 507 may be disposed or layered on at least a portion of the third conducting layer 513. In this manner, the sensor 500 may be layered such that at least a portion of each of the conducting layers is separated by a respective insulation layer (e.g., a dielectric layer). Another possible layer configuration is shown in FIG. 14B. The embodiments of FIGS. 13 and 14B show the layers having different lengths; however, some or all of the layers may have the same or different lengths and/or widths, without departing from the scope of the present disclosure.

In any one or all embodiments, some or all of the electrodes 501, 502, and 503 may be provided on the same side of the substrate 504 in the layered construction described above, or alternatively, may be provided in a co-planar manner such that two or more electrodes may be positioned on the same plane (e.g., side-by side, parallel, or angled relative to each other) on the substrate 504. For example, co-planar electrodes may include a suitable spacing therebetween and/or include a dielectric material or insulation material disposed between the conducting layers/electrodes. Furthermore, in some embodiments, one or more of the electrodes 501, 502, and 503 may be disposed on opposing sides of the substrate 504. In such embodiments, contact pads may be on the same or different sides of the substrate. For example, an electrode may be on a first side and its respective contact may be on a second side, for example, a trace connecting the electrode and the contact may traverse through the substrate.

Figure 14A:
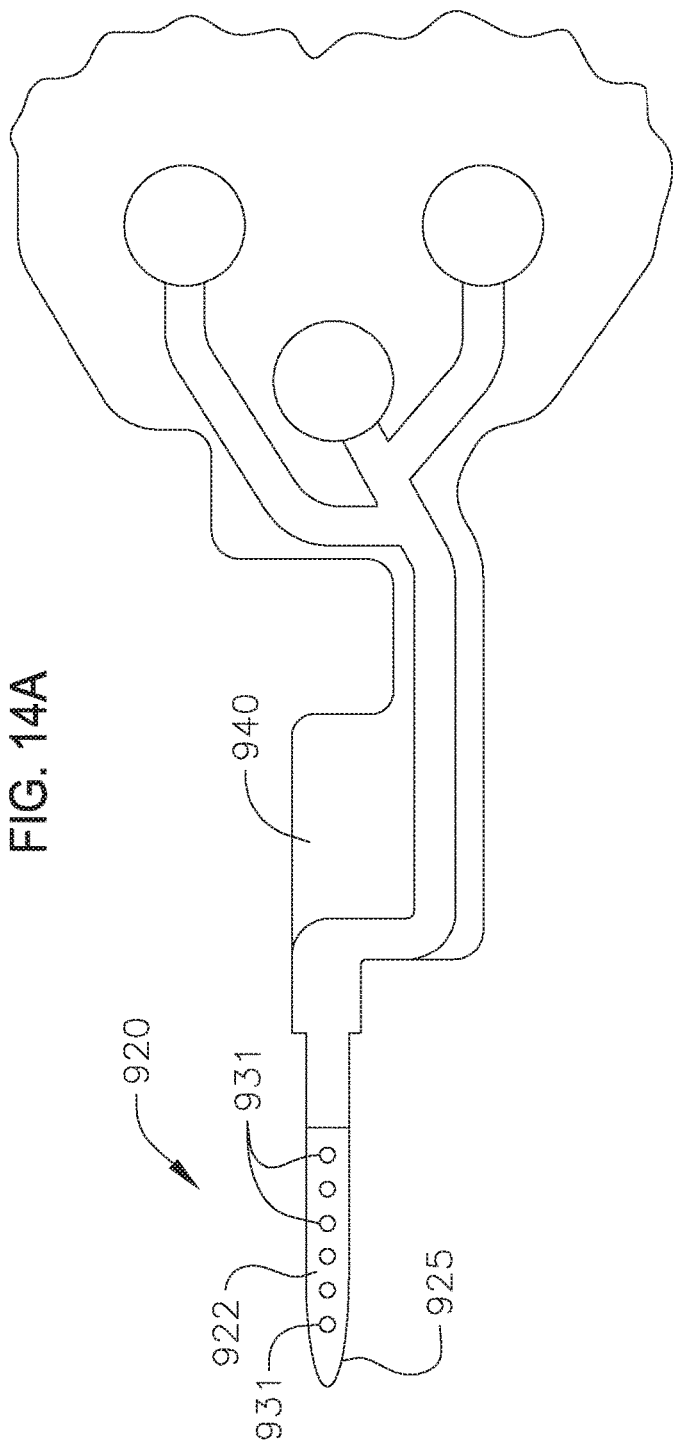
FIG. 14A shows a plan view of an implantable analyte sensor that is compatible with one or more embodiments of the present disclosure.

With reference now to FIG. 14A, shown is another embodiment of an analyte sensor in accordance with one or more embodiments of the present disclosure, and representing a variation of the sensor 500 of FIGS. 13 and 14B. Referring to FIG. 14A, shown is an implantable (e.g., subcutaneous or transcutaneous) sensing region 920 according to one or more embodiments of the present disclosure including a working electrode 922 with sensing elements 931. Proximal end 940 is configured to be connected to various electrical connections for transmitting the output signals of the sensing region 920. Collectively, the distal end 925 and the proximal end 940 form the sensor tail. Sensing region 920 encompasses a bottom portion of the sensor tail. As depicted, sensing region 920 comprises a rounded tip, but other tip shapes may alternately be present to facilitate insertion into a wearer's skin.

Additionally, in one or more embodiments, sensing region 920 may include a reference electrode, a counter electrode, or counter-reference electrodes, such as those shown in FIGS. 13 and 14B. Alternative electrode configurations may be employed without departing from the scope of the present disclosure.

With reference to FIGS. 13, 14A, and 14B, it is notable that the sensor (or sensing region) 500, 920 includes sensing functionality at a distal portion of their respective sensor tails. As described above, this location may allow for enhanced contact with deeper locations beneath a wearer's skin (e.g., the subcutaneous space), where greater access to the wearer's interstitial fluid may permit greater access the analyte of interest being measured (e.g., concentration thereof). That is, the sensing region is placed sufficiently deep within a wearer's skin to allow accurate measurement of the particular analyte, whereas placing the sensing region at a more proximate location to the skin surface may be inadequate to correctly determine the concentration or other characteristic of a desired analyte.

With reference to FIGS. 13 and 14B-14D, one or more embodiments of the present disclosure, include a working electrode 501 or 320 having a sensing area 509, the sensing area 509 having at least one sensing element 322 including, for example, an analyte-specific enzyme 323 and an electron transfer agent (e.g., redox mediator) 324. The working electrode 501 or 320 is disposed on a substrate 504 or 325 which is positioned in contact with and between the working electrode 501 or 320 and a counter electrode 503. A first insulating layer 505 is disposed in contact with a surface of the working electrode 501 or 320 that is not in contact with the substrate 504 or 325. A reference electrode 502 is disposed in contact with a surface of the first insulating layer 505 that is not in contact with the working electrode 501 or 320, and a second conducting material (or layer) 510 is disposed in contact with a surface of the reference electrode 502 that is not in contact with the first insulating layer 505.

Figure 14C:
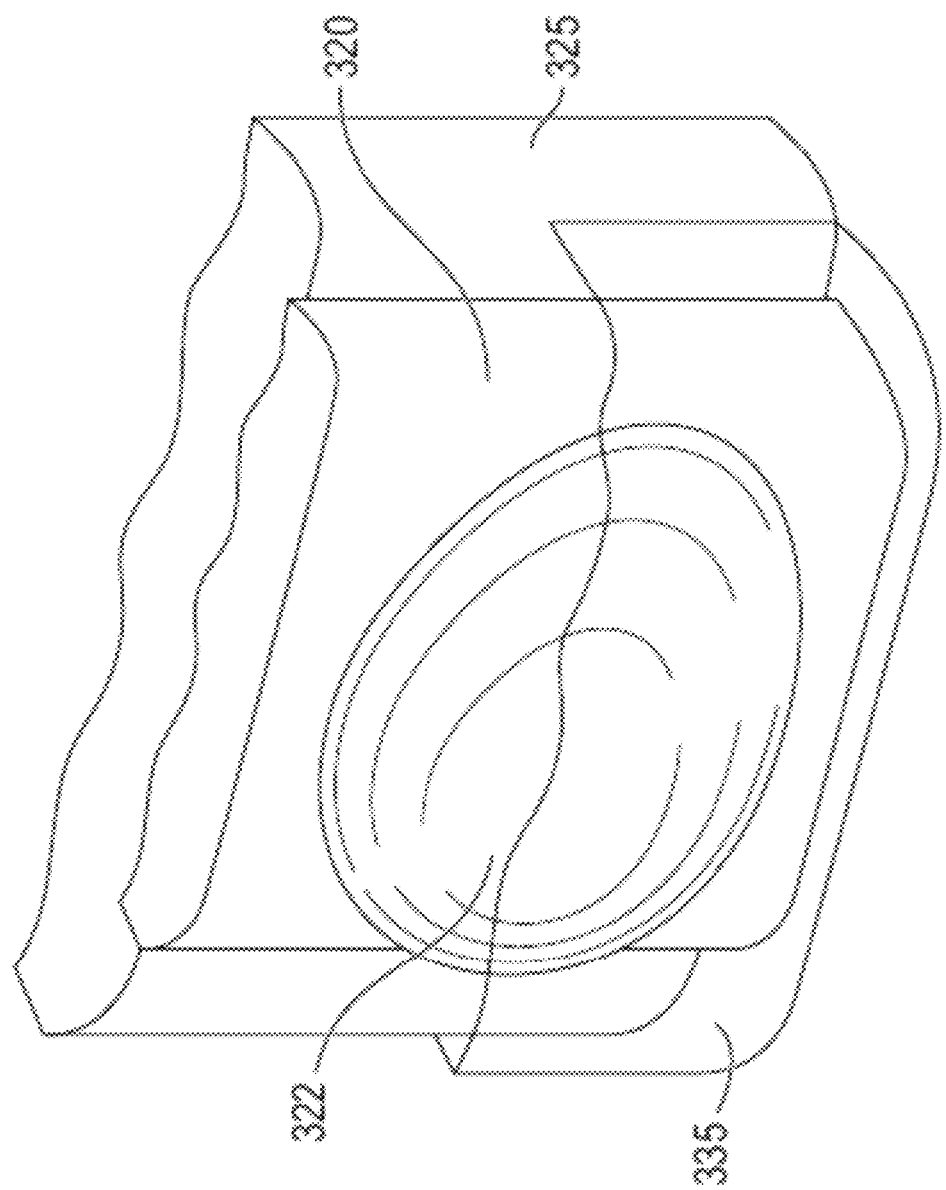
FIG. 14C shows a close-up view of the sensing layer, working electrode, and substrate with an overlaying outer membrane, according to embodiments of the present disclosure.

Also shown in FIG. 14C, disposed on at least a portion of the working electrode 320 is a sensing element 322. In some embodiments of the present disclosure, two or more sensing elements 322 may be provided on a sensing layer of the working electrode, where the two or more sensing elements are disposed laterally to each other.

In some embodiments of the present disclosure, any suitable configuration of the sensing elements 322 may be disposed on the working electrode 320 Additional configurations of sensing elements are disclosed, for example, in Hoss et al., (US 2012/0150005), the entire content of which is herein incorporated by reference.

In some embodiments of the present disclosure, with reference to FIG. 14B, a sensor 500 includes an outer membrane 520 that overlays at least the working electrode 501 and the sensing area 509. In other embodiments, the outer membrane 520 overlays the entire sensor 500. In some embodiments, the outer membrane 520 overlays all active areas of the sensor 500. For example, the active areas of the sensor 500 are found on the sensing region 920 as shown in FIG. 14A and sensing area 509 as shown in FIG. 14B. In some embodiments, the outer membrane 520 overlays the working, counter, and/or reference electrode on the sensing region 920 or sensing area 509.

FIG. 14C depicts a close-up perspective of an outer membrane 335 overlaying the sensing element 322 disposed on a working electrode 320 that is disposed on a substrate 325. As depicted, the outer membrane 335 is in the process of being overlaid. The outer membrane 335 overlays at least the entire sensing element 322.

Analyte-Specific Enzymes and Electron Transfer Agent (Redox Mediator)

In some embodiments of the present disclosure, the sensors of the present disclosure are not capable of measuring analyte directly. That is, the electrodes on the sensor cannot directly interact with the analyte. Accordingly, the analyte is detected by an enzyme protein that is capable of interacting directly with the analyte molecule. However, some enzymes (e.g., glucose oxidase) cannot exchange electrons directly with electrodes because their redox active sites are buried deep within the enzyme protein structure. Therefore, in order to transfer electrons between the redox active site of the enzyme and the electrodes, an electron transfer agent (i.e., a redox mediator) is used. Immobilization of the electron transfer agent and the analyte-specific enzyme on the sensing layer creates what is referred to as a "wire" as the immobilized molecules are capable of relaying electrons, and as such are "electrically wired." The analyte-specific enzyme is also referred to as a "wired enzyme." Wired enzymes are disclosed, for example, in Gregg et al., (U.S. Pat. No. 5,262,035), Say et al., (U.S. Pat. No. 6,134,461), and Hoss et al., (U.S. Patent Publication No. 2012/0150005), the entire contents of all of which are herein incorporated by reference. In some embodiments, the analyte-specific enzyme is crosslinked to the electron transfer agent.

In some embodiments of the present disclosure, electron transfer agents (e.g., redox mediators) are electroreducible and electrooxidizable ions or molecules having redox potentials (voltages) that are a few hundred millivolts above or below the redox potential (voltage) of the standard calomel electrode (SCE). In some embodiments, the electron transfer agents are not more reducing than about −150 mV and not more oxidizing than about +400 mV versus SCE. Examples of suitable redox mediators in the form of redox polymers are disclosed, for example, in Mao et al. (U.S. Pat. No. 6,605,200) the entire content of which is herein incorporated by reference.

According to embodiments of the present disclosure, with reference to FIG. 14D, an electron transfer agent 324 is immobilized on the working electrode 320. In some embodiments, the electron transfer agent 324 and an analyte-specific enzyme 323 are both immobilized on the working electrode 320 by any suitable means. In some embodiments, the electron transfer agent and analyte-specific enzyme are co-immobilized onto the working electrode with any suitable crosslinker. In some embodiments, the electron transfer agent and analyte-specific enzyme are co-immobilized with a chemical crosslinker, for example, poly (ethylene glycol) diglycidyl ether (PEGDGE).

In some embodiments of the present disclosure, an electron transfer agent for use in accumulation mode sensing includes a redox species selected from osmium, ruthenium, iron, or cobalt coupled with a polymer selected from poly (vinylpyridine), poly(thiophene), poly(aniline), poly(pyrrole), or poly(acetylene). In some embodiments, an electron transfer agent is the osmium (Os)-containing poly(vinylpyridine) redox polymer of Formula I.

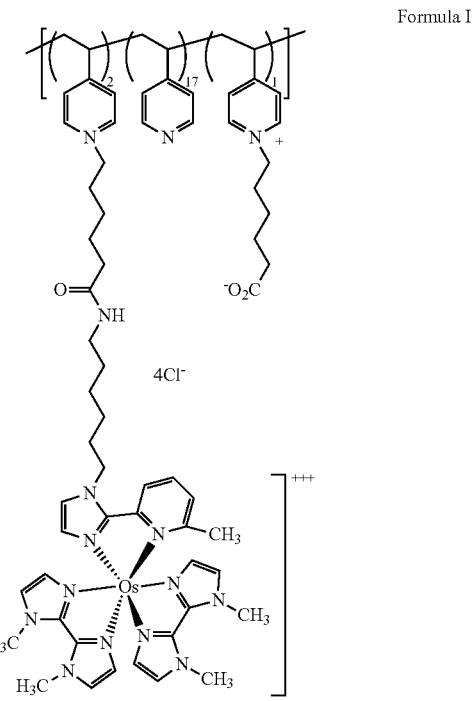

Formula I

In some embodiments of the present disclosure, the electron transfer agent may be organic, organometallic, or inorganic. Examples of organic redox species are quinones and species that in their oxidized state have quinoid structures, such as Nile blue and indophenol. Some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present disclosure because of the presence of the interfering proteins in an analyte-containing fluid. It is noted that most substituted quinones and molecules with quinoid structure are less reactive with proteins. In some embodiments, a tetrasubstituted quinone has carbon atoms in positions 1, 2, 3, and 4.

Electron transfer agents suitable for use in an accumulation mode sensing method according to embodiments of the disclosure have structures or charges which prevent or substantially reduce the diffusional loss of the electron transfer agent during the period of time that the sample is being analyzed. In some embodiments of the present disclosure, an electron transfer agent includes a redox species bound to a polymer which is capable of being immobilized on the sensing layer of the working electrode. The bond between the redox species and the polymer may be covalent, coordinative, or ionic. Useful electron transfer agents and methods for producing them are described in U.S. Pat. Nos. 5,264,104; 5,356,786; 5,262,035; and 5,320,725, the entire contents of all of which are herein incorporated by reference. Although any organic or organometallic redox species may be bound to a polymer and used as an electron transfer agent, in some embodiments of the present disclosure, the redox mediator is a transition metal compound or complex. In some embodiments, transition metal compounds or complexes include osmium, ruthenium, iron, and cobalt compounds or complexes. It will be recognized that many of the redox mediator species described herein may also be used, for example, without a polymeric component, as electron transfer agents in a carrier fluid or in a sensing layer of a sensor where leaching of the electron transfer agent is acceptable.

One type of non-releasable polymeric electron transfer agent contains a redox species covalently bound in a polymeric composition. An example of this type of mediator is poly(vinylferrocene).

Another type of non-releasable electron transfer agent contains an ionically-bound redox species. Typically, this type of mediator includes a charged polymer coupled to an oppositely charged redox species. Examples of this type of mediator include a negatively charged polymer such as Nafion (Dupont) coupled to a positively charged redox species such as an osmium, ruthenium, iron, or cobalt-coupled polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In some embodiments of the present disclosure a bound redox species is a highly charged redox species bound within an oppositely charged redox polymer.

In another embodiment of the disclosure, suitable non-releasable electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

In some embodiments of the present disclosure, the electron transfer agents are osmium transition metal complexes with one or more ligands, each ligand having a nitrogen-containing heterocycle such as 2,2'-bipyridine, 1,10-phenanthroline, or derivatives thereof. Furthermore, in some embodiments, the electron transfer agents have one or more ligands covalently bound in a polymer, each ligand having at least one nitrogen-containing heterocycle, such as pyridine, imidazole, or derivatives thereof. These preferred electron transfer agents exchange electrons rapidly between each other and the working electrode so that the complex may be rapidly oxidized and reduced.

In some embodiments of the present disclosure, an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. In some embodiments, derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine are used. In some embodiments, derivatives of 1,10-phenanthroline for complexation with the osmium cation are 4,7-dimethyl-1,10-phenanthroline and mono-, di-, and polyalkoxy-1,10-phenanthrolines, such as 4,7-dimethoxy-1,10-phenanthroline. In some embodiments of the present disclosure, polymers for complexation with the osmium cation include polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole. In some embodiments, electron transfer agents include osmium complexed to a polymer or copolymer of poly(1-vinyl imidazole).

According to embodiments of the present disclosure, electron transfer agents have a redox potential (voltage) ranging from −100 mV to about +150 mV versus the standard calomel electrode (SCE). More specifically, the potential (voltage) of the electron transfer agent ranges from −100 mV to +150 mV. In some embodiments, the potential (voltage) ranges from −50 mV to +50 mV. In other embodiments of the present disclosure, electron transfer agents have osmium, ruthenium, iron, or cobalt redox centers and a redox potential (voltage) ranging from +50 mV to −150 mV versus SCE.

Examples of Analyte-Specific Enzyme

In some embodiments of the present disclosure, an analyte-specific enzyme is provided (e.g., immobilized) onto the working electrode in order to catalyze the oxidation of the analyte to be measured. As used herein, an analyte-specific enzyme may also be referred to as an analyte-oxidizing enzyme. In some embodiments of the present disclosure, the analyte-specific enzyme is selected from glucose oxidase, NAD-glucose dehydrogenase, and FAD-glucose dehydrogenase for oxidizing glucose. In some embodiments, the analyte-specific enzyme is lactate oxidase or NAD-lactate dehydrogenase for oxidizing lactate. In some embodiments, the analyte-specific enzyme is NAD-3-hydroxybutyrate dehydrogenase for oxidizing 3-hydroxy butyrate. In some embodiments, the analyte-specific enzyme is 11β-hydroxysteroid dehydrogenase type 2 for oxidizing cortisol. In some embodiments, the analyte-specific enzyme is NAD-alcohol dehydrogenase for oxidizing alcohol. In some embodiments, the analyte-specific enzyme is pyruvate oxidase for oxidizing pyruvate. In some embodiments, the analyte-specific enzyme is NAD-glutamate dehydrogenase for oxidizing glutamate. In some embodiments, the analyte-specific enzyme is xanthine oxidase for oxidizing theophylline.

As would be understood by a person of ordinary skill in the art, any nicotinamide adenine dinucleotide (NAD) or flavin oxidase enzyme could be coupled or immobilized to the sensing layer of the working electrode in order to oxidize its corresponding analyte substrate.

In some embodiments of the present disclosure, examples of NAD-dependent enzymes include (−)-borneol dehydrogenase, (+)-borneol dehydrogenase, (+)-sabinol dehydrogenase, (+)-trans-carveol dehydrogenase, (3S,4R)-3,4-dihydroxycyclohexa-1,5-diene-1,4-dicarboxylate dehydrogenase, (R,R)-butanediol dehydrogenase, (R)-2-hydroxyfatty-acid dehydrogenase, (R)-2-hydroxyacid dehydrogenase, (R)-4-hydroxyphenyllactate dehydrogenase, (R)-aminopropanol dehydrogenase, (R)-dehydropantoate dehydrogenase, (S,S)-butanediol dehydrogenase, (S)-2-hydroxy-fatty-acid dehydrogenase, (S)-carnitine 3-dehydrogenase, (S)-usnate reductase, 1,2-dihydroxy-6-methylcyclohexa-3,5-dienecarboxylate dehydrogenase, 1,3-propanediol dehydrogenase, 1,6-dihydroxycyclohexa-2,4-diene-1-carboxylate dehydrogenase, 2-(R)-hydroxypropyl-CoM dehydrogenase, 2-(S)-hydroxypropyl-CoM dehydrogenase, 2-alkenal reductase, 2-alkyn-1-ol dehydrogenase, 2-aminobenzenesulfonate 2,3-dioxygenase, 2-chlorobenzoate 1,2-dioxygenase, 2-coumarate reductase, 2-dehydro-3-deoxy-D-gluconate 5-dehydrogenase, 2-deoxy-D-gluconate 3-dehydrogenase, 2-enoate reductase, 2-hydroxy-1,4-benzoquinone reductase, 2-hydroxy-3-oxopropionate reductase, 2-hydroxybiphenyl 3-monooxygenase, 2-hydroxymethylglutarate dehydrogenase, 2-hydroxyquinoline 5,6-dioxygenase, 2-hydroxyquinoline 8-monooxygenase, 2-oxoadipate reductase, 2-oxoaldehyde dehydrogenase (NAD+), 2-oxoisovalerate dehydrogenase (acylating), 2,3-dihydro-2,3-dihydroxybenzoate dehydrogenase, 2,3-dihydroxy-2,3-dihydro-p-cumate dehydrogenase, 2,4-diaminopentanoate dehydrogenase, 2,6-dihydroxypyridine 3-monooxygenase, 2'-phosphotransferase, 3-(imidazol-5-yl)actate dehydrogenase, 3"-deamino-3"-oxonicotianamine reductase, 3-dehydro-L-gulonate 2-dehydrogenase, 3-hydroxy-2-methylbutyryl-CoA dehydrogenase, 3-hydroxy-2-methylpyridinecarboxylate dioxygenase, 3-hydroxyacyl-CoA dehydrogenase, 3-hydroxybenzoate 6-monooxygenase, 3-Hydroxybutyrate dehydrogenase, 3-hydroxyisobutyrate dehydrogenase, 3-hydroxyphenylacetate 6-hydroxylase, 3-hydroxypimeloyl-CoA dehydrogenase, 3-hydroxypropionate dehydrogenase, 3-methylbutanal reductase, 3-oxoacyl-(acyl-carrier-protein) reductase (NADH), 3-phenylpropanoate dioxygenase, 3(or 17)a-hydroxysteroid dehydrogenase, 3alpha-hydroxy-5beta-androstane-17-one 3alpha-dehydrogenase, 3alpha-hydroxycholanate dehydrogenase, 3alpha-hydroxysteroid dehydrogenase (A-specific), 3alpha-hydroxysteroid dehydrogenase (B-specific), 3alpha,7alpha,12alpha-trihydroxycholestan-26-al 26-oxidoreductase, 3alpha(17beta)-hydroxysteroid dehydrogenase (NAD+), 3alpha(or 20beta)-hydroxysteroid dehydrogenase, 3β-Hydroxysteroid dehydrogenase, 4-(hydroxymethyl)benzenesulfonate dehydrogenase, 4-aminobenzoate 1-monooxygenase, 4-chlorophenylacetate 3,4-dioxygenase, 4-formylbenzenesulfonate dehydrogenase, 4-hydroxy-tetrahydrodipicolinate reductase, 4-hydroxybenzaldehyde dehydrogenase, 4-hydroxybenzoate 1-hydroxylase, 4-hydroxybenzoate 3-monooxygenase (NAD(P)H), 4-Hydroxybutyrate dehydrogenase, 4-Hydroxycyclohexanecarboxylate dehydrogenase, 4-hydroxymuconic-semialdehyde dehydrogenase, 4-hydroxyphenylacetaldehyde dehydrogenase, 4-hydroxyphenylacetate 1-monooxygenase, 4-hydroxyquinoline 3-monooxygenase, 4-hydroxythreonine-4-phosphate dehydrogenase, 4-nitrophenol 2-monooxygenase, 4-oxoproline reductase, 4-phosphoerythronate dehydrogenase, 4-sulfobenzoate 3,4-dioxygenase, 4-trimethylammoniobutyraldehyde dehydrogenase, 5-carboxymethyl-2-hydroxymuconic-semialdehyde dehydrogenase, 5,6-dihydroxy-3-methyl-2-oxo-1,2,5,6-tetrahydroquinoline dehydrogenase, 6-endo-hydroxycineole dehydrogenase, 6-hydroxyhexanoate dehydrogenase, 6,7-dihydropteridine reductase, 7-alpha-hydroxysteroid dehydrogenase, 15-hydroxyicosatetraenoate dehydrogenase, 15-hydroxyprostaglandin dehydrogenase (NAD+), 15-oxoprostaglandin 13-oxidase, 16-alpha-hydroxysteroid dehydrogenase, 17β-Hydroxysteroid dehydrogenase, 20-alpha-hydroxysteroid dehydrogenase, 21-hydroxysteroid dehydrogenase (NAD+), ADP-glyceromanno-heptose 6-epimerase, Alanine dehydrogenase, Alanopine dehydrogenase, Alcohol dehydrogenase, Alcohol dehydrogenase (NAD(P)+), Aldehyde dehydrogenase (NAD(P)+), Aldehyde dehydrogenase (NAD+), Aldose 1-dehydrogenase, Alkene monooxygenase, Alpha-santonin 1,2-reductase, Aminobutyraldehyde dehydrogenase, Aminomuconate-semialdehyde dehydrogenase, Anthocyanidin reductase, Anthranilate 1,2-dioxygenase (deaminating, decarboxylating), Anthraniloyl-CoA monooxygenase, Apiose 1-reductase, Aquacobalamin reductase, Arogenate dehydrogenase, Arogenate dehydrogenase (NAD(P)+), Aryl-alcohol dehydrogenase, Aryl-aldehyde dehydrogenase, Asparagusate reductase, Aspartate dehydrogenase, ATP-dependent NAD(P)H-hydrate dehydratase, Benzaldehyde dehydrogenase (NAD+), Benzene 1,2-dioxygenase, Benzoate 1,2-dioxygenase, Beta-alanopine dehydrogenase, Betaine-aldehyde dehydrogenase, Biphenyl 2,3-dioxygenase, Butanal dehydrogenase, Carnitine 3-dehydrogenase, CDP-4-dehydro-6-deoxyglucose reductase, CDP-glucose 4,6-dehydratase, CDP-paratose 2-epimerase, Cholest-5-ene-3beta,7alpha-diol 3beta-dehydrogenase, Cholestanetetraol 26-dehydrogenase, Cis-1,2-dihydro-1,2-dihydroxynaphthalene dehydrogenase, Cis-1,2-dihydrobenzene-1,2-diol dehydrogenase, Cis-1,2-dihydroxy-4-methylcyclohexa-3,5-diene-1-carboxylate dehydrogenase, Cis-2,3-dihydrobiphenyl-2,3-diol dehydrogenase, Cis-3,4-dihydrophenanthrene-3,4-diol dehydrogenase, Cis-dihydroethylcatechol dehydrogenase, CoA-disulfide reductase, Cob(II)alamin reductase, Coniferyl-aldehyde dehydrogenase, Cucurbitacin Delta23-reductase, Cyclohexane-1,2-diol dehydrogenase, Cyclohexanol dehydrogenase, Cyclopentanol dehydrogenase, Cystine reductase, D-arabinitol 2-dehydrogenase, D-arabinitol 4-dehydrogenase, D-arabinose 1-dehydrogenase, D-arabinose 1-dehydrogenase (NAD(P)+), D-iditol 2-dehydrogenase, D-malate dehydrogenase (decarboxylating), D-threo-aldose 1-dehydrogenase, D-xylose 1-dehydrogenase, D-xylulose reductase, Dibenzothiophene dihydrodiol dehydrogenase. Diferric-transferrin reductase, Dihydrouracil dehydrogenase (NAD+), Diiodophenylpyruvate reductase, Dimethylmalate dehydrogenase, DTDP-glucose 4,6-dehydratase, Ephedrine dehydrogenase, Erythrose-4-phosphate dehydrogenase, Estradiol 17alpha-dehydrogenase, Estradiol 17beta-dehydrogenase, Fatty-acyl-CoA synthase, Ferredoxin-NAD(+) reductase, Ferric-chelate reductase, Fluoren-9-ol dehydrogenase, Fluoroacetaldehyde dehydrogenase, FMN reductase, Formaldehyde dehydrogenase, Fructuronate reductase, Fumarate reductase (NADH), Furylfuramide isomerase, Galactitol 2-dehydrogenase, Galactitol-1-phosphate 5-dehydrogenase, Galactose 1-dehydrogenase, Gamma-guanidinobutyraldehyde dehydrogenase, GDP-4-dehydro-6-deoxy-D-mannose reductase, GDP-4-dehydro-D-rhamnose reductase, GDP-6-deoxy-D-talose 4-dehydrogenase, GDP-mannose 4,6-dehydratase, GDP-mannose 6-dehydrogenase, Gluconate 5-dehydrogenase, Glucose 1-dehydrogenase, Glucose 1-dehydrogenase (NAD+), Glutamate synthase (NADH), Glutarate-semialdehyde dehydrogenase, Glyceraldehyde-3-phosphate dehydrogenase (NAD(P)+), Glyceraldehyde-3-phosphate dehydrogenase (phosphorylating), Glycerate dehydrogenase, Glycerol dehydrogenase, Glycerol-3-phosphate dehydrogenase (NAD(P)+), Glycerol-3-phosphate dehydrogenase (NAD+), Glycine cleavage system, Glycine dehydrogenase, Glycolaldehyde dehydrogenase, Glyoxylate reductase, Hexadecanal dehydrogenase (acylating), Hexadecanol dehydrogenase, Histidinol dehydrogenase, Homoisocitrate dehydrogenase, Homoserine dehydrogenase, Hydrogen dehydrogenase, Hydroxycyclohexanecarboxylate dehydrogenase, Hydroxylamine reductase (NADH), Hydroxymalonate dehydrogenase, Hydroxymethylglutaryl-CoA reductase, Hydroxyphenylpyruvate reductase, Hydroxypyruvate reductase, Hyponitrite reductase, Hypotaurine dehydrogenase, Icosanoyl-CoA synthase, Imidazoleacetate 4-monooxygenase, IMP dehydrogenase, Indanol dehydrogenase, Indole-3-acetaldehyde reductase (NADH), Indolelactate dehydrogenase, Inositol 2-dehydrogenase, Inositol-3-phosphate synthase, Isocitrate dehydrogenase, Isopiperitenol dehydrogenase, Kynurenate-7,8-dihydrodiol dehydrogenase, L-amino-acid dehydrogenase, L-aminoadipate-semialdehyde dehydrogenase, L-arabinitol 2-dehydrogenase, L-arabinitol 4-dehydrogenase, L-arabinose 1-dehydrogenase, L-erythro-3,5-diaminohexanoate dehydrogenase, L-glycol dehydrogenase, L-gulonate 3-dehydrogenase, L-iditol 2-dehydrogenase, L-idonate 5-dehydrogenase, L-rhamnose 1-dehydrogenase, L-threonate 3-dehydrogenase, L-threonine 3-dehydrogenase, Lactaldehyde dehydrogenase, Lactaldehyde reductase, Lathosterol oxidase, Leghemoglobin reductase, Leucine dehydrogenase, Long-chain-alcohol dehydrogenase, Lysine dehydrogenase, Malate dehydrogenase (decarboxylating), Malate dehydrogenase (oxaloacetate-decarboxylating), Maleylacetate reductase, Malonate-semialdehyde dehydrogenase, Malonate-semialdehyde dehydrogenase (acetylating), Mannitol 2-dehydrogenase, Mannitol dehydrogenase, Mannitol-1-phosphate 5-dehydrogenase, Mannuronate reductase, Melilotate 3-monooxygenase, Meso-tartrate dehydrogenase, Methanol dehydrogenase, Methylenetetrahydrofolate dehydrogenase (NAD+), Methylglyoxal reductase (NADH-dependent), Methylmalonate-semialdehyde dehydrogenase (acylating), Mevaldate reductase, Monodehydroascorbate reductase (NADH), Morphine 6-dehydrogenase, Mycothiol-dependent formaldehyde dehydrogenase, Mycothione reductase, Myristoyl-CoA 11-(E) desaturase, Myristoyl-CoA 11-(Z) desaturase, N-acetylhexosamine 1-dehydrogenase, N-acylmannosamine 1-dehydrogenase, N-hydroxy-2-acetamidofluorene reductase, NAD(+)-dinitrogen-reductase ADP-D-ribosyltransferase, NAD(+)-diphthamide ADP-ribosyltransferase, NAD(P)(+)-protein-arginine ADP-ribosyltransferase, NAD(P)+ nucleosidase, NAD(P)+ transhydrogenase (Re/Si-specific), NAD(P)+ transhydrogenase (Si-specific), NAD(P)H dehydrogenase (quinone 1), NAD(P)H dehydrogenase (quinone), NAD+ diphosphatase, NAD+ nucleosidase, NAD+ synthase, NAD+ synthase (glutamine-hydrolysing), NADH dehydrogenase (quinone), NADH peroxidase, Naphthalene 1,2-dioxygenase, Nicotinamide-nucleotide adenylyltransferase, Nitric oxide dioxygenase, Nitrite reductase (NAD(P)H), Nitroquinoline-N-oxide reductase, Octanol dehydrogenase, Omega-hydroxydecanoate dehydrogenase, Opine dehydrogenase, Orcinol 2-monooxygenase, Ornithine cyclodeaminase, Orotate reductase (NADH), Oxaloglycolate reductase (decarboxylating), Pantoate 4-dehydrogenase, Perillyl-alcohol dehydrogenase, Phenylacetaldehyde dehydrogenase, Phenylalanine dehydrogenase, Phenylglyoxylate dehydrogenase (acylating), Phosphatidylcholine 12-monooxygenase, Phosphatidylcholine desaturase, Phosphogluconate 2-dehydrogenase, Phosphoglycerate dehydrogenase, Phosphonate dehydrogenase, Phthalate 4,5-cis-dihydrodiol dehydrogenase, Phthalate 4,5-dioxygenase, Pimeloyl-CoA dehydrogenase, Precorrin-2 dehydrogenase, Precorrin-3B synthase, Prephenate dehydrogenase, Propanediol-phosphate dehydrogenase, Protein-disulfide reductase, Pyridoxal 4-dehydrogenase, Pyrroline-2-carboxylate reductase, Pyrroline-5-carboxylate reductase, Quinate dehydrogenase, Retinal dehydrogenase, Retinol dehydrogenase, Ribitol 2-dehydrogenase, Ribitol-5-phosphate 2-dehydrogenase, Rubredoxin-NAD(+) reductase, Rubredoxin-NAD(P)(+) reductase, S–(hydroxymethyl)glutathione dehydrogenase, Saccharopine dehydrogenase (NAD+, L-glutamate-forming), Saccharopine dehydrogenase (NAD+, L-lysine-forming), Salicylaldehyde dehydrogenase, Salicylate 1-monooxygenase, Sequoyitol dehydrogenase, Serine 2-dehydrogenase, Sn-glycerol-1-phosphate dehydrogenase, Sorbitol-6-phosphate 2-dehydrogenase, Steroid 17alpha-monooxygenase, Sterol-4alpha-carboxylate 3-dehydrogenase (decarboxylating), Strombine dehydrogenase, Succinate-semialdehyde dehydrogenase, Succinate-semialdehyde dehydrogenase (NAD(P)+), Succinylglutamate-semialdehyde dehydrogenase, Sulcatone reductase, Tagaturonate reductase, Tartrate dehydrogenase, Tauropine dehydrogenase, Taxifolin 8-monooxygenase, Terephthalate 1,2-cis-dihydrodiol dehydrogenase, Terephthalate 1,2-dioxygenase, Testosterone 17beta-dehydrogenase, Tetrahydroxypteridine cycloisomerase, Thiomorpholine-carboxylate dehydrogenase, TM0436, Toluene dioxygenase, Trans-2-enoyl-CoA reductase (NAD+), Trimethylamine-N-oxide reductase, Tryptophan dehydrogenase, UDP-glucose 4-epimerase, UDP-glucose 6-dehydrogenase, UDP-glucuronate 5'-epimerase, UDP-glucuronate decarboxylase, UDP-N-acetylglucosamine 6-dehydrogenase, Ureidoglycolate dehydrogenase, Uronate dehydrogenase, Vanillate monooxygenase, Vanillin dehydrogenase, Vomifoliol dehydrogenase, Xanthine dehydrogenase, Xanthommatin reductase, or Xanthoxin dehydrogenase.

In some embodiments of the present disclosure, the analyte-specific enzyme includes a flavin oxidase such as a flavin adenine dinucleotide (FAD)-dependent or flavin mononucleotide (FMN)-dependent oxidase. Examples of FAD-dependent or FMN-dependent oxidase include: (R)-6-hydroxynicotine oxidase, (S)-2-hydroxy-acid oxidase, (S)-6-hydroxynicotine oxidase, 2-enoate reductase, 2-methyl-branched-chain-enoyl-CoA reductase, 2-nitropropane dioxygenase, 2,4-dichlorophenol 6-monooxygenase, 2,6-dihydroxypyridine 3-monooxygenase, 3-aci-nitropropanoate oxidase, 3-hydroxy-2-methylpyridinecarboxylate dioxygenase, 3-hydroxybenzoate 4-monooxygenase, 3-hydroxybenzoate 6-monooxygenase, 3-hydroxyphenylacetate 6-hydroxylase, 4-aminobenzoate 1-monooxygenase, 4-Cresol dehydrogenase (hydroxylating), 4-hydroxybenzoate 1-hydroxylase, 4-hydroxybenzoate 3-monooxygenase, 4-hydroxybenzoate 3-monooxygenase (NAD(P)H), 4-hydroxymandelate oxidase, 4-hydroxyphenylacetate 1-monooxygenase, 4-Hydroxyphenylacetate 3-monooxygenase, 4-nitrophenol 2-monooxygenase, 4-sulfobenzoate 3,4-dioxygenase, 5-pyridoxate dioxygenase, Acyl-CoA oxidase, Adenylyl-sulfate reductase, Albendazole monooxygenase, Alcohol oxidase, Anthraniloyl-CoA monooxygenase, Aquacobalamin reductase, Aquacobalamin reductase (NADPH), Arginine 2-monooxygenase, Benzene 1,2-dioxygenase, Benzoate 1,2-dioxygenase, Beta-cyclopiazonate dehydrogenase, Cellobiose dehydrogenase (acceptor), Choline oxidase, CoA-glutathione reductase, Cob(II)alamin reductase, Cyanocobalamin reductase (cyanide-eliminating), Cyclohexylamine oxidase, D-2-hydroxy-acid dehydrogenase, D-amino acid oxidase, D-arabinono-1,4-lactone oxidase, D-aspartate oxidase, D-glutamate(D-aspartate) oxidase, D-lactate dehydrogenase (cytochrome), D-sorbitol dehydrogenase (acceptor), Dehydrogluconate dehydrogenase, Deoxyribodipyrimidine photo-lyase, Dihydrouracil oxidase, Dimethylamine dehydrogenase, Dimethylglycine dehydrogenase, Dimethylglycine oxidase, Ferredoxin-NADP(+) reductase, Gluconate 2-dehydrogenase (acceptor), Glucose dehydrogenase (acceptor), Glucoside 3-dehydrogenase, Glutamate synthase (ferredoxin), Glutamate synthase (NADH), Glutamate synthase (NADPH), Glutathione oxidase, Glycerol-3-phosphate oxidase, Hydrogen dehydrogenase, Hydroxylamine reductase, Imidazoleacetate 4-monooxygenase, Indole 2,3-dioxygenase, Indole-3-acetaldehyde oxidase, Isovaleryl-CoA dehydrogenase, Kynurenine 3-monooxygenase, L-amino-acid oxidase, L-aspartate oxidase, L-galactonolactone oxidase, L-glutamate oxidase, L-lactate dehydrogenase (cytochrome), Lactate 2-monooxygenase, Lathosterol oxidase, Latia-luciferin monooxygenase (demethylating), Long-chain acyl-CoA dehydrogenase, Lysine 2-monooxygenase, Malate dehydrogenase (quinone), Malate oxidase, Mandelonitrile lyase, Melilotate 3-monooxygenase, N-methyl-L-amino-acid oxidase, NAD(P)+ transhydrogenase (Si-specific), NAD(P)H dehydrogenase (quinone 1), NAD(P)H dehydrogenase (quinone), NADH peroxidase, NADPH dehydrogenase, NADPH dehydrogenase (quinone), NADPH-cytochrome-c2 reductase, NADPH-hemoprotein reductase, Nicotinate dehydrogenase, Nicotine dehydrogenase, Nitrite reductase (NAD(P)H), Nitrite reductase (NO-forming), Orcinol 2-monooxygenase, Orotate reductase (NADH), Orotate reductase (NADPH), Oxalate oxidase, Phenol 2-monooxygenase, Phenylglyoxylate dehydrogenase (acylating), Phthalate 4,5-dioxygenase, Polyamine oxidase, Proline dehydrogenase, Putrescine oxidase, Pyranose oxidase, Pyridoxine 4-oxidase, Pyridoxine 5-dehydrogenase, Pyruvate dehydrogenase (cytochrome), Pyruvate oxidase, Pyruvate oxidase (CoA-acetylating), Retinal dehydrogenase, Rubredoxin-NAD(+) reductase, Salicylate 1-monooxygenase, Sarcosine dehydrogenase, Short-chain acyl-CoA dehydrogenase, Spermidine dehydrogenase, Steroid 9alpha-monooxygenase, Tartronate-semialdehyde synthase, Taxifolin 8-monooxygenase, Thiamine oxidase, Trypanothione-disulfide reductase, UDP-N-acetylmuramate dehydrogenase, or Vanillyl-alcohol oxidase.

Sensor Membrane

In some embodiments of the present disclosure, with reference to FIGS. 13 and 14B-14D, the sensor 500 or a portion of the sensor 500, includes an outer membrane 520 or 335 that overlays at least the working electrode 501 or 320 and a sensing element 322 or a sensing area 509. Electrochemical sensors are often times coated with an outer membrane 520 or 335 (e.g., a polymer membrane) in order to provide stability to the sensing reagents (e.g., the analyte-specific enzyme 323 and redox mediator 324), as well as provide mass-transport limitations, biocompatibility, and/or to prevent electrode fouling.

In some embodiments of the present disclosure, the membrane is composed of two components, a hydrophilic (water-loving) polymer and a crosslinker. The crosslinker attaches the polymer molecules together and anchors them to the sensing layer of the sensor. For analytes such as glucose which are found in vivo at concentrations of about 5 mM, a flux-limiting membrane is necessary to prevent electrode fouling. Examples of flux-limiting sensor membranes are disclosed, for example, in Mao et al. U.S. Pat. No. 6,932,894, the entire content of which is herein incorporated by reference.

For analytes as lower concentrations, a flux-limiting membrane could be used with increased accumulation time, for example, up to 30 minutes. Alternatively, for analytes at lower concentrations a highly permeably membrane may be used in order to maintain the natural flow of analyte to the sensing layer, while also having a membrane to increase the biocompatibility of the sensor. For example a hydrophilic membrane surface does not aggravate the body's immune system, thereby reducing the risk of inflammation and other responses that could compromise the performance of the sensor.

Analyte Monitoring Systems

Accordingly, embodiments include analyte monitoring devices and systems that include an analyte sensor at least a portion of which is positionable beneath the skin surface of the user for the in vivo detection of an analyte in a body fluid. Analyte monitoring systems are disclosed in Say et al. (U.S. Pat. No. 6,134,461) and Hoss et al., (U.S. Patent Application Publication No. 2012/0150005), the entire contents of both of which are herein incorporated by reference Embodiments of the present disclosure include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of analyte, which may be used to infer the analyte level in the user's bloodstream. Analyte sensors may be insertable into a vein, artery, or other portion of the body containing fluid. In some embodiments, the analyte sensors may be configured for monitoring the level of the analyte over a time period which may range from seconds, minutes, hours, days, weeks, to months, or longer.

In some embodiments of the present disclosure, the analyte sensors are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time $t_0$, the rate of change of the analyte, etc. Predictive alarms may notify the user of a predicted analyte level that may be of concern in advance of the user's analyte level reaching the future predicted analyte level. This provides the user an opportunity to take corrective action.

Figure 15:
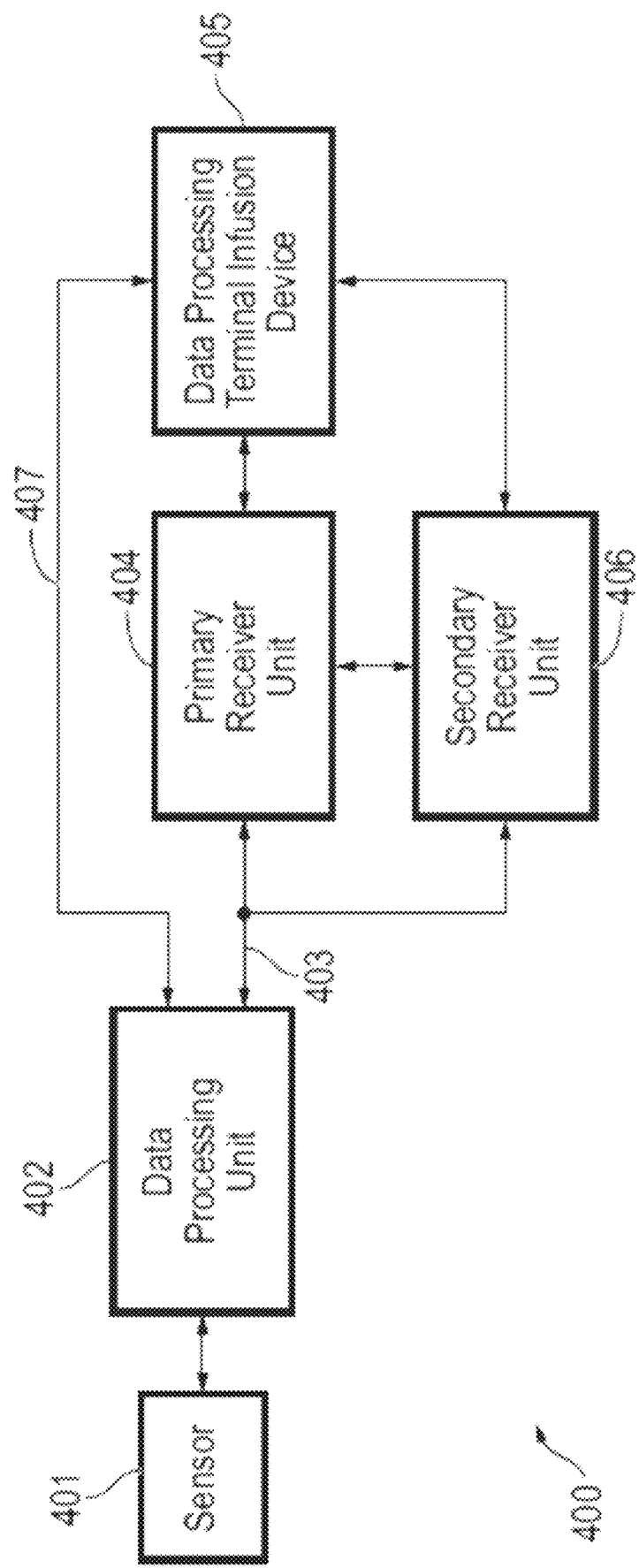
FIG. 15 is a block diagram of an embodiment of an analyte monitoring system according to embodiments of the present disclosure.

FIG. 15 shows a data monitoring and management system such as, for example, an analyte monitoring system 400 in accordance with certain embodiments of the present disclosure. Aspects of embodiments of the present disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes as disclosed herein at the same time or at different times.

Analytes that may be monitored include, but are not limited to, glucose, lactate, 3-hydroxy butyrate, cortisol, alcohol, pyruvate, glutamate, theophylline, acetylcholine, amylase, bilirubin, cholesterol, chorionic gonadotropin, glycosylated hemoglobin (HbA1c), creatine kinase (e.g., CK-MB), creatine, creatinine, DNA, fructosamine, glucose derivatives, glutamine, growth hormones, hormones, 3-hydroxy butyrate, ketones, ketone bodies, peroxide, prostate-specific antigen, prothrombin, RNA, thyroid stimulating hormone, and troponin. Analytes also include drugs, such as, for example, antibiotics (e.g., gentamicin, vancomycin, and the like), digitoxin, digoxin, drugs of abuse, theophylline, and warfarin, may also be monitored. In some embodiments, more than one analyte is monitored, and the analytes may be monitored at the same or different times.

The analyte monitoring system 400 includes an analyte sensor 401, a data processing unit 402 connectable to the sensor 401, and a primary receiver unit 404. In some instances, the primary receiver unit 404 is configured to communicate with the data processing unit 402 via a communication link 403. In certain embodiments, the primary receiver unit 404 may be further configured to transmit data to a data processing terminal 405 to evaluate or otherwise process or format data received by the primary receiver unit 404. The data processing terminal 405 may be configured to receive data directly from the data processing unit 402 via a communication link 407, which may optionally be configured for bi-directional communication. Further, the data processing unit 402 may include a transmitter or a transceiver to transmit and/or receive data to and/or from the primary receiver unit 404 and/or the data processing terminal 405 and/or optionally a secondary receiver unit 406.

Also shown in FIG. 15 is an optional secondary receiver unit 406 which is operatively coupled to the communication link 403 and configured to receive data transmitted from the data processing unit 402. The secondary receiver unit 406 may be configured to communicate with the primary receiver unit 404, as well as the data processing terminal 405. In some embodiments, the secondary receiver unit 406 may be configured for bi-directional wireless communication with each of the primary receiver unit 404 and the data processing terminal 405. As discussed in detail below, in some instances, the secondary receiver unit 406 may be a de-featured receiver as compared to the primary receiver unit 404, for instance, the secondary receiver unit 406 may include a limited or minimal number of functions and features as compared with the primary receiver unit 404. As such, the secondary receiver unit 406 may include a smaller (in one or more, including all, dimensions), compact housing or embodied in a device including a wrist watch, arm band, PDA, mp3 player, cell phone, etc., for example. Alternatively, the secondary receiver unit 406 may be configured with the same or substantially similar functions and features as the primary receiver unit 404. The secondary receiver unit 406 may include a docking portion configured to mate with a docking cradle unit for placement by, e.g., the bedside for night time monitoring, and/or a bi-directional communication device. A docking cradle may recharge a power supply.

Only one analyte sensor 401, data processing unit 402 and data processing terminal 405 are shown in the embodiment of the analyte monitoring system 400 illustrated in FIG. 15. However, it will be appreciated by one of ordinary skill in the art that the analyte monitoring system 400 may include more than one sensor 401 and/or more than one data processing unit 402, and/or more than one data processing terminal 405. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 400. For example, unique IDs, communication channels, and the like, may be used.

In certain embodiments, the sensor 401 is physically positioned in or on the body of a user whose analyte level is being monitored. The sensor 401 may be configured to at least periodically sample the analyte level of the user and convert the sampled analyte level into a corresponding signal for transmission by the data processing unit 402. The data processing unit 402 is capable of being coupled to the sensor 401 so that both devices are positioned in or on the user's body, with at least a portion of the analyte sensor 401 positioned transcutaneously. The data processing unit may include a fixation element, such as an adhesive or the like, to secure it to the user's body. A mount attachable to the user and mateable with the data processing unit 402 may be used. For example, a mount may include an adhesive surface. The data processing unit 402 performs data processing functions, where such functions may include, but are not limited to, filtering and encoding of data signals, each of which corresponds to a sampled analyte level of the user, for transmission to the primary receiver unit 404 via the communication link 403. In some embodiments, the sensor 401 or the data processing unit 402 or a combined sensor/data processing unit may be wholly implantable under the skin surface of the user.

In certain embodiments, the primary receiver unit 404 may include an analog interface section including an RF receiver and an antenna that is configured to communicate with the data processing unit 402 via the communication link 403, and a data processing section for processing the received data from the data processing unit 402 including data decoding, error detection and correction, data clock generation, data bit recovery, etc., or any combination thereof.

In operation, the primary receiver unit 404 in certain embodiments is configured to synchronize with the data processing unit 402 to uniquely identify the data processing unit 402, based on, for example, an identification information of the data processing unit 402, and thereafter, to periodically receive signals transmitted from the data processing unit 402 associated with the monitored analyte levels detected by the sensor 401.

Referring again to FIG. 15, the data processing terminal 405 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 405 may further be connected to a data network (not shown) for storing, retrieving, updating, and/or analyzing data corresponding to the detected analyte level of the user.

The data processing terminal 405 may include a drug delivery device (e.g., an infusion device), such as an insulin infusion pump or the like, which may be configured to administer a drug (e.g., insulin) to the user, and which may be configured to communicate with the primary receiver unit 404 for receiving, among others, the measured analyte level. Alternatively, the primary receiver unit 404 may be configured to integrate an infusion device therein so that the primary receiver unit 404 is configured to administer an appropriate drug (e.g., insulin) to users, for example, for administering and modifying basal profiles, as well as for determining appropriate boluses for administration based on, among others, the detected analyte levels received from the data processing unit 402. An infusion device may be an external device or an internal device, such as a device wholly implantable in a user.

In certain embodiments, the data processing terminal 405, which may include an infusion device, e.g., an insulin pump, may be configured to receive the analyte signals from the data processing unit 402, and thus, incorporate the functions of the primary receiver unit 404 including data processing for managing the user's insulin therapy and analyte monitoring. In certain embodiments, the communication link 403, as well as one or more of the other communication interfaces shown in FIG. 15, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

In further embodiments, the data processing unit 402 and/or the primary receiver unit 404 and/or the secondary receiver unit 406, and/or the data processing terminal (infusion device) 405 may be configured to receive the analyte value wirelessly over a communication link from, for example, a blood analyte meter. In further embodiments, a user manipulating or using the analyte monitoring system 400 (FIG. 15) may manually input the analyte value using, for example, a user interface (for example, a keyboard, keypad, voice commands, and the like) incorporated in one or more of the data processing unit 402, the primary receiver unit 404, the secondary receiver unit 406, or the data processing terminal (infusion device) 405.

A sensor (e.g., an enzymatic biosensor) as disclosed herein for measuring low nanomolar concentrations of an analyte may be used in an in vivo monitoring system which while positioned in vivo in a user (e.g., human subject) makes contact with the bodily fluid of the user and senses one or more analyte levels contained therein. An in vivo monitoring system may include one or more reader devices that receive sensed analyte data from a sensor control device. These reader devices mayu process and/or display the sensed analyte data, or sensor data, in any number of forms, to the user.

With reference to FIG. 16, in some embodiments, a reader device 120 may be a mobile communication device such as a dedicated reader device (configured for communication with a sensor control device 102 (FIG. 17), and optionally a computer system, but without mobile telephony communication capability) or a mobile telephone including, but not limited to, a Wi-Fi or internet enabled smart phone, tablet, or personal digital assistant (PDA). Examples of smart phones may include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

A reader device 120 may also be configured as a mobile smart wearable electronics assembly, such as an optical assembly that is worn over or adjacent to the user's eye (e.g., a smart glass or smart glasses, such as Google glasses, which is a mobile communication device). This optical assembly may have a transparent display that displays information about the user's analyte level to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

FIG. 16 is a block diagram of an example embodiment of a reader device 120 configured as a smart phone. Here, reader device 120 includes an input component 121, display 122, and processing circuitry 206, which my include one or more processors, microprocessors, controllers, and/or microcontrollers, each of which may be a discrete chip or distributed amongst (and a portion of) a number of different chips. Here, processing circuitry 206 includes a communications processor 202 having on-board memory 203 and an applications processor 204 having on-board memory 205. Reader device 120 further includes RF communication circuitry 208 coupled with an RF antenna 209, a memory 210, multi-functional circuitry 212 with one or more associated antennas 214, a power supply 216, power management circuitry 218, and a clock 219. FIG. 16 is an abbreviated representation of the typical hardware and functionality that resides within a smart phone and those of ordinary skill in the art will readily recognize that other hardware and functionality (e.g., codecs, drivers, glue logic) may also be included.

Also shown in FIG. 16, communications processor 202 may interface with RF communication circuitry 208 and perform analog-to-digital conversions, encoding and decoding, digital signal processing and other functions that facilitate the conversion of voice, video, and data signals into a format (e.g., in-phase and quadrature) suitable for provision to RF communication circuitry 208, which may then transmit the signals wirelessly. Communications processor 202 may also interface with RF communication circuitry 208 to perform the reverse functions necessary to receive a wireless transmission and convert it into digital data, voice, and video. RF communication circuitry 208 may include a transmitter and a receiver (e.g., integrated as a transceiver) and associated encoder logic.

With reference again to FIG. 16, applications processor 204 may be adapted to execute the operating system and any software applications that reside on reader device 120, process video and graphics, and perform those other functions not related to the processing of communications transmitted and received over RF antenna 209. The smart phone operating system will operate in conjunction with a number of applications on reader device 120. Any number of applications (also known as "user interface applications") may be running on reader device 120 at any one time, and may include one or more applications that are related to a diabetes monitoring regime, in addition to the other commonly used applications that are unrelated to such a regime, e.g., email, calendar, weather, sports, games, etc. For example, the data indicative of a sensed analyte level and in vitro blood analyte measurements received by the reader device may be securely communicated to user interface applications residing in memory 210 of reader device 120. Such communications may be securely performed, for example, through the use of mobile application containerization or wrapping technologies.

Memory 210 may be shared by one or more of the various functional units present within reader device 120, or may be distributed amongst two or more of them (e.g., as separate memories present within different chips). Memory 210 may also be a separate chip of its own. Memories 203, 205, and 210 are non-transitory, and may be volatile (e.g., RAM, etc.) and/or non-volatile memory (e.g., ROM, flash memory, F-RAM, etc.). Multi-functional circuitry 212 may be implemented as one or more chips and/or components (e.g., transmitter, receiver, transceiver, and/or other communication circuitry) that perform other functions such as local wireless communications, e.g., with sensor control device 102 under the appropriate protocol (e.g., Wi-Fi, Bluetooth, Bluetooth Low Energy, Near Field Communication (NFC), Radio Frequency Identification (RFID), proprietary protocols, and others) and determining the geographic position of reader device 120 (e.g., global positioning system (GPS) hardware). One or more other antennas 214 are associated with the functional circuitry 212 as needed to operate with the various protocols and circuits.

Power supply 216 may include one or more batteries, which may be rechargeable or single-use disposable batteries. Power management circuitry 218 may regulate battery charging and power supply monitoring, boost power, perform DC conversions, and the like.

Reader device 120 may also include or be integrated with a drug (e.g., insulin, etc.) delivery device such that they, e.g., share a common housing. Examples of such drug delivery devices may include medication pumps having a cannula that remains in the body to allow infusion over a multi-hour or multi-day period (e.g., wearable pumps for the delivery of basal and bolus insulin). Reader device 120, when combined with a medication pump, may include a reservoir to store the drug, a pump connectable to transfer tubing, and an infusion cannula. The pump may force the drug from the reservoir, through the tubing and into the diabetic's body by way of the cannula inserted therein. Other examples of drug delivery devices that may be included with (or integrated with) reader device 120 include portable injection devices that pierce the skin only for each delivery and are subsequently removed (e.g., insulin pens). A reader device 120, when combined with a portable injection device, may include an injection needle, a cartridge for carrying the drug, an interface for controlling the amount of drug to be delivered, and an actuator to cause injection to occur. The device may be used repeatedly until the drug is exhausted, at which point the combined device may be discarded, or the cartridge may be replaced with a new one, at which point the combined device may be reused repeatedly. The needle may be replaced after each injection.

The combined device may function as part of a closed-loop system (e.g., an artificial pancreas system requiring no user intervention to operate) or semi-closed loop system (e.g., an insulin loop system requiring seldom user intervention to operate, such as to confirm changes in dose). For example, the diabetic's analyte level may be monitored in a repeated automatic fashion by sensor control device 102, which may then communicate that monitored analyte level to reader device 120, and the appropriate drug dosage to control the diabetic's analyte level may be automatically determined and subsequently delivered to the diabetic's body. Software instructions for controlling the pump and the amount of insulin delivered may be stored in the memory of reader device 120 and executed by the reader device's processing circuitry. These instructions may also cause calculation of drug delivery amounts and durations (e.g., a bolus infusion and/or a basal infusion profile) based on the analyte level measurements obtained directly or indirectly from sensor control device 102. In some embodiments sensor control device 102 may determine the drug dosage and communicate that to reader device 120.

FIG. 17 is a block diagram depicting an example embodiment of sensor control device 102 having analyte sensor 104 and sensor electronics 250 (including analyte monitoring circuitry) that may have the majority of the processing capability for rendering end-result data suitable for display to the user. In FIG. 17, a single semiconductor chip 251 is depicted that may be a custom application specific integrated circuit (ASIC). Shown within ASIC 251 are certain high-level functional units, including an analog front end (AFE) 252, power management (or control) circuitry 254, processor 256, and communication circuitry 258 (which may be implemented as a transmitter, receiver, transceiver, passive circuit, or otherwise according to the communication protocol). In this embodiment, both AFE 252 and processor 256 are used as analyte monitoring circuitry, but in other embodiments either circuit may perform the analyte monitoring function. Processor 256 may include one or more processors, microprocessors, controllers, and/or microcontrollers, each of which may be a discrete chip or distributed amongst (and a portion of) a number of different chips.

A memory 253 may also be included within ASIC 251 and may be shared by the various functional units present within ASIC 251, or may be distributed amongst two or more of them. Memory 253 may also be a separate chip. Memory 253 is non-transitory and may be volatile and/or non-volatile memory. In this embodiment, ASIC 251 is coupled with power source 260, which may be a coin cell battery, or the like. AFE 252 interfaces with in vivo analyte sensor 104 and receives measurement data therefrom and outputs the data to processor 256 in digital form, which in turn may, in some embodiments, process in any suitable manner. This data may then be provided to communication circuitry 258 for sending, by way of antenna 261, to reader device 120, for example, where minimal further processing is needed by the resident software application to display the data. Antenna 261 may be configured according to the needs of the application and communication protocol. Antenna 261 may be, for example, a printed circuit board (PCB) trace antenna, a ceramic antenna, or a discrete metallic antenna. Antenna 261 may be configured as a monopole antenna, a dipole antenna, an F-type antenna, a loop antenna, and others.

Information may be communicated from sensor control device 102 to a second device (e.g., reader device 120) at the initiative of sensor control device 102 or reader device 120. For example, information may be communicated automatically and/or repeatedly (e.g., continuously) by sensor control device 102 when the analyte information is available, or according to a schedule (e.g., about every 1 minute, about every 5 minutes, about every 10 minutes, or the like), in which case the information may be stored or logged in a memory of sensor control device 102 for later communication. The information may be transmitted from sensor control device 102 in response to receipt of a request by the second device. This request may be an automated request, e.g., a request transmitted by the second device according to a schedule, or may be a request generated at the initiative of a user (e.g., an ad hoc or manual request). In some embodiments, a manual request for data is referred to as a "scan" of sensor control device 102 or an "on-demand" data transfer from device 102. In some embodiments, the second device may transmit a polling signal or data packet to sensor control device 102, and device 102 may treat each poll (or polls occurring at certain time intervals) as a request for data and, if data is available, then may transmit such data to the second device. In many embodiments, the communication between sensor control device 102 and the second device are secure (e.g., encrypted and/or between authenticated devices), but in some embodiments the data may be transmitted from sensor control device 102 in an unsecured manner, e.g., as a broadcast to all listening devices in range.

Different types and/or forms and/or amounts of information may be sent as part of each communication including, but not limited to, one or more of current sensor measurements (e.g., the most recently obtained analyte level information temporally corresponding to the time the reading is initiated), rate of change of the measured metric over a predetermined time period, rate of the rate of change of the metric (acceleration in the rate of change), or historical metric information corresponding to metric information obtained prior to a given reading and stored in a memory of sensor control device 102.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments reader device 120 may output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be collected by an optional temperature sensor 257. Those readings or measurements may be communicated (either individually or as an aggregated measurement over time) from sensor control device 102 to another device (e.g., reader or reader device 120). The temperature reading or measurement, however, may be used in conjunction with a software routine executed by reader device 120 to correct or compensate the analyte measurement output to the user, instead of or in addition to actually displaying the temperature measurement to the user.

The following Examples are presented for illustrative purposes only, and do not limit the scope or content of the present application.

EXAMPLES

Example 1. Calculating Sensitivity of Accumulation Mode Detection Using Polymer-Coated Sensors and Long Accumulation Times FIG. 5 shows the calibration curves obtained via amperometry and accumulation mode sensing using polymer coated glucose sensors at glucose concentrations from 0 to 500 µM. Each calibration curve is the average response of four sensors. However, unlike amperometry, accumulation mode sensing enables the sensitivity of the sensor to be easily tuned by altering the accumulation time. For both the peak height and peak area measurements, the sensor sensitivity is increased by a factor of roughly 10 by increasing the accumulation time from 1 min to 10 min. The sensitivity for each calibration curve shown in FIG. 5 was calculated as the slope of the linear fit with the tabulated data shown in Table 1.

TABLE 1

| Accumulation Time (minutes) | Sensitivity | | |
|---|---|---|---|
| | Amperometry (nA/µM) | Accumulation Mode Peak Height (nA/µM) | Accumulation Mode Peak Area (nC/µM) |
| 1 | 0.0022 | 0.0043 | 0.11 |
| 2 | 0.0023 | 0.0086 | 0.26 |
| 5 | 0.0024 | 0.020 | 0.65 |
| 10 | 0.0025 | 0.039 | 1.33 |

Since the peak height and amperometry measurements are made in the same units, their sensitivities may be directly compared. Using the data from the flux-membrane sensor as shown in FIG. 5, the ratio (i.e., fold increase) of the accumulation mode sensitivity to the amperometry sensitivity under equivalent sensor conditions was calculated with the tabulations shown in Table 2. As indicated, at an accumulation time of 1 minute, the sensor sensitivity is 2-fold higher using accumulation mode sensing in comparison to amperometry. Accordingly, by increasing the accumulation time to 10 minutes, the sensitivity difference increases to 15-fold.

TABLE 2

| Accumulation Time (minutes) | Ratio Peak Height/Amperometry |
|---|---|
| 1 | 2.0 |
| 2 | 3.7 |
| 5 | 8.3 |
| 10 | 15.6 |

Example 2. Optimization of Accumulation Mode Signal for High Sensitivity Detection with Increased Frequency and the Addition of Carbon Nanotubes FIG. 7 shows the accumulation mode detection of 200 nM glucose under two different signal filtering frequencies of 0.032 Hz and 3.2 Hz. As shown, the detection peak is much sharper using the higher frequency filter, leading to a larger peak height. The area under the two curves, however, does not change. This shows that when using the peak height measurement, a higher frequency filter is ideal for maximizing the signal magnitude. In particular, changing the filtering frequency from 0.032 Hz to 3.2 Hz was found to increase the peak height signal by a factor of 2-3. Furthermore, filtering frequencies greater than 3.2 Hz, signal noise was too large to make accurate measurements of the both the amperometric current and the accumulation peak characteristics (peak height and area).

As a mechanism means for enhancing the accumulation mode signal, carbon nanotubes (CNTs) were added to make the deposited sensing reagent more uniform and electrically conductive thereby increasing the kinetics of the redox mediated oxidation step. This increase in kinetics resulted in the accumulation mode current spike having a larger peak height. FIG. 8A shows micrographs of deposited and cured glucose sensing reagent with and without CNTs. As shown, the sensing reagent containing CNTs is deposited more uniformly, while the sensing reagent lacking CNTs exhibits a large "coffee ring effect." The addition of CNTs to the sensing reagent was found to increase the peak height signal by a factor of 5 to 6.

Additionally, FIG. 8B show the results of an experiment probing the effect of both the signal filtering frequency and the addition of CNTs to the sensing reagent on sensor sensitivity using amperometry and accumulation mode sensing as measured by peak height and peak area using example glucose sensors at glucose concentrations from 0-200 nM as indicated. Four sensors of both types (with and without CNTs in the sensing reagent) were tested, and each calibration curve is the average response of the four indicated sensors. A ten minute accumulation time was used for each accumulation mode detection. Two consecutive measurements were made at each glucose concentration: one using a filtering frequency of 0.032 Hz and one using a filtering frequency of 3.2 Hz.

The sensitivity for each calibration curve in FIG. 8B was calculated as the slope of the linear fit and the tabulated data is shown in Table 3. As seen, the sensor sensitivity from amperometric measurement changes minimally with filtering frequency and CNT presence, staying below 0.0003 nA/nM for all conditions. For accumulation mode measurement using the peak area, the sensor sensitivity doesn't change with filtering frequency, but does slightly increase upon addition of CNTs to the sensing reagent. The most drastic changes in sensor sensitivity are observed for accumulation mode measurement using the peak height. Both the filtering frequency and the addition of CNTs to the sensing reagent increase the sensor sensitivity. Increasing the filtering frequency from 0.032 Hz to 3.2 Hz increases the sensitivity by a factor of about 2.5, while adding CNTs to the sensing reagent increase the sensitivity by a factor of about 5.5. Furthermore, an increase in the filter frequency combined with the addition of CNTs increases the sensitivity of the accumulation mode measurement by a factor of about 14.

TABLE 3

| Variables | | | Sensitivity | |
|---|---|---|---|---|
| Filtering Frequency (Hz) | CNTs in Sensing Reagent? | Amperometry (nA/nM) | Accumulation Mode Peak Height (nA/nM) | Accumulation Mode Peak Area (nC/nM) |
| 0.032 | No | 0.00023 | 0.0071 | 0.11 |
| 3.2 | No | 0.00024 | 0.018 | 0.10 |
| 0.032 | Yes | 0.00026 | 0.041 | 0.14 |
| 3.2 | Yes | 0.00027 | 0.10 | 0.15 |

Since the peak height and amperometry measurements are made in the same units, their sensitivities may be directly compared. Table 4 gives the ratio of the accumulation mode sensitivity to the amperometry sensitivity under equivalent sensor conditions. As shown, even at a filtering frequency of 0.032 Hz and without CNTs in the sensing reagent, the sensor sensitivity is 30-fold higher using accumulation mode sensing in comparison to amperometry. Accordingly, by increasing the filtering frequency and adding CNTs to the sensing reagent to optimize the accumulation mode peak height, the sensitivity difference increases to nearly 400-fold.

TABLE 4

| Variables | | Ratio |
|---|---|---|
| Filtering Frequency (Hz) | CNTs in Sensing Reagent? | Peak Height/Amperometry |
| 0.032 | No | 31 |
| 3.2 | No | 75 |
| 0.032 | Yes | 158 |
| 3.2 | Yes | 370 |

Example. 3

Figure 9B:
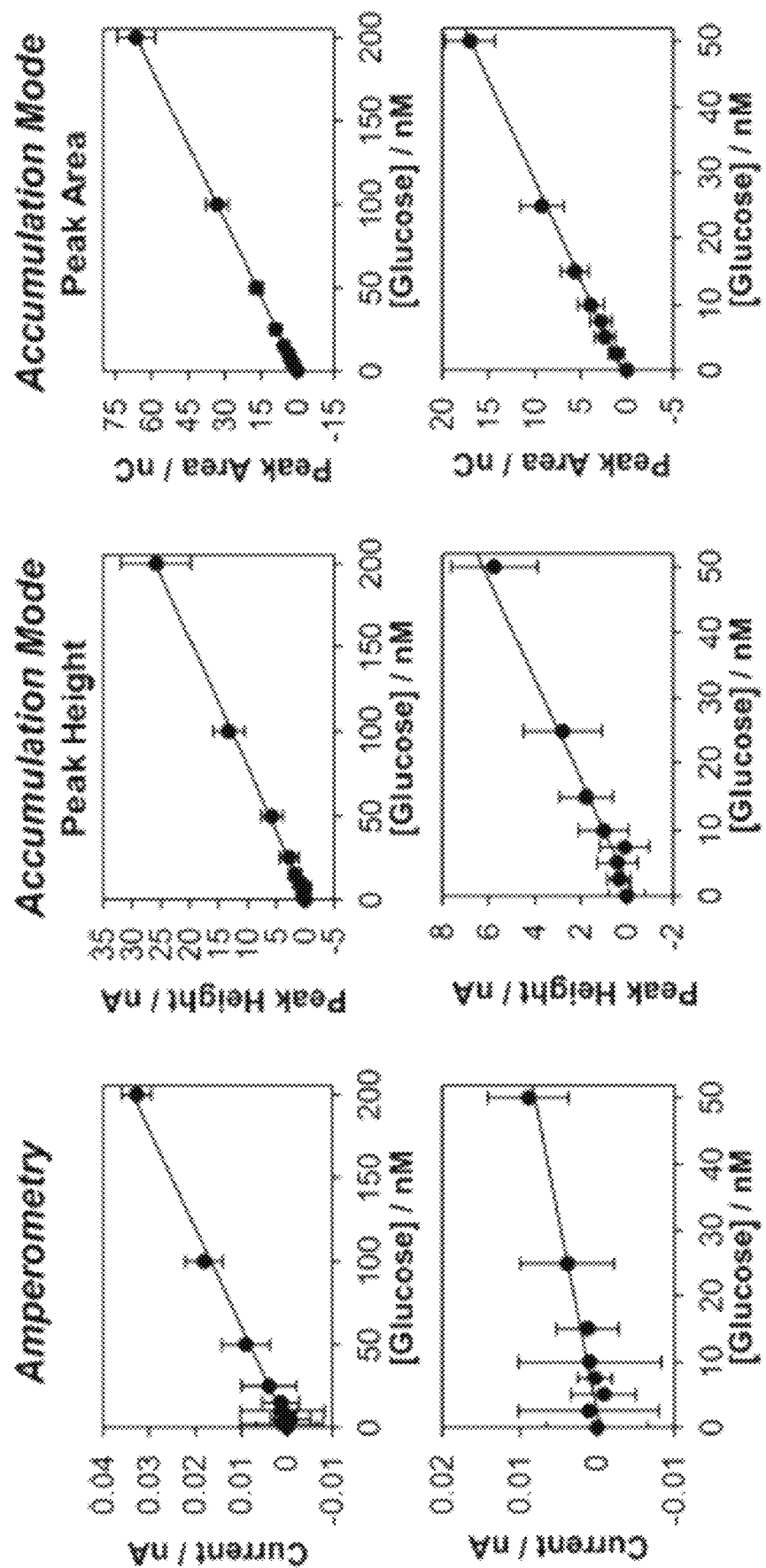
FIG. 9B shows calibration curves with corresponding linear fit resulting from the amperometry and accumulation mode signals measured for the sensing experiment shown in FIG. 8A, in which each signal is the background-subtracted mean of 8 sensors, with error bars representing the standard deviation, and the bottom row of plots is a zoom-in showing glucose concentrations from 0 to 50 nM, according to embodiments of the present disclosure.

Comparison of sensitivity, detection limit, and linear range for amperometry and accumulation mode sensing using an accumulation time of 30 minutes, 3.2 Hz signal frequency, and the addition of carbon nanotubes. As shown in FIG. 9B, the currents associated with the amperometric measurements are exceedingly small (<50 pA) and lose linearity below 100 nM, while the signals for accumulation mode sensing are much larger and retain linearity well below 100 nM. Table 5 below shows the sensitivity, lower limit of detection (LOD) (calculated as $3\sigma$/slope, utilizing standard approach 1), and linear detection range associated with these measurements as disclosed in Example 5. Standard approach 1 is disclosed in Mocak et al., *Pure Appl. Chem.* 1997, 69:297-328, the entire content of which is herein incorporated by reference. In particular, standard approach 1 is a method for calculating the LOD as "$3\sigma$/slope" where "$\sigma$" is the standard deviation of the blank and "slope" is the slope of the calibration curve.

TABLE 5

| Measurement Method | Sensitivity | LOD/nM | Linear Range/µM |
|---|---|---|---|
| Amperometry | 0.00017 ± 0.00001 nA/nM | 120 ± 42 | 0.12->100 |
| Accumulation Mode-Peak Height | 0.14 ± 0.03 nA/nM | 20 ± 16 | 0.02-2 |
| Accumulation Mode-Peak Area | 0.33 ± 0.04 nC/nM | 4.7 ± 1.4 | 0.004-5 |

Example 4. Analysis of Background Signal

Figure 10B:
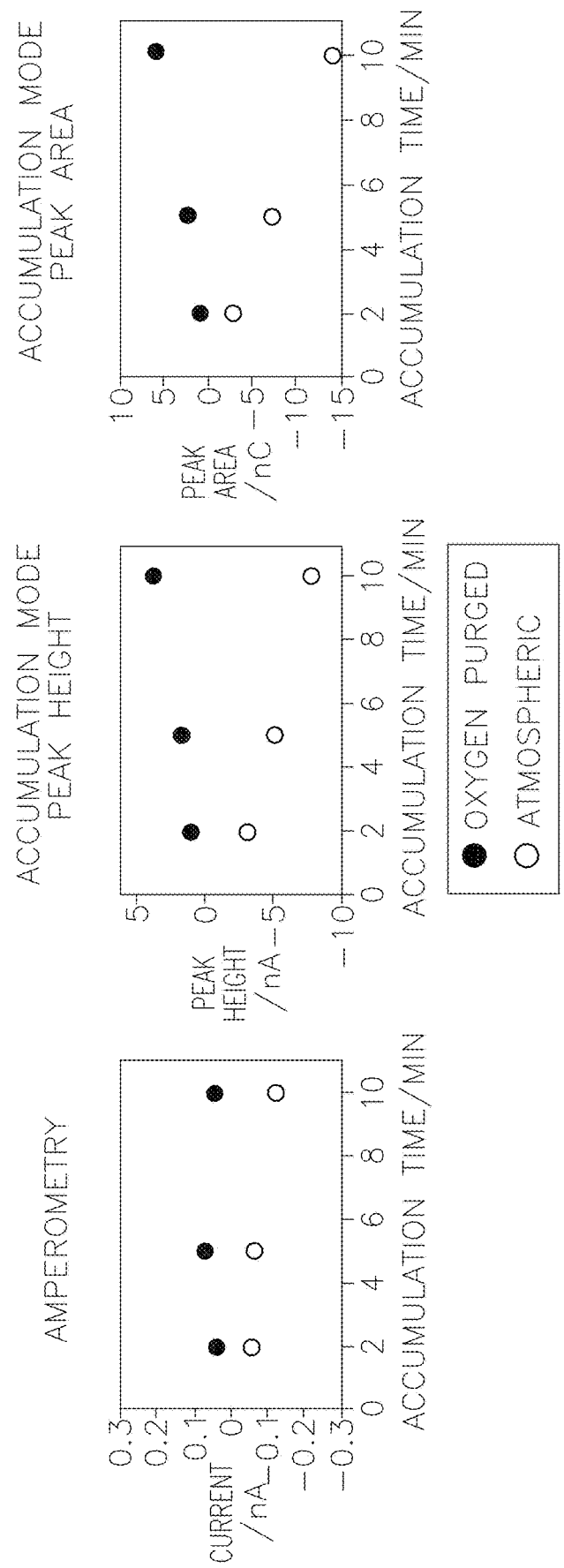
FIG. 10B shows a summary of the background amperometry and accumulation mode signals from the experiment shown in FIG. 10A in which the signals are the mean (average) of 4 sensors, and the oxygen-purged data is shown as solid circles and the atmospheric data is shown as open circles, according to embodiments of the present disclosure.

With reference to FIGS. 9A and 9B, a negative (cathodic) background signal is observed when sensing is carried out in buffer solution that is open to the atmosphere. Without being limited by any theory, the oxygen reduction reaction is likely responsible for this negative background. Specifically, the osmium redox mediator and CNTs could catalyze the oxygen reduction reaction, which would result in the oxidation of the osmium mediator resulting in a buildup of Os3+ when the circuit is disconnected during the accumulation period. When the circuit is reconnected, this buildup of Os3+ could be reduced, resulting in a cathodic peak. To test this hypothesis, example glucose sensors were tested in 100 mM phosphate buffer containing no glucose under atmospheric conditions and oxygen-purged (e.g., via bubbling) conditions. FIG. 10A shows the resulting accumulation mode signal obtained for a representative sensor for accumulation times of 2, 5, and 10 minutes under atmospheric and oxygen-purged conditions, as indicated. As observed, the signals are cathodic peaks under atmospheric conditions, while under oxygen-purged conditions the signals are smaller anodic peaks. The mean (average) signals for 4 sensors are plotted in FIG. 10B. As shown, the amperometry signal is observed from slightly negative under atmospheric conditions to slightly positive under oxygen-purged conditions. The results of this experiment indicate that the negative background is due to Os-catalyzed oxygen reduction.

Example 5. Linear Detection Range

Figure 11:
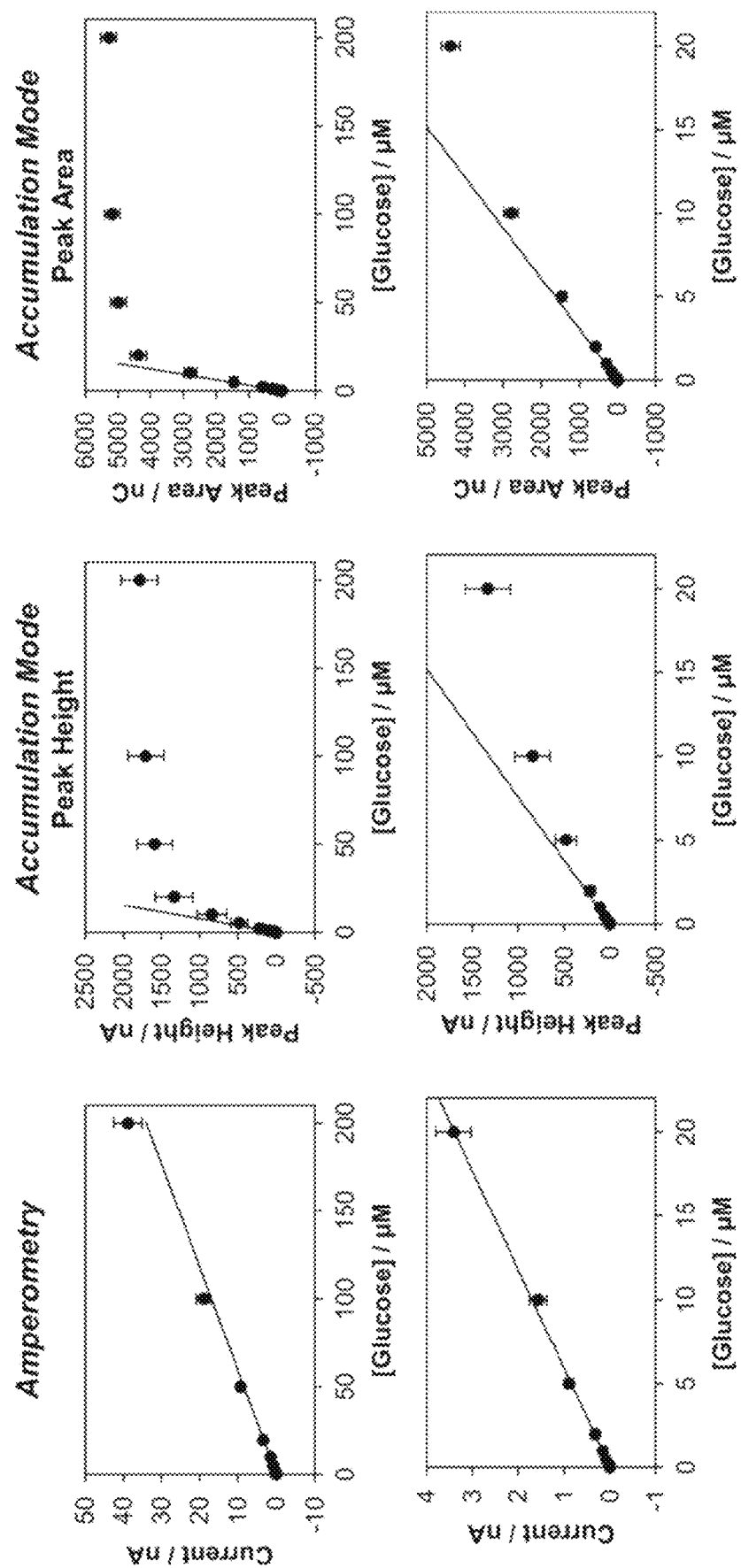
FIG. 11 shows calibration curves obtained for amperometry and accumulation mode sensing (peak height and peak area) during a sensing experiment with glucose concentrations from 0 to 200 µM, with the linear lines shown as the linear best fit lines obtained for concentrations from 0 to 200 nM that are forecasted to the higher concentrations, and each signal is the mean of 8 sensors, according to embodiments of the present disclosure.

To determine the linear detection range of accumulation mode sensing, the calibration experiment shown in FIGS. 9A and 9B were carried out up to glucose concentrations of 200 µM. The resulting amperometry and accumulation mode calibration curves are shown in FIG. 11. The linear best fit line determined for concentrations from 0 to 200 nM was forecasted to higher concentrations. As seen, the amperometry signal remains linear up to at least 100 µM. The accumulation mode signal, on the other hand, remains linear up to 2 to 5 µM before beginning to plateau at higher concentrations. This is to be expected, as the Os redox mediator has a finite charge storage capacity. For the sensors used in this experiment, this capacity appears to be about 5000 nC. It is noted that the linear range of accumulation mode sensing could be shifted to higher concentrations if a shorter accumulation time is used. For the data shown herein, a relatively long (e.g., 30 minute) accumulation time was used to obtain high sensitivity.

Example 6. Materials

Screen-printed carbon sensors on PET substrates were obtained from Steven Label, Inc. (Santa Fe Springs, Calif.). The active area of the working electrode was defined by the deposited area of a glucose-oxidizing catalyst, which was roughly 0.1 mm$^2$. A proprietary redox polymer used for glucose oxidase (GOx) wiring and a proprietary flux-limiting membrane polymer were synthesized according to published procedures, and obtained from Nanosyn, Inc. (Santa Rosa, Calif.) and Regis Technologies, Inc. (Morton Grove, Ill.), respectively. Glucose oxidase (GOx, EC 1.1.3.4, activity 130 U/mg) from *Aspergillus* sp. II was obtained from Toyobo Co, Ltd. (Osaka, Japan). Poly(ethylene glycol) (400) diglycidyl ether (PEGDGE 400) and glyceryl triglycidyl ether was obtained from Polysciences, Inc. (Warrington, Pa.). Multi-walled carbon nanotubes (CNTs, OD 20-40 nm, length 10-20 µm) were obtained from MK Nano (Mississauga, Ontario, Canada). Glucose and the common chemicals used for buffer solutions were obtained from Sigma-Aldrich (St. Louis, Mo.). All aqueous solutions were made using >18.0 MΩ·cm$^{-1}$ deionized water obtained from a Thermo Scientific Barnstead E-Pure ultrapure water purification system.

Example 7. Sensor Fabrication

Two different types of glucose sensing reagents were used, one without CNTs and one with CNTs. The non-CNT reagent was prepared as follows. First, three solutions were prepared in 10 mM 4-(2-hydroxyethyl)piperazine-1-ethanesulfonic acid (HEPES) buffer (pH 8): 4% (w/v) redox polymer, 8.08% (w/v) GOx, and 8.08% (w/v) PEGDGE400. These three solutions were mixed in a 3.04:5.1:1.86 ratio to yield the glucose sensing reagent. To prepare the glucose sensing reagent with CNTs, the above procedure was followed, except the 4% redox polymer solution and 8.08% PEGDGE400 solution were prepared in an aqueous 5% (w/v) CNT solution instead of 10 mM HEPES solution. Following preparation, the glucose sensing reagent was dispensed onto the carbon working electrode of the sensor via a microsyringe (Hamilton Co.) in 15 nL aliquots. The active area of each working electrode was defined by the area of the dispensed sensing reagent droplet. This area was typically 0.1 mm$^2$. Following dispensing of the sensing reagent, sensors were cured at 25° C. and 60% relative humidity for at least 12 hours. For the sensors used in the experiment shown in FIG. 5, an outer, flux-limiting polymer membrane was applied to the sensors. This membrane, which consisted of a 4:1 by volume mixture of 14% (w/v) membrane polymer and 3.5% (w/v) glyceryl triglycidyl ether in 80/20 ethanol/water, was applied via dip-coating as previously described in Liu et al., *Anal. Chem.* 2012, 84:3403-3409, the entire content of which is herein incorporated by reference.

Example 8. Electrochemical Measurements

Unless indicated otherwise, all electrochemical measurements were made using a suitable three-electrode cell with the glucose sensor as the working electrode, a Ag/AgCl reference electrode (in 3M KCl; Bioanalytical Systems, Inc.), and a screen-printed carbon counter electrode. The current versus (vs.) time trace for a sensor was measured throughout the course of an accumulation mode experiment using a potentiostat. For an accumulation mode measurement, the working electrode was electrically disconnected from the potentiostat for a set amount of time (the accumulation time), after which point it was reconnected to the circuit. FIG. 2 shows a scheme of the electrode diagram. When the working electrode of a sensor was electrically connected, it was poised at +40 mV. For the experiments shown in FIGS. 3A-3D, 4A-4B, 5, and 6A-6H, a BASi Petit Ampere potentiostat (model LC-3D; Bioanalytical Systems, Inc., West Lafayette, Ind.) was used for current measurements. A 0.5 second (s) sampling interval and 0.03 Hz filter were used, and the current signal was recorded using in-house LabView (National Instruments) software. For all other experiments, an increased time resolution was desired. Therefore, a potentiostat with higher time resolution was used (model 1030C; CH Instruments, Inc., Austin, Tex.). This potentiostat was used with a 0.1 second sampling interval and a 3.2 Hz filter except for those shown in FIGS. 7 and 8B. For those experiments, this potentiostat was used with a 0.1 s sampling interval and either a 3.2 Hz filter or a 0.032 Hz filter, as indicated. This signal was recorded using manufacturer-provided software. Measurements of peak area, peak height, and amperometric current in the resulting current vs. time traces were made using Graphpad Prism 6 software. All experiments were carried out in 100 mM PBS buffer (pH=7.4, 100 mM NaCl) and at 33° C.

As disclosed herein and shown throughout, accumulation mode sensing according to embodiments of the present disclosure may be utilized to give superior detection over amperometry at low analyte concentrations.

While the present disclosure has been illustrated and described with reference to certain exemplary embodiments, those of ordinary skill in the art will understand that various modifications and changes may be made to the described embodiments without departing from the spirit and scope of the present disclosure, as defined in the following claims.

What is claimed is:

1. A method for sensing an analyte utilizing a sensor, the sensor including a working electrode, the method comprising:
    providing the working electrode with a sensing element comprising an analyte-specific enzyme, a redox mediator, and carbon nanotubes;
    providing the working electrode to the analyte;
    accumulating charge on the redox mediator by allowing the analyte to react with the analyte-specific enzyme for a set period of time;
    connecting the working electrode to a circuit after the set period of time; and
    measuring a signal from the accumulated charge,
    wherein the redox mediator comprises a redox species selected from osmium, ruthenium, iron, cobalt, and compounds or complexes thereof, coupled with a polymer selected from poly (vinylpyridine), poly(thiophene), poly(aniline), poly(pyrrole), and poly(acetylene), and
    wherein the measuring of the signal from the accumulated charge comprises filtering the signal at a frequency of 0.032 to about 3.2 hertz (Hz).

2. The method of claim 1, wherein the method further comprises connecting the working electrode to the circuit prior to providing the working electrode to the analyte, and disconnecting the working electrode from the circuit after providing the working electrode to the analyte.

3. The method of claim 1, wherein after providing the working electrode to the analyte, the method further comprises connecting the working electrode to the circuit, measuring an amperometric current, and then disconnecting the working electrode from the circuit to begin accumulating charge.

4. The method of claim 1, wherein the sensor is an enzymatic electrochemical biosensor.

5. The method of claim 1, wherein the redox mediator is an immobilized redox polymer.

6. The method of claim 1, wherein the analyte is selected from the group consisting of cortisol, glucose, lactate, 3-hydroxy butyrate, alcohol, pyruvate, glutamate, theophylline, and creatinine.

7. The method of claim 1, wherein the analyte-specific enzyme is selected from the group consisting of a nicotinamide adenine dinucleotide (NAD)-dependent dehydrogenase, a flavin adenine dinucleotide (FAD)-dependent oxidase, and a flavin mononucleotide (FMN)-dependent oxidase.

8. The method of claim 1, wherein the analyte-specific enzyme is selected from the group consisting of 11β-hydroxysteroid dehydrogenase type 2 (11β-HSD-2), glucose oxidase, NAD-glucose dehydrogenase, FAD-glucose dehydrogenase, lactate oxidase, NAD-lactate dehydrogenase, NAD-alcohol dehydrogenase, pyruvate oxidase, NAD-glutamate dehydrogenase, and xanthine oxidase.

9. The method of claim 1, wherein the analyte is at a concentration equal to or greater than 4.7 nanomolar.

10. The method of claim 1, wherein the measuring of the signal from the accumulated charge comprises measuring a peak height of the signal and/or measuring a peak area of the signal.

11. The method of claim 10, further comprising calibrating the measured peak height to provide a concentration of the analyte.

12. The method of claim 10, further comprising calibrating the measured peak area to provide a concentration of the analyte.

13. The method of claim 1, wherein the measuring of the signal from the accumulated charge comprises recording the signal at a sampling rate of 0.1 to 0.5 hertz (Hz).

14. A system for sensing an analyte, the system comprising:
    a working electrode;
    a sensing element disposed on the working electrode, the sensing element comprising an analyte-specific enzyme, a redox mediator, and carbon nanotubes, the sensing element configured to accumulate charge on the redox mediator by allowing the analyte to react with the analyte-specific enzyme for a set period of time; and
    a circuit configured to connect with the working electrode after the set period of time and to measure a signal from the accumulated charge,
    wherein the redox mediator comprises a redox species selected from osmium, ruthenium, iron, cobalt, and compounds or complexes thereof, coupled with a polymer selected from poly (vinylpyridine), poly(thiophene), poly(aniline), poly(pyrrole), and poly(acetylene), and
    wherein the measuring of the signal from the accumulated charge comprises filtering the signal at a frequency of about 3.2 hertz (Hz).

15. The system of claim 14, further comprising an outer membrane overlaying at least the sensing element.

16. The system of claim 14, wherein the analyte-specific enzyme is selected from the group consisting of a nicotinamide adenine dinucleotide (NAD)-dependent dehydrogenase, a flavin adenine dinucleotide (FAD)-dependent oxidase, and a flavin mononucleotide (FMN)-dependent oxidase.

17. The system of claim 14, wherein the analyte-specific enzyme is selected from the group consisting of 11β-hydroxysteroid dehydrogenase type 2 (11β-HSD-2), glucose oxidase, NAD-glucose dehydrogenase, FAD-glucose dehydrogenase, lactate oxidase, NAD-lactate dehydrogenase, NAD-alcohol dehydrogenase, pyruvate oxidase, NAD-glutamate dehydrogenase, and xanthine oxidase.

* * * * *